United States Patent [19]
Alt

[11] 4,451,285
[45] * May 29, 1984

[54] HERBICIDAL 2-HALOACETANILIDES

[75] Inventor: Gerhard H. Alt, University City, Mo.

[73] Assignee: Monsanto Company, St. Louis, Mo.

[*] Notice: The portion of the term of this patent subsequent to Jun. 1, 1999 has been disclaimed.

[21] Appl. No.: 383,039

[22] Filed: May 28, 1982

Related U.S. Application Data

[63] Continuation-in-part of Ser. No. 133,765, Mar. 25, 1980, Pat. No. 4,332,614.

[51] Int. Cl.$^3$ .................... A01N 37/34; A01N 37/24; C07C 103/34; C07C 121/78
[52] U.S. Cl. .......................................... 71/105; 71/88; 71/90; 71/95; 71/118; 260/465 D; 548/517; 548/527; 549/76; 549/496; 564/214

[58] Field of Search ................. 564/214; 260/465 D; 71/88, 90, 95, 105, 118; 548/517, 527; 549/76, 496

[56] References Cited

U.S. PATENT DOCUMENTS 3,268,584  8/1966  Olin ..................................... 71/118
3,547,620  12/1970  Olin ..................................... 71/118
3,642,895  2/1972  Adams, Jr. et al. ................. 71/118
3,965,139  6/1976  Scozzie ........................... 260/465 D Primary Examiner—Dolph H. Torrence
Attorney, Agent, or Firm—William I. Andress; Richard H. Shear; Arnold H. Cole

[57] ABSTRACT

The present disclosure relates to a new class of 2-haloacetanilide derivatives which are useful as herbicides. This disclosure further relates to herbicidal compositions containing such 2-haloacetanilides and to herbicidal methods of use employing such compounds and compositions.

33 Claims, No Drawings

HERBICIDAL 2-HALOACETANILIDES

This application is a continuation-in-part of copending U.S. Ser. No. 133,765, filed Mar. 25, 1980, U.S. Pat. No. 4,332,614.

The present invention relates to a new class of 2-haloacetanilide derivatives which are useful as herbicides. This invention further relates to herbicidal compositions containing such 2-haloacetanilides and to herbicidal methods of use employing such compounds and compositions.

The compounds of the present invention are represented by the formula

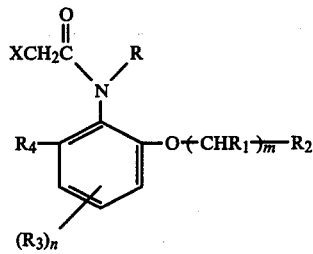

wherein
X is chloro, bromo or iodo;
R is H, $C_{1-5}$ alkyl or alkoxymethyl, cyanomethyl, azolylmethyl, $C_{3-5}$ alkenyl, alkynyl or alkenyloxymethyl;
$R_1$ and $R_3$ are H or $C_{1-4}$ alkyl;
$R_2$ is $C_{1-4}$ alkoxy, polyalkoxy, alkoxyalkyl or dialkoxymethyl, 2-furyl, 2-tetrahydrofuryl or 2-thienyl;
$R_4$ is H, $C_{1-4}$ alkyl or halogen;
m is 1 or 2; and
n is 1–3;
provided that when R is alkoxymethyl, $R_4$ is hydrogen or halogen.

Preferred compounds according to the above formula are those wherein X is chlorine; $R_1$, $R_3$ and $R_4$ are hydrogen or methyl; $R_2$ is $C_{1-4}$ alkoxy or alkoxyalkyl and R is $C_{1-4}$ alkyl or alkoxyalkyl and R is $C_{1-4}$ alkyl or alkoxymethyl, cyanomethyl or propargyl.

Preferred species of invention compounds are: 2-chloro-[2′-(2-methoxy-1-methylethoxy)-6′-methyl]-N-methylacetanilide, 2-chloro-[2′-(2-isopropoxyethoxy)-6′-methyl]-N-methyl-acetanilide, 2-chloro-[2′-(2-methoxyethoxy)-6′-methyl]-N-(cyanomethyl)acetanilide, 2-chloro-[-2′-ethoxyethoxy)-6′-methyl]-N-ethylacetanilide, 2-chloro-[2′-(ethoxymethoxy)-6′-methyl]-N-(2-propynyl) acetanilide, 2-chloro-[2′-(2-ethoxyethoxy)-6′-chloro]-N-(ethoxymethyl)acetanilide.

As employed herein, the term "alkyl" designates alkyl radicals which may have a straight or branched chain; preferred members are $C_{1-5}$ alkyl. Groups representative of these radicals include, for example, methyl, ethyl, propyl, isopropyl, butyl, isobutyl, t-butyl, pentyl, hexyl, octyl, isooctyl, decyl and the like.

As employed herein, the term "alkenyl" designates alkenyl radicals which may have a straight or branched chain. Groups representative of these radicals include, for example, propenyl, butenyl, 2-methylpropenyl, cis-2-butenyl, trans-2-butenyl, 4-methyl-2-pentenyl and the like.

As employed herein, the term "alkynyl" designates alkynyl radicals which may have a straight or branched chain. Groups representative of these radicals include, for example, propynyl, 1-butynyl, 3-methyl-1-butynyl, 3,3-dimethyl-1-butynyl and the like.

As employed herein the terms "alkoxy" and "polyalkoxy" designate alkoxy and polyalkoxy radicals which may have a straight or branched chain. Groups representative of these alkoxy radicals include, for example, methoxy, ethoxy, propoxy, isopropoxy, butoxy, t-butoxy and the like. Representative polyalkoxy groups include methoxymethoxy, methoxyethoxy, ethoxymethoxy, ethoxyethoxy, propoxyethoxy, isopropoxymethoxy, butoxymethoxy, isobutoxyethoxy and the like.

Groups representative of the term "alkoxyalkyl" include, for example, methoxymethyl, ethoxyethyl, propoxymethyl, isopropoxymethyl, propoxybutyl, butoxyethyl, isobutoxyethyl, isobutoxymethyl, methoxyethyl, pentoxymethyl and the like.

The term "alkenyloxymethyl" includes such radicals as allyloxymethyl, methallyloxymethyl, butenyloxymethyl, pentenyloxymethyl and the like.

The term "dialkoxymethyl" includes the acetal radicals such as 1,1-dimethoxymethyl, 1,1-diethoxymethyl, 1,1-dipropoxymethyl, 1,1-dibutoxymethyl, 1,1-dipentoxymethyl and the like.

The term "azolylmethyl" includes radicals such as pyrazolylmethyl, imidazolylmethyl, triazolylmethyl, tetrazolylmethyl or such radicals substituted with one or more $C_{1-4}$ alkyl radicals and the like.

The term "halogen" as used herein includes chlorine, bromine, fluorine and iodine.

In accordance with the present invention, the compounds of formula (I) may be prepared utilizing the following procedures:

Procedure A: To prepare the compounds of formula (I) wherein R is hydrogen, the following procedure is employed.

A substituted nitrobenzene of the formula

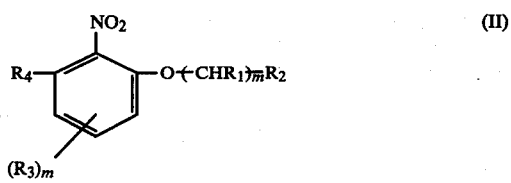

wherein $R_1$, $R_2$, $R_3$, $R_4$, m and n are above defined, is reduced to the corresponding primary amine of the formula

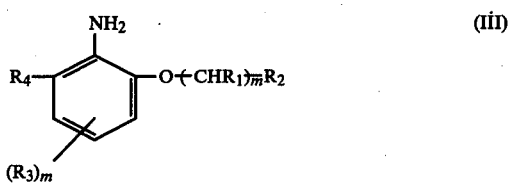

in the presence of an alcohol or other solvents commonly used in hydrogenations, e.g., ethers, esters, etc., if necessary, and a catalyst.

The primary amine of formula (III) is reacted with an alpha-haloacetyl halide or haloacetic anhydride in a solvent under basic conditions to yield a secondary amide of the formula

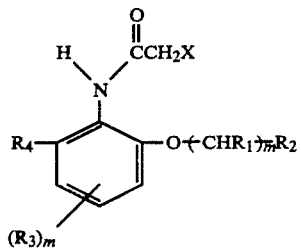

(IV)

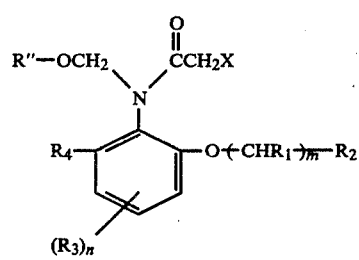

(VII)

The reactions in Procedure A can be carried out in the presence or absence of solvents or diluents which are inert towards the reactants. Examples of suitable solvents or diluents, or the haloacetylation step are aliphatic, aromatic or halogenated hydrocarbons, such as benzene, toluene, xylene, petroleum ether, chlorobenzene, methylene chloride, ethylene chloride, chloroform; ethers and ethereal compounds, such as acetonitrile, N,N-dialkylated amides, such as dimethyl formamide; as well as mixtures of these solvents.

Suitable chloroacetylating agents are, for example, chloroacetic anhydride, and chloroacetic halides, such as chloroacetyl chloride. However, it is also possible to carry out the reaction using chloroacetic acid, or its esters or amides. The process of Procedure A is carried out at temperatures between 0° C. and 200° C., preferably between 20° C. and 100° C. The chloroacetylation step is usefully carried out in the presence of an acid binding agent (especially if chloroacetyl halides are used). Suitable acid binding agents are tertiary amines, such as trialkylamines, e.g., triethylamine, pyridine and pyridine bases, or inorganic bases, such as oxides and hydroxides, hydrogen carbonates and carbonates or alkali and alkaline earth metals. Furthermore, it is also possible to use an excess of the corresponding aniline of the formula (III) as an acid binding agent. The chloracetylation step may also be carried out without an acid binding agent by, e.g., passing nitrogen through the reaction mixture where chloroacetyl halide is used.

To prepare the compounds of formula (I) wherein R is not hydrogen, the following procedures may be employed.

Procedure B: A secondary amide of formula (IV) is reacted in situ with a compound of the formula

RX₁ (V)

wherein R is above defined but not hydrogen and X₁ is halogen; under basic conditions in the presence of a phase transfer catalyst.

Procedure C: To prepare compounds of formula (I) where R is a

R″—O—CH₂— group wherein R″ is lower alkyl can be employed utilizing a procedure similar to Procedure B but characterized as a "one pot" in situ process.

A mixture containing an alcohol of the formula

R″—OH (VI)

wherein R″ is lower alkyl; formaldehyde and an acetyl halide is treated with a secondary amide of formula (IV) under basic conditions in the presence of a phase transfer catalyst to yield a compound of the formula Procedure D: To prepare compounds of formula (I) wherein R is $C_1$–$C_{10}$ alkyl, a procedure similar to Procedure B can be employed.

A compound of formula (IV) is reacted with an alkyl sulfate of the formula (RO)₂SO₂ (VIII)

wherein R is $C_1$–$C_{10}$ alkyl, in a solvent, under basic conditions in the presence of a phase transfer catalyst to yield a compound of formula (I) wherein R is $C_1$–$C_{10}$ alkyl.

It will be understood that the weaker the acidity of the amide of formula (IV), the stronger must be the base. Thus, e.g., weakly acidic amides require strong bases such as aqueous or solid sodium hydroxide or potassium hydroxide. Further, it is preferred when aqueous caustic is used that the solution be concentrated; (i.e., 20–50%).

On the other hand, in the alkylation of strongly acidic materials it can be demonstrated that a weaker base such as solid or aqueous sodium carbonate can be used to alkylate the amide.

Useful phase transfer catalysts are those containing organic-soluble cations such as those enumerated in U.S. Pat. No. 3,992,432, including ammonium, phosphonium and sulfonium salts. Exemplary phase transfer catalysts include quaternary ammonium salts, e.g., aryl or aralkyl trialkyl ammonium halide salts such as benzyl triethyl ammonium bromide or chloride. Other phase transfer catalysts include the acyclic and cyclic poly ethers which complex with the base cation and then pair with amide anion as counter ion for transport to the organic phase for alkylation. Exemplary of such catalysts would include "18-crown-6" cyclic ether in combination with potassium hydroxide or fluoride as base.

Other bases in Procedures B, C and D are dependent, however, on sec-amide acidity are alkali metal hydroxides, carbonates, and phosphates and alkaline earth hydroxides, e.g., calcium oxide or hydroxide, trisodium phosphate, potassium carbonate.

Inert solvents for use in Procedures B, C and D include, e.g., esters of alkanoic acids and alkanols such as ethyl acetate, etc., dichloromethane, benzene, chlorobenzene, tetrahydrofuran, toluene, diethyl ether. When aqueous bases are used, the solvent should be appreciably water insoluble.

Procedure E: Compounds of the formula

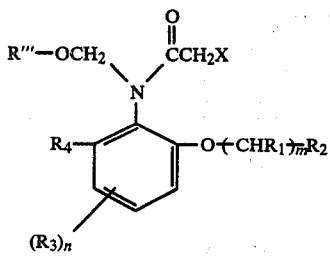

are prepared by transetherification of a compound of the formula

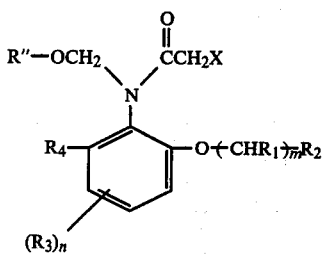

with a compound of the formula

R'''—OH   (XI)

wherein X, $R_1$, $R_2$, $R_3$, $R_4$ m and n are above defined; in an inert solvent at reflux temperatures in the presence of an acid catalyst.

R'' and R''' are independently $C_{1-5}$ alkyl or $C_{3-5}$ alkenyl.

Suitable solvents which may be used in Procedure E include aliphatic and aromatic hydrocarbons or halogenated hydrocarbons such as naphtha, the halogenated alkanes, e.g., carbon tetrachloride, chloroform, ethylene dichloride, trichloroethane, etc., benzene, halogenated benzenes, toluene, the xylenes and other inert solvents.

Other acid catalysts which may be used in the process of this invention include inorganic acids such as $H_2SO_4$, $H_3PO_4$; the hydrohalides, HCl, HBr, HI; sulfonic acids such as sulphamic acid, methanesulfonic acid, benzenesulfonic acid, p-toluenesulfonic acid, etc.; Lewis Acids, e.g., $BF_3$, $BF_3$ etherates, $AlCl_3$, etc. It is within the purview of this invention to use salts of organic acids as acidic catalysts. Examples of such salts are the halides and acetates, oxalates, etc., of boron, copper and mercury. It is also within the purview of this invention to use acidic ion-exchange resins such as sulphonated styrene polymers or co-polymers which may contain from 1–15% by weight of a cross-linking agent such as divinylbenzene.

Molecular sieves which may be used herein include natural zeolites (alumino-silicates) or synthetic zeolites such as alkali metal alumino-silicate hydrates exemplified by Type 3A, i.e., $K_9Na_3[(AlO_2)_{12}(SiO_2)_{12}].27H_2O$; Type 4A, i.e., $Na_{12}[(AlO_2)_{12}(SiO_2)_{12}].27H_2O$; Type 5A, i.e., $Ca_{4.5}Na_3[(AlO_2)_{12}].3H_2O$, etc. The criteria for selection of a particular molecular sieve is that its intercellular pore size be small enough to trap or absorb by-product alcohol while excluding larger molecules. As used herein, molecular sieves are preferably used to absorb methanol and water in embodiments in which these by-products are formed.

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE 1

A mixture containing 6-methyl-2-methoxyethoxy-nitrobenzene (21.1 g; 0.1 mole) in 100 ml. of ethanol and 1 g. of 5% palladium on charcoal catalyst was hydrogenated on a Parr hydrogeneration apparatus at 50 psi for 3 hours. The reaction mixture was filtered to remove the catalyst and then concentrated to yield a residual oil which solidified to yield 6-methyl-2-methoxyethoxy aniline. A portion of the 6-methyl-2-methoxyethoxy aniline (15.3 g; 0.085 mole) in 100 ml. of methylene chloride was cooled in an ice bath. To the cooled reaction mixture was added all at once 80 ml. of a 10% sodium hydroxide solution (0.2 mole). To the resulting mixture was added chloroacetyl chloride (11.3 g; 0.1 mole) in 70 ml. of methylene chloride and the resulting mixture was stirred at room temperature for 2 hours. The layers were separated and the organic methylene chloride layer was washed with water, a saturated sodium chloride solution, dried over magnesium sulfate and concentrated to yield a crude product. The crude product was recrystallized from an aqueous methanol solution to yield 2-chloro-[2'-(2-methoxyethoxy)-6-methyl]acetanilide (Compound No. 1) (14.1 g; 64%) as a white solid. The data for Compound No. 1 and Compound Nos. 2–17 prepared employing a similar procedure is summarized in Table I.

TABLE I

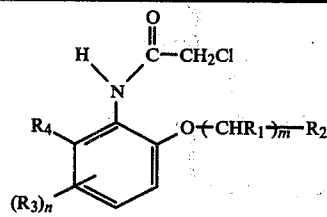

| Compound Number | $+CHR_1)_{\overline{m}}$ | $R_2$ | $R_3$ | $R_4$ | m.p. °C. | Element | Analysis Calc'd | Found |
|---|---|---|---|---|---|---|---|---|
| 1 | —CH$_2$CH$_2$— | —OCH$_3$ | —H | —CH$_3$ | 130–132 | C | 55.93 | 55.96 |
|  |  |  |  |  |  | H | 6.26 | 6.31 |
|  |  |  |  |  |  | N | 5.44 | 5.45 |
|  |  |  |  |  |  | Cl | 13.76 | 13.72 |
| 2 | —CH$_2$CH$_2$— | —OCH$_3$ | —H | —H | (a) | C | 54.22 | 54.00 |
|  |  |  |  |  |  | H | 5.79 | 5.83 |

TABLE I-continued

| Compound Number | ‑(CHR₁)ₘ‑ | R₂ | R₃ | R₄ | m.p. °C. | Element | Calc'd. | Found |
|---|---|---|---|---|---|---|---|---|
| | | | | | | N | 5.75 | 5.72 |
| | | | | | | Cl | 14.55 | 14.56 |
| 3 | —CH₂CH₂— | —OCH₂CH₃ | —H | —CH₃ | 101–102 | C | 5.744 | 57.40 |
| | | | | | | H | 6.67 | 6.70 |
| | | | | | | N | 5.19 | 5.15 |
| | | | | | | Cl | 13.04 | 13.02 |
| 4 | —CH₂CH₂— | —O(CH₂)₃CH₃ | —H | —CH₃ | 85–86 | C | 60.10 | 60.04 |
| | | | | | | H | 7.40 | 7.39 |
| | | | | | | N | 4.67 | 4.66 |
| | | | | | | Cl | 11.83 | 11.81 |
| 5 | —CH₂CH₂— | —OCH(CH₃)₂ | —H | —CH₃ | 95–95.5 | C | 58.84 | 58.88 |
| | | | | | | H | 7.05 | 7.08 |
| | | | | | | N | — | — |
| | | | | | | Cl | 12.41 | 12.51 |
| 6 | CH₃<br>\|<br>—CH—CH₂— | —OCH₃ | —H | —CH₃ | 87.5–88 | C | 57.46 | 57.42 |
| | | | | | | H | 6.68 | 6.69 |
| | | | | | | N | — | — |
| | | | | | | Cl | 13.05 | 13.09 |
| 7 | —CH₂CH₂— | —OCH₃ | —H | —CH(CH₃)₂ | 97–98 | C | 58.84 | 58.86 |
| | | | | | | H | 7.05 | 7.06 |
| | | | | | | N | — | — |
| | | | | | | Cl | 12.41 | 12.38 |
| 8 | —CH₂CH₂— | —OCH₂CH₃ | —H | —H | 36–37 | C | 55.93 | 55.86 |
| | | | | | | H | 6.26 | 6.27 |
| | | | | | | N | — | — |
| | | | | | | Cl | 13.76 | 13.78 |

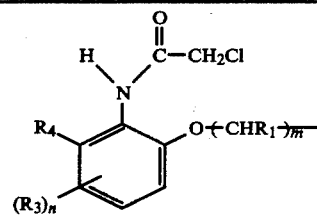

| Compound Number | ‑(CHR₁)ₘ‑ | R₂ | R₃ | R₄ | m.p. °C. | Element | Calc'd. | Found |
|---|---|---|---|---|---|---|---|---|
| 9 | —CH₂CH₂— | —OCH₂CH(CH₃)₂ | —H | —CH₃ | 91 | C | 60.10 | 60.12 |
| | | | | | | H | 7.40 | 7.41 |
| | | | | | | N | — | — |
| | | | | | | Cl | 11.83 | 11.79 |
| 10 | —CH₂— | —OCH(CH₃)₂ | —H | —CH₃ | 103–105 | C | 57.46 | 57.48 |
| | | | | | | H | 6.68 | 6.69 |
| | | | | | | N | — | — |
| | | | | | | Cl | 13.05 | 13.05 |
| 11 | —CH₂CH₂CH₂— | —O—C₆H₅ (phenyl) | —H | —CH₃ | 107–109 | C | 64.77 | 64.68 |
| | | | | | | H | 6.04 | 6.05 |
| | | | | | | N | — | — |
| | | | | | | Cl | 10.62 | 10.60 |
| 12 | —CH₂— | tetrahydrofuranyl | —H | —H | 125–127 | C | 59.26 | 59.36 |
| | | | | | | H | 6.39 | 6.39 |
| | | | | | | N | — | — |
| | | | | | | Cl | 12.49 | 12.49 |

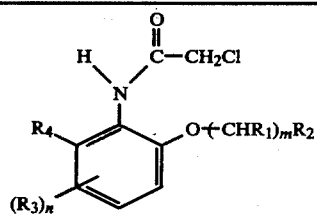

| Compound Number | ‑(CHR₁)ₘ‑ | R₂ | R₃ | R₄ | m.p. °C. | Element | Calc'd. | Found |
|---|---|---|---|---|---|---|---|---|
| 13 | —CH₂CH₂— | —O(CH₂)₂OCH₃ | —H | —CH₃ | 71 | C | 55.72 | 55.53 |
| | | | | | | H | 6.68 | 6.67 |
| | | | | | | N | — | — |
| | | | | | | Cl | 11.75 | 11.65 |
| 14 | —CH₂ | —O(CH₂)₃CH₃ | —H | —CH₃ | 94 | C | 58.84 | 58.81 |
| | | | | | | H | 7.01 | 7.06 |
| | | | | | | N | — | — |

TABLE I-continued

| | | | | | | | Cl | 12.43 | 12.42 |
|---|---|---|---|---|---|---|---|---|---|
| 15 | —CH$_2$—CH(OCH$_3$)— | —OCH$_3$ | —H | —CH$_3$ | 100 | C | | 54.26 | 54.13 |
| | | | | | | H | | 6.31 | 6.35 |
| | | | | | | N | | — | — |
| | | | | | | Cl | | 12.32 | 12.42 |
| 16 | —CH$_2$— | —OCH$_2$CH$_3$ | —H | —CH$_3$ | 92–95 | C | | 55.93 | 55.81 |
| | | | | | | H | | 6.26 | 6.30 |
| | | | | | | N | | — | — |
| | | | | | | Cl | | 13.76 | 13.85 |

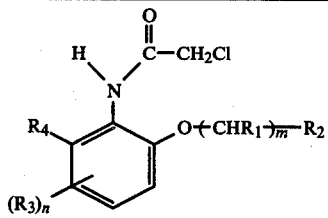

| Compound Number | —(CHR$_1$)$_m$— | R$_2$ | R$_3$ | R$_4$ | m.p. °C. | Element | Calc'd. | Found |
|---|---|---|---|---|---|---|---|---|
| 17 | —CH$_2$— | (tetrahydrofuran) | —CF$_3$ | —H | 67–69 | C | 49.79 | 49.84 |
| | | | | | | H | 4.48 | 4.49 |
| | | | | | | N | 4.15 | 4.13 |
| | | | | | | Cl | 10.50 | 10.47 |

(a) Boiling Point = 135° C. @ 0.1 mmHg

EXAMPLE 2

A mixture containing 2-chloro-[2'-(2-ethoxyethoxy)-6-methyl]acetanilide (4.7 g; 0.015 mole); (bromomethyl) methyl ether (3.75 g; 0.03 mole); 1.5 g. of benzyltriethylammonium bromide and 250 ml. of methylene chloride was cooled to 0° C. While maintaining the temperature of the reaction mixture below 15° C., 50 ml. of a 50% solution of sodium hydroxide was added to the reaction mixture and the resultant mixture was stirred for 1 hour. To the reaction mixture was added 100 ml. of cold water. The layers were separated, and the organic layer was washed with water, dried over magnesium sulfate and concentrated in vacuo to yield 2-chloro-N-(methoxymethyl)-[2'-(2-ethoxyethoxy-6-methyl]acetanilide (4.7 g; 99% yield) (Compound No. 30) as an amber oil. The data for Compound No. 30 and other compounds prepared employing a similar procedure is summarized in Table II.

TABLE II

| Compound No. | m | R$_2$ | R$_3$ | R$_4$ | R | X' | b.p. (°C.) | Element | Calc'd | Found |
|---|---|---|---|---|---|---|---|---|---|---|
| 18 | 1 | (tetrahydrofuran) | —H | —H | —CH$_2$OCH$_3$ | —Br | 130–140° C. @ 0.03 mmHg | C | 57.42 | 57.38 |
| | | | | | | | | H | 6.42 | 6.44 |
| | | | | | | | | N | 4.46 | 4.46 |
| | | | | | | | | Cl | 11.30 | 11.33 |
| 19 | 2 | —OCH$_3$ | —H | —CH$_3$ | —CH$_2$OCH$_3$ | —Br | 130–150° C. @ 0.03 mmHg | C | 55.72 | 55.66 |
| | | | | | | | | H | 6.68 | 6.68 |
| | | | | | | | | N | 4.64 | 4.63 |
| | | | | | | | | Cl | 11.75 | 11.81 |
| 20 | 2 | —OCH$_3$ | —H | —H | —CH$_2$OCH$_3$ | —Br | 134° C. @ 0.08 mmHg | C | 54.26 | 54.10 |
| | | | | | | | | H | 6.31 | 6.34 |
| | | | | | | | | N | 4.87 | 4.85 |
| | | | | | | | | Cl | 12.32 | 12.39 |
| 21 | 2 | —OCH$_3$ | —H | —H | —CH$_2$OCH$_2$CH$_3$ | —Cl | 137° C. @ 0.08 mmHg | C | 55.72 | 55.65 |
| | | | | | | | | H | 6.68 | 6.73 |
| | | | | | | | | N | 4.64 | 4.62 |
| | | | | | | | | Cl | 11.75 | 11.78 |
| 22 | 2 | —OCH$_3$ | —H | —H | —CH$_2$OCH$_2$CH$_2$CH$_3$ | —Cl | 135° C. @ 0.07 mmHg | C | 57.05 | 57.08 |
| | | | | | | | | H | 7.02 | 7.04 |
| | | | | | | | | N | 4.44 | 4.40 |
| | | | | | | | | Cl | 11.23 | 11.17 |
| 23 | 2 | —OCH$_3$ | —H | —H | —CH$_2$OCH$_2$CH(CH$_3$)$_2$ | —Cl | 150° C. @ | C | 58.27 | 58.27 |

TABLE II-continued

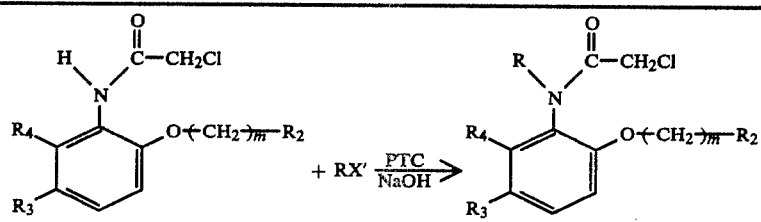

| Compound No. | m | R₂ | R₃ | R₄ | R | X' | b.p. (°C.) | Analysis Element | Calc'd | Found |
|---|---|---|---|---|---|---|---|---|---|---|
| | | | | | | | 0.08 mmHg | H | 7.33 | 7.35 |
| | | | | | | | | N | 4.25 | 4.22 |
| | | | | | | | | Cl | 10.75 | 10.64 |
| 24 | 1 | (tetrahydrofuran-2-yl) | —H | —H | —CH₂OCH₂CH(CH₃)₂ | —Cl | 150° C. @ 0.07 mmHg | C | 60.75 | 60.72 |
| | | | | | | | | H | 7.36 | 7.39 |
| | | | | | | | | N | 3.94 | 3.94 |
| | | | | | | | | Cl | 9.96 | 9.97 |
| 25 | 2 | —OCH₃ | —H | —CH₃ | —CH₂OCH₂CH(CH₃)₂ | —Cl | (b) | C | 59.38 | 59.44 |
| | | | | | | | | H | 7.62 | 7.69 |
| | | | | | | | | N | 4.07 | 4.08 |
| | | | | | | | | Cl | 10.31 | 10.28 |
| 26 | 2 | —OCH₃ | —CF₃ | —H | —CH₂OCH₂CH₃ | —Cl | 120–140° C. @ 0.04 mmHg | C | 48.72 | 48.72 |
| | | | | | | | | H | 5.18 | 5.20 |
| | | | | | | | | N | 3.79 | 3.79 |
| | | | | | | | | Cl | 9.59 | 9.51 |
| 27 | 1 | —OCH₂CH₃ | —H | —CH₃ | —CH₂OCH₂CH₂CH₃ | —Cl | 120–135° C. @ 0.03 mmHg | C | 58.27 | 58.21 |
| | | | | | | | | H | 7.33 | 7.32 |
| | | | | | | | | N | — | — |
| | | | | | | | | Cl | 10.75 | 10.71 |
| 28 | 2 | —OCH₃ | —H | —CH₃ | —CH₂OCH₂CH₃ | —Cl | 140° C. @ 0.05 mmHg | C | 57.05 | 56.88 |
| | | | | | | | | H | 7.02 | 7.07 |
| | | | | | | | | N | 4.44 | 4.44 |
| | | | | | | | | Cl | 11.23 | 11.19 |
| 29 | 2 | —OCH₃ | —H | —CH₃ | —CH₂OCH₂CH₂CH₃ | —Cl | 150° C. @ 0.06 mmHg | C | 58.27 | 58.18 |
| | | | | | | | | H | 7.33 | 7.34 |
| | | | | | | | | N | 4.25 | 4.25 |
| | | | | | | | | Cl | 10.75 | 10.67 |
| 30 | 2 | —OCH₂CH₃ | —H | —CH₃ | —CH₂OCH₃ | —Br | 145° C. @ 0.08 mmHg | C | 57.03 | 56.87 |
| | | | | | | | | H | 7.02 | 7.09 |
| | | | | | | | | N | 4.46 | 4.41 |
| | | | | | | | | Cl | 11.23 | 11.30 |
| 31 | 2 | —OCH₂CH₃ | —H | —CH₃ | —CH₂OCH₂CH(CH₃)₂ | —Cl | 158° C. @ 0.07 mmHg | C | 60.39 | 60.16 |
| | | | | | | | | H | 7.88 | 7.93 |
| | | | | | | | | N | 3.94 | 3.86 |
| | | | | | | | | Cl | 9.91 | 10.03 |
| 32 | 2 | —OCH₂CH₂CH₂CH₃ | —H | —CH₃ | —CH₂OCH₃ | —Br | 160° C. @ 0.07 mmHg | C | 59.38 | 59.10 |
| | | | | | | | | H | 7.62 | 7.59 |
| | | | | | | | | N | 4.07 | 4.05 |
| | | | | | | | | Cl | 10.31 | 10.37 |
| 33 | 2 | —OCH₂CH₂CH₂CH₃ | —H | —CH₃ | —CH₂OCH₂CH₃ | —Cl | 162° C. @ 0.08 mmHg | C | 60.41 | 60.29 |
| | | | | | | | | H | 7.89 | 7.91 |
| | | | | | | | | N | 3.91 | 3.86 |
| | | | | | | | | Cl | 9.91 | 9.96 |
| 34 | 2 | —OCH₂CH₂CH₂CH₃ | —H | —CH₃ | —CH₂OCH(CH₃)₂ | —Cl | 165° C. @ 0.08 mmHg | C | 61.36 | 61.28 |
| | | | | | | | | H | 8.13 | 8.13 |
| | | | | | | | | N | 3.77 | 3.77 |
| | | | | | | | | Cl | 9.53 | 9.54 |
| 35 | 2 | —OCH₃ | —H | —CH₃ | —CH₂CH=CH₂ | —Cl | 130° C. @ 0.15 mmHg | C | 60.50 | 59.80 |
| | | | | | | | | H | 6.77 | 6.75 |
| | | | | | | | | N | — | — |
| | | | | | | | | Cl | 11.91 | 12.08 |
| 36 | 2 | —OCH₃ | —H | —CH₃ | —CH₂C≡CH | —Br | 125° C. @ 0.1 mmHg | C | 60.91 | 60.78 |
| | | | | | | | | H | 6.13 | 6.14 |
| | | | | | | | | N | — | — |
| | | | | | | | | Cl | 11.99 | 11.97 |
| 37 | 2 | —OCH₂CH₃ | —H | —CH₃ | —CH₂OCH₂CH₂CH₃ | —Cl | 136° C. @ 0.04 mmHg | C | 59.38 | 59.29 |
| | | | | | | | | H | 7.62 | 7.67 |
| | | | | | | | | N | — | — |
| | | | | | | | | Cl | 10.31 | 10.25 |
| 38 | 2 | —OCH₂CH₃ | —H | —CH₃ | —CH₂OCH(CH₃)₂ | —Cl | 135° C. @ 0.03 mmHg | C | 59.38 | 59.31 |
| | | | | | | | | H | 7.62 | 7.67 |
| | | | | | | | | N | — | — |
| | | | | | | | | Cl | 10.31 | 10.26 |
| 39 | 1 | —OCH₂CH₃ | —H | —CH₃ | —CH₂OCH₃ | —Br | 125–135° C. @ 0.03 mmHg | C | 55.72 | 55.50 |
| | | | | | | | | H | 6.68 | 6.70 |
| | | | | | | | | N | — | — |

TABLE II-continued

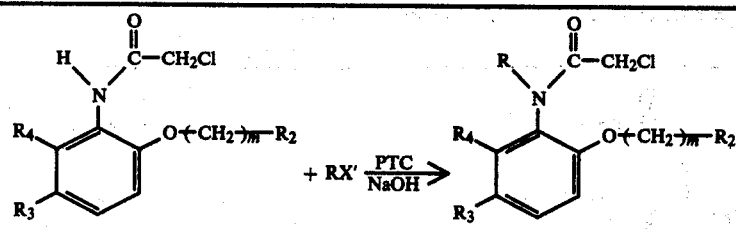

| Compound No. | m | R₂ | R₃ | R₄ | R | X' | b.p. (°C.) | Element | Calc'd | Found |
|---|---|---|---|---|---|---|---|---|---|---|
| 40 | 2 | —OCH(CH₃)₂ | —H | —CH₃ | —CH₂OCH₂CH₃ | —Cl | 140° C. @ 0.05 mmHg | Cl<br>C<br>H<br>N | 11.75<br>59.38<br>7.62<br>— | 11.68<br>59.22<br>7.63<br>— |
| 41 | 2 | —OCH₂CH₃ | —H | —CH₃ | —CH₂OCH₂CH₃ | —Cl | 135° C. @ 0.04 mmHg | Cl<br>C<br>H<br>N | 10.31<br>58.27<br>7.33<br>— | 10.29<br>58.16<br>7.34<br>— |
| 42 | 2 | —OCH(CH₃)₂ | —H | —CH₃ | —CH₂OCH₃ | —Br | 135° C. @ 0.03 mmHg | Cl<br>C<br>H<br>N | 10.75<br>58.27<br>7.33<br>— | 10.76<br>58.05<br>7.35<br>— |
| 43 | 2 | —OCH(CH₃)₂ | —H | —CH₃ | —CH₂OCH₂CH₂CH₃ | —Cl | 142° C. @ 0.03 mmHg | Cl<br>C<br>H<br>N | 10.75<br>58.27<br>7.33<br>— | 10.81<br>58.05<br>7.35<br>— |
| 44 | 2 | —OCH(CH₃)₂ | —H | —CH₃ | —CH₂OCH(CH₃)₂ | —Cl | 130° C. @ 0.02 mmHg | Cl<br>C<br>H<br>N | 10.75<br>60.41<br>7.89<br>— | 10.81<br>60.36<br>7.93<br>— |
| 45 | 2 | —OCH₂CH₃ | —H | —H | —CH₂CH=CH₂ | —Br | 117° C. @ 0.02 mmHg | Cl<br>C<br>H<br>N | 9.91<br>60.50<br>6.77<br>— | 9.90<br>60.50<br>6.80<br>— |
| 46 | 1 | —OCH₂CH₂—OCH₃ | —H | —H | —CH₂C≡CH | —Br | 140° C. @ 0.03 mmHg | Cl<br>C<br>H<br>N | 11.91<br>57.79<br>5.82<br>— | 11.93<br>57.62<br>5.90<br>— |
| 47 | 2 | —OCH₂CH₃ | —H | —CH₃ | —CH₂C≡CH | —Br | 124° C. @ 0.05 mmHg | Cl<br>C<br>H<br>N | 11.37<br>60.91<br>6.14<br>— | 11.22<br>60.87<br>6.19<br>— |
| 48 | 2 | —OCH(CH₃)₂ | —H | —CH₃ | —CH₂C≡CH | —Br | 145° C. @ 0.15 mmHg | Cl<br>C<br>H<br>N | 11.99<br>63.06<br>6.80<br>— | 12.01<br>63.10<br>6.87<br>— |
| 49 | 2 | —OCH₂CH₂—OCH₃ | —H | —CH₃ | —CH₂C≡CH | —Br | 150° C. @ 0.2 mmHg | Cl<br>C<br>H<br>N | 10.97<br>60.08<br>6.53<br>— | 10.90<br>59.91<br>6.58<br>— |
| 50 | 2 | —OCH₃ | —H | —CH₃ | —CH₂—C≡N | —Cl | 134° C. @ 0.05 mmHg | Cl<br>C<br>H<br>N | 10.43<br>56.66<br>5.77<br>9.44 | 10.39<br>56.67<br>5.77<br>9.40 |
| 51 | 2 | —OCH₂CH₂OCH₃ | —H | —CH₃ | —CH₂CH=CH₂ | —Br | 148° C. @ 0.1 mmHg | Cl<br>C<br>H<br>N | 11.95<br>59.73<br>7.08<br>— | 11.90<br>59.66<br>7.09<br>— |
| 52 | 1 | —OCH₂CH₂CH₂CH₃ | —H | —CH₃ | —CH₂C≡CH | —Br | 138° C. @ 0.15 mmHg | Cl<br>C<br>H<br>N<br>Cl | 10.37<br>63.05<br>6.85<br>—<br>10.95 | 10.35<br>62.97<br>6.92<br>—<br>10.99 |
| 53 | 1 | [tetrahydrofuranyl-O] | —CF₃ | —H | —CH₂OCH₃ | —Br | 130–150° C. @ 0.04 mmHg | C<br>H<br>N<br>Cl | 50.34<br>5.02<br>3.67<br>9.29 | 50.46<br>5.05<br>3.64<br>9.34 |

(b) Melting Point = 49° C.

EXAMPLE 3

A mixture containing ethyl alcohol (5.75 g; 0.125 mole) and paraformaldehyde (1.86 g; 0.062 mole) in 100 ml. of methylene chloride was cooled to 5° C. To the cooled mixture was added acetyl bromide (7.56 g; 0.062 mole) and the resulting mixture was stirred for 45 minutes. To the resulting mixture was added a mixture containing 2-chloro-[2'-(2-ethoxyethoxy)-6-isopropyl-]acetanilide (4.5 g; 0.015 mole), 1.5 g. of benzyltriethylammonium bromide in 75 ml. of methylene chloride. While maintaining the temperature of the reaction mixture at 15° C., 45 ml. of a 50% solution of sodium hydroxide was added to the reaction mixture and the resulting solution was stirred for 2 hours. To the resulting mixture was added 100 ml. of cold water. The layers were separated and the organic layer was washed with water, dried over magnesium sulfate and concentrated in vacuo to yield a crude product. The crude product was distilled at 128° C. (0.03 mmHg) to yield 2-chloro-[2'-(2-ethoxyethoxy)-6-isopropyl]-N-ethoxymethylacetanilide (4.4 g; 80% yield) as a yellow liquid. The data for Compound No. 55 and other compounds prepared employing a similar procedure is summarized in Table III.

TABLE III $$\text{R}_4\text{-C}_6\text{H}_3(\text{NHC(O)CH}_2\text{Cl})(\text{O(CH}_2)_m\text{R}_2) + \text{R''}-\text{OH} + \text{HCHO} \xrightarrow[\text{PTC; NaOH}]{\text{CH}_3\text{C(O)}-\text{X'}} \text{R}_4\text{-C}_6\text{H}_3(\text{N(CH}_2\text{OR'')C(O)CH}_2\text{Cl})(\text{O(CH}_2)_m\text{R}_2)$$

| Compound Number | m | R₂ | R₄ | R'' | X' | b.p. (°C.) | Element | Calc'd. | Found |
|---|---|---|---|---|---|---|---|---|---|
| 54 | 2 | —OCH₃ | —CH(CH₃)₂ | —CH₂CH₂CH₃ | —Br | 125° C. @ 0.03 mmHg | C<br>H<br>Cl | 60.41<br>7.89<br>9.91 | 60.39<br>7.90<br>9.94 |
| 55 | 2 | —OCH₂CH₃ | —CH(CH₃)₂ | —CH₂CH₃ | —Br | 128° C. @ 0.03 mmHg | C<br>H<br>Cl | 60.41<br>7.89<br>9.91 | 60.36<br>7.91<br>9.92 |
| 56 | 2 | —OCH₃ | —CH₂CH₃ | —CH₂CH₃ | —Br | 125° C. @ 0.03 mmHg | C<br>H<br>Cl | 58.27<br>7.33<br>10.75 | 58.30<br>7.39<br>10.76 |
| 57 | 2 | —OCH₃ | —CH₂CH₃ | —CH(CH₃)₂ | —Br | 127° C. @ 0.04 mmHg | C<br>H<br>Cl | 59.38<br>7.62<br>10.31 | 59.39<br>7.63<br>10.29 |
| 58 | 2 | —OCH₃ | —CH₂CH₃ | —CH₂CH₂CH₃ | —Br | 125° C. @ 0.03 mmHg | C<br>H<br>Cl | 59.38<br>7.62<br>10.31 | 59.40<br>7.63<br>10.30 |
| 59 | 1 | tetrahydrofuryl | —CH₃ | —CH₂CH₃ | —Br | 125° C. @ 0.03 mmHg | C<br>H<br>Cl | 59.73<br>7.08<br>10.37 | 59.69<br>7.11<br>10.34 |
| 60 | 1 | tetrahydrofuryl | —CH₃ | —CH(CH₃)₂ | —Br | 135° C. @ 0.04 mmHg | C<br>H<br>Cl | 60.75<br>7.36<br>9.96 | 60.71<br>7.38<br>9.97 |
| 61 | 2 | —OCH₂CH₃ | —H | —CH₂CH₂CH₃ | — | 124° C. @ 0.03 mmHg | C<br>H<br>Cl | 58.27<br>7.33<br>10.75 | 58.31<br>7.36<br>10.70 |
| 62 | 2 | —OCH₂CH₃ | —H | —CH₂CH(CH₃)₂ | —Br | 131° C. @ 0.02 mmHg | C<br>H<br>Cl | 59.38<br>7.62<br>10.31 | 59.32<br>7.60<br>10.32 |
| 63 | 2 | —OCH₂CH(CH₃)₂ | —CH₃ | —CH₂CH₃ | —Br | 126° C. @ 0.03 mmHg | C<br>H<br>Cl | 60.41<br>7.89<br>9.91 | 60.31<br>7.89<br>9.89 |
| 64 | 2 | —OCH₂CH(CH₃)₂ | —CH₃ | —CH₂CH₂Cl | —Br | 162° C. @ 0.03 mmHg | C<br>H<br>Cl | 55.11<br>6.94<br>18.07 | 55.02<br>6.97<br>18.01 |
| 65 | 2 | —OCH₂CH(CH₃)₂ | —CH₃ | —CH₂CH₂CH₃ | —Br | 143° C. @ 0.03 mmHg | C<br>H<br>Cl | 61.36<br>8.13<br>9.53 | 61.47<br>8.15<br>9.51 |
| 66 | 1 | —O—(CH₂)₂—OCH₃ | —H | —CH₂CH₃ | —Cl | 145° C. @ 0.06 mmHg | C<br>H<br>Cl | 54.30<br>6.68<br>10.69 | 54.31<br>6.67<br>10.63 |
| 67 | 1 | —O—(CH₂)₂—OCH₃ | —H | —CH₃ | —Cl | 140° C. @ 0.07 mmHg | C<br>H<br>Cl | 52.92<br>6.34<br>11.16 | 52.90<br>6.34<br>11.15 |
| 68 | 2 | —O—(CH₂)₂—OCH₃ | —CH₃ | —C₂CH₃ | —Cl | 160° C. @ 0.08 mmHg | C<br>H<br>Cl | 56.71<br>7.28<br>9.85 | 56.81<br>7.32<br>9.88 |
| 69 | 2 | —OCH₂CH₃ | —CH(CH₃)₂ | —CH(CH₃)₂ | —Br | 125° C. @ 0.05 mmHg | C<br>H<br>Cl | 61.36<br>8.13<br>9.53 | 61.28<br>8.17<br>9.52 |

EXAMPLE 4

A mixture containing 2-chloro-[(2-ethoxyethoxy)-6-methyl]acetanilide (5.0 g; 0.018 mole), dimethyl sulfate (2.4 g; 0.019 mole), 1.8 g. of benzyltriethylammonium bromide and 250 ml. of methylene chloride was cooled to 15° C. While maintaining the temperature of the reaction mixture below 15° C., 50 ml. of a 50% solution of sodium hydroxide was added to the reaction mixture and the resultant mixture was stirred for 2 hours. To the reaction mixture was added 100 ml. of cold water. The layers were separated, and the organic methylene dichloride layer was washed with water, dried over magnesium sulfate and concentrated in vacuo to yield a crude product. The crude product was distilled at 135° C. at 0.07 mmHg to yield 2-chloro-[2'-(2-ethoxyethoxy)-6-methyl]-N-methylacetanilide (Compound No. 71) (3.8 g; 72% yield) as a clear oil. The data for Compound No. 71 and other compounds prepared employing a similar procedure is summarized in Table IV.

TABLE IV $$\text{R}_4\text{-}\underset{\underset{\text{O}+\text{CHR}_1\overline{)_m}\text{R}_2}{|}}{\text{C}_6\text{H}_3}\text{-N(H)-C(O)-CH}_2\text{Cl} + (\text{RO})_2\text{SO}_2 \xrightarrow[\text{NaOH}]{\text{PTC}} \text{R}_4\text{-}\underset{\underset{\text{O}+\text{CHR}_1\overline{)_m}\text{R}_2}{|}}{\text{C}_6\text{H}_3}\text{-N(R)-C(O)-CH}_2\text{Cl}$$

| Compound No. | $+CHR_1)_{\overline{m}}R_2$ | $R_4$ | R | b.p. (°C.) | Element | Calc'd. | Found |
|---|---|---|---|---|---|---|---|
| 70 | —(CH$_2$)$_2$—OCH$_3$ | —CH$_3$ | —CH$_3$ | 135° C. @ 0.3 mmHg | C<br>H<br>Cl | 57.46<br>6.68<br>13.05 | 57.48<br>6.73<br>12.99 |
| 71 | —(CH$_2$)$_2$—OCH$_2$CH$_3$ | —CH$_3$ | —CH$_3$ | 135° C. @ 0.07 mmHg | C<br>H<br>Cl | 58.84<br>7.05<br>12.41 | 58.73<br>7.08<br>12.36 |
| 72 | —(CH$_2$)$_2$—OCH$_2$CH$_3$ | —CH$_3$ | —CH$_2$CH$_3$ | 125° C. @ 0.05 mmHg | C<br>H<br>Cl | 60.10<br>7.40<br>11.83 | 59.95<br>7.45<br>11.75 |
| 73 | —(CH$_2$)$_2$—OCH(CH$_3$)$_2$ | —CH$_3$ | —CH$_3$ | 130° C. @ 0.05 mmHg | C<br>H<br>Cl | 60.10<br>7.40<br>11.83 | 60.08<br>7.40<br>11.83 |
| 74 | —(CH$_2$)$_2$—O—CH$_2$CH$_2$CH$_2$CH$_3$ | —CH$_3$ | —CH$_3$ | 143° C. @ 0.07 mmHg | C<br>H<br>Cl | 61.24<br>7.71<br>11.30 | 61.17<br>7.74<br>11.26 |
| 75 | —(CH$_2$)$_2$—O—CH$_2$CH$_2$CH$_2$CH$_3$ | —CH$_3$ | —CH$_2$CH$_3$ | 136° C. @ 0.1 mmHg | C<br>H<br>Cl | 62.28<br>7.99<br>10.81 | 62.24<br>8.02<br>10.83 |
| 76 | —CH(CH$_3$)CH$_2$—O—CH$_3$ | —CH$_3$ | —CH$_3$ | 118° C. @ 0.1 mmHg | C<br>H<br>Cl | 58.84<br>7.05<br>12.41 | 58.79<br>7.06<br>12.40 |
| 77 | —CH(CH$_3$)CH$_2$—O—CH$_3$ | —CH$_3$ | —CH$_2$CH$_3$ | 128° C. @ 0.1 mmHg | C<br>H<br>Cl | 60.10<br>7.40<br>11.83 | 59.87<br>7.47<br>11.76 |
| 78 | —CH$_2$OCH(CH$_3$)$_2$ | —CH$_3$ | —CH$_3$ | 120° C. @ 0.1 mmHg | C<br>H<br>Cl | 58.84<br>7.05<br>12.41 | 58.61<br>7.11<br>12.34 |
| 79 | —(CH$_2$)$_3$—O—C$_6$H$_5$ | —CH$_3$ | —CH$_3$ | 160° C. @ 0.03 mmHg | C<br>H<br>Cl | 65.61<br>6.38<br>10.19 | 65.59<br>6.38<br>10.18 |
| 80 | —(CH$_2$)$_2$—OCH$_3$ | —(CH(CH$_3$)$_2$ | —CH$_3$ | (b) | C<br>H<br>Cl | 60.10<br>7.40<br>11.83 | 60.14<br>7.46<br>11.75 |
| 81 | —CH$_2$-(tetrahydrofuranyl) | —CH$_3$ | —CH$_3$ | 126° C. @ 0.03 mmHg | C<br>H<br>Cl | 60.50<br>6.77<br>11.91 | 60.41<br>6.81<br>11.89 |
| 82 | —(CH$_2$)$_2$—OCH$_2$CH$_3$ | —H | —CH$_3$ | 118° C. @ 0.04 mmHg | C<br>H<br>Cl | 57.46<br>6.68<br>13.05 | 57.45<br>6.69<br>13.07 |
| 83 | —(CH$_2$)$_2$—OCH$_2$CH(CH$_3$)$_2$ | —CH$_3$ | —CH$_3$ | 148° C. @ 0.04 mmHg | C<br>H<br>Cl | 61.24<br>7.71<br>11.30 | 61.17<br>7.73<br>11.27 |
| 84 | —CH$_2$—OCH$_2$CH$_2$—OCH$_3$ | —H | —CH$_3$ | 126° C. @ 0.05 mmHg | C<br>H<br>Cl | 54.26<br>6.31<br>12.32 | 54.03<br>6.34<br>12.28 |
| 85 | —CH$_2$—OCH$_2$CH$_3$ | —CH$_3$ | —CH$_3$ | 125° C. @ 0.07 mmHg | C<br>H<br>Cl | 57.46<br>6.68<br>13.05 | 57.16<br>6.68<br>13.15 |
| 86 | —(CH$_2$)$_2$—OCH$_2$CH$_2$—OCH$_3$ | —CH$_3$ | —CH$_3$ | 148° C. @ 0.2 mmHg | C<br>H<br>Cl | 57.05<br>7.02<br>11.23 | 57.04<br>7.02<br>11.23 |

TABLE IV-continued

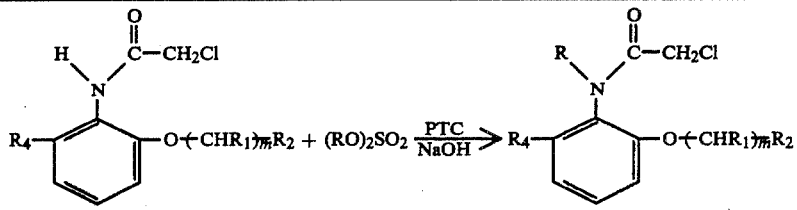

| Compound No. | ${+CHR_1)_{\overline{m}}R_2}$ | $R_4$ | R | b.p. (°C.) | Element | Analysis Calc'd. | Found |
|---|---|---|---|---|---|---|---|
| 87 | —(CH$_2$)$_2$—OCH$_3$ | —CH$_3$ | —CH$_2$CH$_3$ | 133° C. @ 0.15 mmHg | C H Cl | 58.84 7.05 12.41 | 58.77 7.07 12.40 |
| 88 | —CH$_2$OCH$_2$CH$_2$CH$_2$CH$_3$ | —CH$_3$ | —CH$_3$ | 132° C. @ 0.1 mmHg | C H Cl | 60.10 7.40 11.83 | 58.89 7.43 11.93 |
| 89 | —CH$_2$—CH(OCH$_3$)$_2$ | —CH$_3$ | —CH$_3$ | 150° C. @ 0.15 mmHg | C H Cl | 55.72 6.68 11.75 | 55.59 6.69 11.80 |
| 90 | —CH$_2$CH$_2$OCH$_3$ | —CH$_2$CH$_3$ | —CH$_3$ | 130° C. @ 0.02 mmHg | C H Cl | 58.84 7.05 12.41 | 58.73 7.09 12.38 |

(b) Melting Point = 82–82.5° C.

EXAMPLE 5

A mixture containing 2-chloro-[2'-(tetrahydro-2-furanyl)methoxy]-5'-trifluoromethyl-N-methoxymethylacetanilide (3.91 g; 0.0125 mole), 150 ml. of isopropyl alcohol and 0.5 ml. of methane sulfonic acid was refluxed under a Soxhlit extractor for 24 hours. The reaction mixture was concentrated, and the resulting residue was dissolved in methylene chloride. The methylene chloride solution was washed with 5% sodium bicarbonate, dried over magnesium sulfate and concentrated in vacuo to yield a crude product. The crude product was distilled at 130° C. (0.05 mmHg) to yield 2-chloro-[2'-(tetrahydro-2-furanyl)methoxy]-5'-trifluoromethyl-N-[(1-methylethoxy)methyl]acetanilide (Compound No. 92) (3.2 g; 75% yield) as a yellow oil. The data for Compound No. 92 and other compounds prepared using a similar procedure is summarized in Table V.

TABLE V

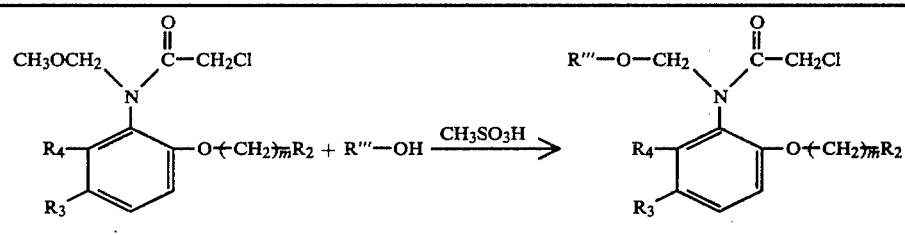

| Compound No. | R''' | m | R$_2$ | R$_3$ | R$_4$ | b.p. (°C.) | Carbon Cal'd | Found | Hydrogen Cal'd | Found | Nitrogen Cal'd | Found | Chlorine Cal'd | Found |
|---|---|---|---|---|---|---|---|---|---|---|---|---|---|---|
| 91 | —CH$_2$CH$_2$CH$_3$ | 1 | (tetrahydrofuranyl) | —CF$_3$ | —H | 140° @ 0.07 mmHg | 53.01 | 53.09 | 5.19 | 5.23 | 3.43 | 3.40 | 8.69 | 8.74 |
| 92 | —CH(CH$_3$)$_2$ | 1 | (tetrahydrofuranyl) | —CF$_3$ | —H | 140° @ 0.07 mmHg | 52.75 | 52.66 | 5.66 | 5.68 | 3.42 | 3.42 | 8.65 | 8.75 |
| 93 | —CH(CH$_3$)$_2$ | 1 | (tetrahydrofuranyl) | —H | —H | 130° @ 0.05 mmHg | 59.73 | 59.56 | 7.08 | 7.10 | 4.10 | 4.08 | 10.37 | 10.36 |
| 94 | —CH$_2$CH=CH$_2$ | 1 | (tetrahydrofuranyl) | —H | —H | 15° @ 0.07 mmHg | 60.09 | 59.91 | 6.53 | 6.63 | 4.12 | 4.08 | 10.43 | 10.37 |
| 95 | —CH$_2$CH=CH$_2$ | 2 | —OCH$_3$ | —H | —CH$_3$ | 140° @ 0.03 mmHg | 58.62 | 58.53 | 6.76 | 6.79 | 4.27 | 4.24 | 10.82 | 10.76 |
| 96 | —CH$_2$CH$_2$OCH$_3$ | 2 | —OCH$_3$ | —H | —H | 155° @ 0.09 mmHg | 54.30 | 54.26 | 6.68 | 6.69 | 4.22 | 4.23 | 10.69 | 10.68 |

TABLE V-continued

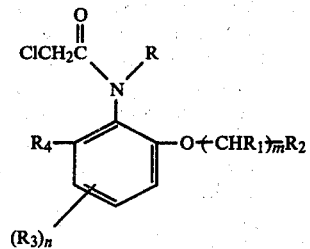

| Compound No. | R''' | m | R₂ | R₃ | R₄ | b.p. (°C.) | Carbon Cal'd | Carbon Found | Hydrogen Cal'd | Hydrogen Found | Nitrogen Cal'd | Nitrogen Found | Chlorine Cal'd | Chlorine Found |
|---|---|---|---|---|---|---|---|---|---|---|---|---|---|---|
| 97 | $-\text{CHCH}_2\text{CH}_3$ (CH₃) | 2 | $-\text{OCH}_3$ | $-\text{H}$ | $-\text{H}$ | 140° @ 0.09 mmHg | 58.27 | 58.08 | 7.33 | 7.32 | 4.25 | 4.25 | 10.75 | 10.85 |
| 98 | $-\text{CH}_2\text{CH}_2\text{CH}_2-\text{CN}$ | 1 | (tetrahydrofuranyl) | $-\text{H}$ | $-\text{H}$ | 160° @ 0.05 mmHg | 60.75 | 60.74 | 7.36 | 7.37 | 3.94 | 3.94 | 9.96 | 9.96 |
| 99 | $-\text{CH}(\text{CH}_3)_2$ | 2 | $-\text{OCH}_3$ | $-\text{H}$ | $-\text{CH}_3$ | 142° @ 0.07 mmHg | 58.27 | 58.09 | 7.33 | 7.34 | 4.25 | 4.26 | 10.75 | 10.79 |
| 100 | $-\text{CH}_2\text{CH}=\text{CH}_2$ | 2 | $-\text{OCH}_3$ | $-\text{H}$ | $-\text{H}$ | 135° @ 0.03 mmHg | 57.42 | 57.52 | 6.42 | 6.45 | 4.46 | 4.42 | 11.30 | 11.29 |
| 101 | $-\text{CH}(\text{CH}_3)_2$ | 2 | $-\text{OCH}_3$ | $-\text{H}$ | $-\text{H}$ | 134° @ 0.04 mmHg | 57.05 | 56.76 | 7.02 | 6.94 | 4.44 | 4.58 | 11.23 | 11.35 |

EXAMPLE 6

To 100 ml of toluene was added 4.2 g (0.0126 mol) of 2-chloro-[2'-(2-isopropoxyethoxy)-6'-methyl]-N-chloromethyl acetanilide and 1.7 g (0.0252 mol) of pyrazole; this mixture was heated at 80° C. for 8 hours, then cooled. The organic layer was separated and washed with 10% HCl and water, then dried over MgSO₄, evaporated and purified by chromatography (3/2(C₂H₅)₂O/hexane). There was obtained 2.2 g (48% yield) of a yellow oil.

| Anal: Calc'd for $C_{18}H_{24}ClN_3O_3$ (wt %) | | |
|---|---|---|
| Element | Theory | Found |
| C | 59.09 | 58.45 |
| H | 6.61 | 6.72 |
| Cl | 9.69 | 9.95 |
| N | 11.48 | 11.36 |

The product was identified as 2-chloro-[2'-(2-isopropoxyethoxy)-6'-methyl]-N-(pyrazolylmethyl)acetanilide.

The N-chloromethyl acetanilide starting material used in Example 6 is readily prepared by conventional processes known to the art, including the halogenation of the corresponding N-alkoxymethyl acetanilide with hydrogen halide or a thionyl halide or by the haloacetylation of the appropriately substituted phenylazomethine.

Following the same procedures described above, the additional species shown in Table VI were also prepared and tested. Compound Nos. 102–106 were prepared according to the process of Example 2; Compound Nos. 107–109 were prepared according to the processes of Examples 1, 4 and 6, respectively.

TABLE VI

| Compound No. | R | $-(\text{CHR}_1)_m-$ | R₂ | R₃ | R₄ | b.p. °C. (mm Hg) | Element | Cal'd | Found |
|---|---|---|---|---|---|---|---|---|---|
| 102 | $-\text{i-C}_3\text{H}_7$ | $-(\text{CH}_2\text{CH}_2\text{O})_2-$ | $-\text{CH}_3$ | H | $-\text{CH}_3$ | 163 (0.13) | C | 59.38 | 59.30 |
|  |  |  |  |  |  |  | H | 7.62 | 7.63 |
|  |  |  |  |  |  |  | Cl | 10.31 | 10.27 |
| 103 | $-\text{allyl}$ | $-\text{CH}_2\text{CH}_2\text{O}-$ | $-\text{i-C}_3\text{H}_7$ | H | $-\text{CH}_3$ | 137 (0.05) | C | 62.66 | 62.62 |
|  |  |  |  |  |  |  | H | 7.42 | 7.49 |
|  |  |  |  |  |  |  | Cl | 10.88 | 10.82 |
| 104 | $-\text{CH}_2\text{OC}_3\text{H}_7$ | $-\text{CH}_2\text{CH}_2\text{O}$ | $-\text{CH}_3$ | $-\text{CH}_3$ | $-\text{CH}_3$ | 154 | C | 59.38 | 59.29 |

TABLE VI-continued

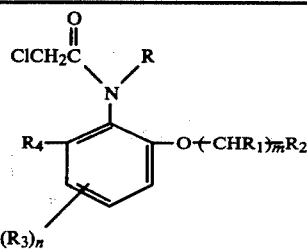

| Compound No. | R | —(CHR₁)ₘ | R₂ | R₃ | R₄ | b.p. °C. (mm Hg) | Element | Cal'd | Found |
|---|---|---|---|---|---|---|---|---|---|
| | | | | | | (0.08) | H | 7.62 | 7.65 |
| | | | | | | | Cl | 10.31 | 10.28 |
| 105 | —CH₂OC₃H₇ | —CH₂ | —CH(OCH₃)₂ | H | —CH₃ | yellow oil | C | 56.74 | 56.68 |
| | | | | | | | H | 7.23 | 7.27 |
| | | | | | | | Cl | 9.87 | 9.81 |
| 106 | —CH₂OC₂H₅ | —CH₂CH₂O— | —C₂H₅ | —H | —Cl | 133 (0.1) | C | 51.44 | 51.38 |
| | | | | | | | H | 6.04 | 6.08 |
| | | | | | | | Cl | 20.24 | 20.21 |
| 107 | —H | —CH₂CH₂OO | —CH₃ | —CH₃ | —CH₃ | m.p. 132 | C | 57.46 | 57.48 |
| | | | | | | | H | 6.68 | 6.72 |
| | | | | | | | Cl | 13.05 | 22.99 |
| 108 | —CH₃ | —CH₂CH₂O— | —CH₃ | —CH₃ | —CH₃ | 154 (0.07) | C | 58.84 | 58.65 |
| | | | | | | | H | 7.04 | 7.10 |
| | | | | | | | Cl | 12.41 | 12.32 |
| 109 | —CH₂—N⟨N= | —CH₂CH₂O— | —i-C₃H₇ | —H | —CH₃ | yellow oil | C | 59.09 | 58.45 |
| | | | | | | | H | 6.61 | 6.72 |
| | | | | | | | Cl | 9.69 | 9.95 |
| | | | | | | | N | 11.48 | 11.36 |

In Example 7 are shown processes for preparing raw materials used in various processes used to prepare products according to this invention as described in preceding examples. Thus, in paragraph (a) of Example 7 is described the preparation of a typical o-polyalkoxy-o-alkyl nitrobenzene which in paragraph (b) is reduced to the corresponding aniline, which in paragraph (c) is alkylated to form an N-alkylated procuct, which, in turn, may be haloacetylated to obtain the corresponding 2-haloacetanilide as shown in paragraph (d).

EXAMPLE 7

(a) A mixture containing 3-methyl-2-nitrophenol (30.6 g; 0.2 mole), 2-(2-methoxy)ethoxybromoethane (40.2 g; 0.22 mole) and potassium carbonate (30.5 g; 0.22 mole) in 300 ml. of dimethyl formamide was refluxed for 24 hours. The reaction mixture was cooled to 26° C. and then 200 ml. of water was added to the reaction mixture. The resulting mixture was extracted into methylene chloride and the organic methylene chloride layer was washed with sodium hydroxide, then water, dried over magnesium sulfate and concentrated in vacuo to yield an oil residue. The residue was distilled at 127° C. (0.07 mmHg) to yield 45.3 g of 1-[2-(2-methoxyethoxy)ethoxy]-3-methyl-2-nitrobenzene as a yellow oil.

(b) A mixture containing a portion of the 1-[2-(2-methoxyethoxy)ethoxy]-3-methyl-2-nitrobenzene (44.2 g; 0.173 mole) in 15 ml. of ethanol and 15 ml. of acetic acid was heated to 60° C. To the reaction mixture was added 1 g. of a 5% palladium on charcoal catalyst and the resultant mixture was hydrogenated at 60° C. for 24 hours. The reaction mixture was then filtered to remove the catalyst and then concentrated to yield 39 g. of 6-methyl-2-[2-(2-methoxyethoxy)ethoxy]aniline.

(c) A mixture containing a portion of the 6-methyl-2-[2-(2-methoxyethoxy)ethoxy]aniline (11.25 g; 0.05 mole) in 10 ml. of ethanol and 10 ml. of ethyl acetate was heated to 50° C. To this reaction mixture was added 10 ml. of acetone and 0.5 g. platinum (IV) oxide catalyst and the resulting mixture was hydrogenated at 60° C. for 4 hours. The reaction mixture was filtered through clay to remove any catalyst and then concentrated in vacuo to yield 8.6 g. of 6-methyl-2-[2-(2-methoxyethoxy)ethoxy]-N-2-methylethylaniline.

(d) A mixture containing a portion of the 6-methyl-2-[2-(2-methoxyethoxy)ethoxy]-N-2-methylethyl aniline (5.34 g; 0.02 mole) and sodium hydroxide (0.88 g; 0.22 mole) in 150 ml. of methylene chloride was cooled to 10° C. To the reaction mixture was added dropwise chloroacetyl chloride (2.5 g; 0.022 mole) and the resulting mixture was stirred for 10 minutes. The layers were separated and the organic methylene chloride layer was washed with water, dried over magnesium sulfate and concentrated in vacuo to yield a crude product. The crude product was separated on a silica gel column using a 2:5 ethyl acetate:cyclohexane mixture as the eluant to yield 2-chloro-N-2-methylethyl-N-[6-methyl-2-(2-(2-methoxyethoxy)ethoxy)phenyl]acetamide (Compound No. 102) (2.7 g; 39% yield) as a clear yellow oil having a boiling point of 163° C. (0.13 mmHg) and the following analysis:

Calculated: C, 59.38; H, 7.62; Cl, 10.31. Found: C, 59.30; H, 7.63; Cl, 10.27.

EXAMPLE 8

The post-emergence herbicidal activity of various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed in a mixture comprising 35 weight percent butylamine dodecylbenzene sulfonate and 65 weight percent of a tall oil ethylene oxide condensate having 11 moles of ethylene oxide per mole of tall oil. The pans are returned to the greenhouse and watered as before and the injury to the plants as compared to the control is observed at approximately two weeks and is indicated in the tables under WAT and the results recorded.

The post-emergence herbicidal activity index used in Tables VII and VIII is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

TABLE VII

| Compound Number | WAT | kg/h | A | B | C | D | E | F | G | H | I | J | K |
|---|---|---|---|---|---|---|---|---|---|---|---|---|---|
| 1 | 2 | 11.2 | 0 | 0 | 1 | 3 | 1 | 0 | 0 | 0 | 0 | 0 | 1 |
| 2 | 2 | 11.2 | 1 | 2 | 2 | 2 | 3 | 3 | — | 0 | 0 | 1 | 2 |
| 3 | 2 | 11.2 | — | 0 | 0 | 0 | 0 | 0 | 0 | 0 | 0 | 0 | 1 |
| 4 | 2 | 11.2 | 0 | 0 | 0 | — | 0 | 0 | 0 | 0 | 0 | 0 | 0 |
| 5 | 2 | 11.2 | 0 | 1 | 0 | 0 | 1 | 0 | 0 | 0 | 0 | 0 | 1 |
| 6 | 2 | 11.2 | 0 | 1 | 1 | 1 | 2 | 2 | 0 | 0 | 0 | 0 | 2 |
| 7 | 2 | 11.2 | 0 | 0 | 0 | 1 | 0 | 3 | 1 | 0 | 0 | 0 | 0 |
| 8 | 2 | 11.2 | 0 | 0 | 1 | 0 | 2 | 1 | 0 | 0 | 0 | 0 | 0 |
| 9 | 2 | 11.2 | 0 | 0 | 0 | 0 | 0 | 1 | — | 0 | 0 | 0 | 0 |
| 10 | 2 | 11.2 | 0 | 0 | 0 | 1 | 0 | 0 | 0 | 0 | 0 | 0 | 1 |
| 11 | 2 | 11.2 | 2 | 0 | 0 | 0 | 0 | 0 | 0 | 0 | 0 | 0 | 0 |
| 12 | 2 | 11.2 | 0 | 0 | 0 | 0 | 0 | 0 | 0 | 0 | 0 | 0 | 0 |
| 13 | 2 | 11.2 | 0 | 1 | 0 | 0 | 0 | 0 | 0 | 0 | 0 | 0 | 0 |
| 14 | 2 | 11.2 | 0 | 0 | 0 | 0 | 0 | 0 | — | 0 | 0 | 0 | 0 |
| 15 | 2 | 11.2 | 1 | 0 | 0 | 1 | 1 | — | 0 | 0 | 0 | 0 | 0 |
| 16 | 2 | 11.2 | 0 | 0 | 0 | 1 | 0 | 0 | 0 | 0 | 0 | 0 | 0 |
| 17 | 2 | 11.2 | 0 | 0 | 0 | 0 | 3 | 0 | 0 | 0 | 0 | 0 | 1 |
| 18 | 2 | 11.2 | 0 | 0 | 0 | 1 | 2 | 0 | — | 0 | 0 | 0 | 2 |
| 19 | 2 | 11.2 | 0 | 1 | 0 | 1 | 1 | 1 | 1 | 0 | 0 | 0 | 2 |
| 20 | 2 | 11.2 | — | 1 | 0 | 2 | 2 | 0 | 0 | 0 | 0 | 0 | 1 |
| 21 | 2 | 11.2 | 0 | 1 | 1 | 2 | 1 | 0 | 1 | 1 | 0 | 0 | 3 |
| 22 | 2 | 11.2 | 0 | 1 | 0 | 2 | 0 | 0 | 1 | 0 | 0 | 0 | 2 |
| 23 | 2 | 11.2 | 0 | 1 | 0 | 1 | 0 | 0 | 2 | 0 | 0 | 0 | 2 |
| 24 | 2 | 11.2 | 0 | 0 | 0 | 1 | 1 | 0 | 0 | 0 | 0 | 0 | 1 |
| 25 | 2 | 11.2 | 0 | 1 | 0 | 0 | 1 | 0 | 0 | 0 | 0 | 0 | 2 |
| 26 | 2 | 11.2 | — | 0 | 0 | 0 | 0 | 0 | 0 | 0 | 0 | 0 | 0 |
| 27 | 2 | 11.2 | 0 | 2 | 1 | 2 | 0 | 1 | 1 | 0 | 1 | 0 | 2 |
| 28 | 2 | 11.2 | — | 1 | 1 | 0 | 1 | 0 | 0 | 0 | 0 | 0 | 2 |
| 29 | 2 | 11.2 | — | 0 | 0 | — | 0 | 0 | 1 | 0 | 1 | 0 | 2 |
| 30 | 2 | 11.2 | — | 0 | 0 | 0 | — | 1 | 1 | 0 | 1 | 1 | 2 |
| 31 | 2 | 11.2 | 0 | 1 | 0 | 1 | — | 0 | 0 | 0 | 2 | 0 | 2 |
| 32 | 2 | 11.2 | 0 | 0 | 1 | 0 | 0 | 0 | 0 | 0 | 0 | 0 | 0 |
| 33 | 2 | 11.2 | — | 1 | 1 | 2 | 0 | 0 | 1 | 0 | 0 | 0 | 2 |
| 34 | 2 | 11.2 | — | 0 | 1 | 0 | 0 | 2 | 0 | 0 | 0 | 0 | 1 |
| 35 | 2 | 11.2 | 1 | 1 | 1 | 1 | 4 | 3 | 0 | 0 | 0 | 0 | 1 |
| 36 | 2 | 11.2 | 0 | 0 | 0 | 0 | 0 | 0 | 0 | 0 | 0 | 0 | 1 |
| 37 | 2 | 11.2 | 0 | 1 | 1 | 2 | 1 | 1 | 1 | 0 | 1 | 0 | 1 |
| 38 | 2 | 11.2 | 0 | 1 | 0 | 1 | 1 | 0 | 1 | 1 | 1 | 0 | 1 |
| 39 | 2 | 11.2 | — | 1 | 0 | — | 1 | 1 | 1 | 1 | 0 | 0 | 2 |
| 40 | 2 | 11.2 | 0 | 1 | 1 | 1 | 2 | 2 | 1 | 0 | 1 | 0 | 2 |
| 41 | 2 | 11.2 | 0 | 1 | 1 | 2 | 4 | 3 | 1 | 0 | 1 | 1 | 2 |
| 42 | 2 | 11.2 | 0 | 1 | 0 | 1 | 0 | 0 | 1 | 0 | 0 | 0 | 2 |
| 43 | 2 | 11.2 | 1 | 1 | 0 | — | 3 | 2 | 1 | 0 | 0 | 0 | 2 |
| 44 | 2 | 11.2 | 0 | 1 | 0 | 2 | 0 | 1 | 0 | 0 | 1 | 0 | 1 |
| 45 | 2 | 11.2 | 0 | 2 | 0 | 1 | 1 | 0 | 0 | 0 | 0 | 0 | 2 |
| 46 | 2 | 11.2 | — | 0 | 0 | 0 | 0 | 0 | 0 | 0 | 0 | 0 | 1 |
| 47 | 2 | 11.2 | 1 | 1 | 1 | 2 | 3 | 1 | 1 | 0 | 0 | 0 | 2 |
| 48 | 2 | 11.2 | 0 | 1 | 1 | 1 | 1 | — | 2 | 0 | 0 | 0 | 1 |
| 49 | 2 | 11.2 | 0 | 2 | 0 | 2 | 1 | 2 | 1 | 0 | 0 | 0 | 2 |
| 50 | 2 | 11.2 | 0 | 2 | 0 | 1 | 1 | 2 | 1 | 0 | 0 | 0 | 2 |
| 51 | 2 | 11.2 | 0 | 1 | 0 | 0 | 1 | — | 1 | 0 | 0 | 0 | 2 |
| 52 | 2 | 11.2 | — | 1 | 1 | 2 | 3 | 1 | 1 | 0 | 1 | 0 | 2 |
| 53 | 2 | 11.2 | 0 | 0 | 0 | 0 | 0 | 0 | 0 | 0 | 0 | 0 | 0 |
| 54 | 2 | 11.2 | 0 | 1 | 1 | 2 | 1 | 1 | 1 | 0 | 0 | 1 | 2 |
| 55 | 2 | 11.2 | 1 | 2 | 1 | 3 | 2 | 2 | 1 | 1 | 0 | 1 | 3 |
| 56 | 2 | 11.2 | 0 | 2 | 0 | 3 | 2 | 1 | 2 | 2 | 0 | 1 | 2 |
| 57 | 2 | 11.2 | 0 | 2 | 0 | 2 | 1 | 1 | 1 | 0 | 0 | 0 | 2 |
| 58 | 2 | 11.2 | 1 | 0 | 1 | 2 | 3 | 1 | 2 | 2 | 0 | 1 | 2 |
| 59 | 2 | 11.2 | 1 | 1 | 0 | 2 | 1 | 1 | 1 | 0 | 0 | 0 | 2 |
| 60 | 2 | 11.2 | 0 | 1 | 0 | 1 | 1 | 0 | 0 | 0 | — | 0 | 1 |
| 61 | 2 | 11.2 | 0 | 1 | 0 | 1 | 1 | 1 | 1 | 0 | 0 | 0 | 2 |
| 62 | 2 | 11.2 | 0 | 0 | 0 | 0 | 1 | 0 | 0 | 0 | 0 | 0 | 3 |
| 63 | 2 | 11.2 | 0 | 0 | 0 | 1 | 1 | 1 | — | 0 | 0 | 0 | 1 |
| 64 | 2 | 11.2 | 0 | 0 | 0 | 0 | 0 | 0 | — | 0 | 0 | 0 | 1 |
| 65 | 2 | 11.2 | 1 | 0 | 0 | 1 | 0 | 0 | 0 | — | 0 | 0 | 1 |
| 66 | 2 | 11.2 | — | 1 | 0 | 0 | 0 | 1 | 1 | 1 | 0 | 0 | 1 |
| 67 | 2 | 11.2 | — | 1 | 0 | 1 | 0 | 0 | 0 | 0 | 0 | 0 | 0 |
| 68 | 2 | 11.2 | 1 | 1 | 0 | 2 | 2 | 1 | 0 | 0 | — | 0 | 1 |
| 69 | 2 | 11.2 | 0 | 0 | 0 | 1 | 0 | 0 | 0 | 0 | 0 | 0 | 0 |
| 70 | 2 | 11.2 | 0 | 1 | 1 | 0 | 1 | 0 | 0 | 0 | 0 | 0 | 2 |
| 71 | 2 | 11.2 | — | 2 | 1 | 2 | 2 | 0 | 1 | 1 | 1 | 0 | 2 |
| 72 | 2 | 11.2 | 1 | 1 | 1 | 1 | 0 | 1 | 0 | 0 | 0 | 0 | 2 |
| 73 | 2 | 11.2 | 1 | 1 | 1 | 2 | 3 | 2 | 0 | 0 | 0 | 0 | 1 |
| 74 | 2 | 11.2 | 0 | 1 | 0 | 0 | 0 | 1 | 0 | 0 | 0 | 0 | 1 |
| 75 | 2 | 11.2 | 0 | 1 | 1 | 1 | 1 | 0 | 0 | 0 | 0 | 0 | 1 |
| 76 | 2 | 11.2 | 0 | 1 | 1 | 2 | 2 | 2 | 0 | 0 | 0 | 0 | 1 |
| 77 | 2 | 11.2 | 1 | 0 | 2 | 1 | 2 | 1 | 0 | 0 | 0 | 0 | 1 |
| 78 | 2 | 11.2 | 0 | 1 | 1 | 2 | 3 | 1 | 0 | 0 | 0 | 0 | 2 |
| 79 | 2 | 11.2 | 0 | 1 | 0 | 1 | 1 | 0 | 0 | 0 | 0 | 0 | 1 |
| 80 | 2 | 11.2 | 0 | 2 | 2 | 2 | 1 | 2 | 1 | 1 | 0 | 0 | 2 |
| 81 | 2 | 11.2 | 1 | 1 | 1 | 1 | 3 | 1 | — | 0 | 0 | 0 | 2 |
| 82 | 2 | 11.2 | 0 | 2 | 1 | 1 | 1 | 0 | 0 | 0 | 0 | 0 | 1 |
| 83 | 2 | 11.2 | 0 | 1 | 0 | 1 | 1 | 0 | — | 0 | 0 | 0 | 0 |
| 84 | 2 | 11.2 | — | 1 | 0 | 0 | 0 | 0 | 0 | 0 | 0 | 0 | 0 |
| 85 | 2 | 11.2 | 0 | 1 | 0 | 1 | 1 | — | 2 | 0 | 0 | 0 | 1 |

TABLE VII-continued

| Compound Number | WAT | kg/h | A | B | C | D | E | F | G | H | I | J | K |
|---|---|---|---|---|---|---|---|---|---|---|---|---|---|
| 86 | 2 | 11.2 | 0 | 1 | 0 | 2 | 2 | 2 | 1 | 0 | 0 | 0 | 2 |
| 87 | 2 | 11.2 | 1 | 2 | 1 | 2 | 3 | 1 | 1 | 0 | 0 | 0 | 2 |
| 88 | 2 | 11.2 | 0 | 2 | 0 | 2 | 1 | — | 1 | 0 | 0 | 0 | 2 |
| 89 | 2 | 11.2 | 1 | 1 | 1 | 2 | 0 | — | 1 | 0 | 0 | 0 | 2 |
| 90 | 2 | 11.2 | 1 | 1 | 0 | 3 | 2 | 1 | 2 | 1 | 0 | 1 | 2 |
| 91 | 2 | 11.2 | 0 | — | 0 | 0 | 1 | 0 | 0 | 0 | 0 | 0 | 1 |
| 92 | 2 | 11.2 | 0 | — | 0 | 0 | 0 | 0 | 0 | 0 | 0 | 0 | 0 |
| 93 | 2 | 11.2 | 1 | 2 | 0 | 1 | 2 | 0 | 1 | 0 | 0 | 0 | 1 |
| 94 | 2 | 11.2 | 0 | 1 | 0 | 1 | 2 | 0 | 0 | 0 | 0 | 1 | 1 |
| 95 | 2 | 11.2 | 0 | 1 | 0 | 1 | 0 | 0 | — | 1 | 0 | 1 | 3 |
| 96 | 2 | 11.2 | 0 | 1 | 0 | 1 | 2 | 0 | 0 | 0 | 0 | 0 | 2 |
| 97 | 2 | 11.2 | 0 | 1 | 0 | 1 | 0 | 0 | 0 | 0 | 1 | 0 | 1 |
| 98 | 2 | 11.2 | 0 | 0 | 0 | 0 | 0 | 0 | 0 | 0 | 0 | 0 | 1 |
| 99 | 2 | 11.2 | 1 | 2 | 1 | 1 | 1 | 1 | — | 1 | 1 | 1 | — |
| 100 | 2 | 11.2 | 0 | 1 | 0 | 1 | 3 | 0 | 0 | 0 | 0 | 0 | 2 |
| 101 | 2 | 11.2 | 0 | 1 | 0 | 1 | 1 | 0 | 0 | 0 | 0 | 0 | 1 |
| 102 | 2 | 11.2 | 0 | 1 | 1 | 1 | 2 | 0 | 0 | 0 | 0 | 0 | 2 |

TABLE VIII

| Compound No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 2 | 5.6 | 1 | 0 | 0 | 0 | 0 | 0 | 1 | 2 | 0 | 2 | 1 | 1 | 0 | 0 | 2 | 2 |
| 1 | 2 | 1.12 | 1 | 0 | 0 | 0 | 0 | 0 | 0 | 2 | 0 | 1 | 0 | 0 | 0 | 0 | 0 | 0 |
| 2 | 2 | 5.6 | 1 | 1 | 0 | 0 | 1 | 0 | 1 | 1 | — | 4 | 1 | 0 | 0 | 1 | 0 | 1 |
| 2 | 2 | 1.12 | 1 | 0 | 0 | 0 | 0 | 0 | 0 | 0 | 0 | 1 | 0 | 0 | 0 | 0 | 0 | 0 |
| 7 | 2 | 5.6 | 1 | 0 | 0 | 0 | 0 | 0 | 0 | 1 | — | — | 0 | 0 | 0 | 0 | 0 | 0 |
| 7 | 2 | 1.12 | 0 | 0 | 0 | 0 | 0 | 0 | 0 | 0 | 0 | 0 | 0 | 0 | 0 | 0 | 0 | 0 |
| 35 | 2 | 5.6 | 1 | 1 | 0 | 1 | 1 | 1 | 2 | 1 | 1 | 4 | 2 | 0 | 0 | 1 | 2 | 2 |
| 35 | 2 | 1.12 | 0 | 0 | 0 | 0 | 0 | 0 | 0 | 0 | 0 | 2 | 0 | 0 | 0 | 0 | 2 | 2 |
| 41 | 2 | 5.6 | 1 | 1 | 1 | 0 | 1 | 2 | 2 | 2 | 1 | — | 2 | 1 | 1 | 1 | 1 | 1 |
| 41 | 2 | 1.12 | 1 | 0 | 0 | 0 | 1 | 1 | 1 | 2 | 0 | 0 | 0 | 0 | 0 | 0 | 1 | 1 |
| 55 | 2 | 5.6 | 2 | 0 | 0 | 0 | 1 | 0 | 1 | 2 | 3 | 1 | 3 | 1 | 0 | 1 | 2 | 1 |
| 55 | 2 | 1.12 | 0 | 0 | 0 | 0 | 0 | 0 | 0 | 0 | 0 | 0 | 0 | 0 | 0 | 0 | 0 | 0 |
| 56 | 2 | 5.6 | 2 | 1 | 1 | 1 | 1 | 1 | 1 | 2 | 4 | 2 | 2 | 0 | 0 | 1 | 2 | 2 |
| 56 | 2 | 1.12 | 1 | 0 | 0 | 0 | 0 | 0 | 0 | 1 | 3 | 3 | 2 | 0 | 0 | 1 | 1 | 1 |
| 62 | 2 | 5.6 | 0 | 0 | 0 | 2 | 1 | 1 | 0 | 0 | — | 1 | 1 | 0 | 0 | 1 | 2 | — |
| 62 | 2 | 1.12 | 0 | 0 | 0 | 0 | 0 | 0 | 0 | 0 | 1 | 0 | 1 | 0 | 0 | 1 | 1 | — |
| 90 | 2 | 5.6 | 2 | 1 | 0 | 0 | 1 | 1 | 2 | 2 | 4 | 3 | 3 | 1 | 1 | 1 | 3 | 2 |
| 90 | 2 | 1.12 | 1 | 0 | 0 | 0 | 0 | 0 | 1 | 0 | 3 | 1 | 0 | 0 | 0 | 0 | 2 | 2 |
| 95 | 2 | 5.6 | 1 | — | 1 | 1 | 1 | 1 | 1 | 2 | 0 | — | 2 | 0 | 1 | 1 | 2 | 3 |
| 95 | 2 | 1.12 | 1 | 0 | 1 | 1 | 1 | 1 | 1 | 1 | — | 0 | 0 | 0 | 0 | 0 | 1 | 1 |

EXAMPLE 9

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Tables IX and X.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the table are identified by the same code letters used in the previous example.

TABLE IX

| Compound Number | WAT | kg/h | A | B | C | D | E | F | G | H | I | J | K |
|---|---|---|---|---|---|---|---|---|---|---|---|---|---|
| 1 | 2 | 11.2 | 0 | 0 | 2 | 2 | 3 | 1 | 0 | 0 | 0 | 3 | 3 |
| 1 | 2 | 5.6 | 0 | 0 | 2 | 2 | 3 | 1 | 0 | 0 | 0 | 1 | 3 |
| 2 | 2 | 11.2 | 0 | 0 | 0 | 0 | 2 | 0 | 0 | 0 | 0 | 0 | 0 |
| 2 | 2 | 5.6 | 0 | 0 | 0 | 0 | 0 | 0 | 0 | 0 | 0 | 0 | 0 |
| 3 | 2 | 11.2 | 1 | 0 | 1 | 2 | 3 | 1 | 1 | 0 | 0 | 0 | 3 |
| 3 | 2 | 5.6 | 2 | 0 | 0 | 0 | 3 | 0 | 2 | 0 | 0 | 1 | 2 |
| 4 | 2 | 11.2 | 0 | 0 | 0 | 0 | 3 | 0 | 0 | 0 | 0 | 0 | 3 |
| 4 | 2 | 5.6 | 0 | 0 | 0 | 0 | 3 | 0 | 0 | 0 | 0 | 0 | 3 |
| 5 | 2 | 11.2 | 1 | 0 | 3 | 1 | 3 | 1 | 1 | 0 | 0 | 0 | 3 |
| 5 | 2 | 5.6 | 1 | 0 | 3 | 0 | 3 | 1 | 1 | 0 | 0 | 0 | 3 |
| 6 | 2 | 11.2 | 0 | 0 | 2 | 2 | 3 | 1 | 3 | 3 | 3 | 3 | 3 |
| 6 | 2 | 5.6 | 0 | 0 | 2 | 3 | 2 | 2 | 2 | 2 | 2 | 2 | 3 |
| 7 | 2 | 11.2 | 0 | 0 | 1 | 1 | 3 | 0 | 3 | 1 | 3 | 0 | 3 |
| 7 | 2 | 5.6 | 0 | 0 | 0 | 2 | 2 | 0 | 0 | 0 | 0 | 0 | 2 |
| 8 | 2 | 11.2 | 1 | 0 | 0 | 0 | 1 | 0 | 1 | 0 | 0 | 1 | 1 |
| 8 | 2 | 5.6 | 0 | 0 | 0 | 0 | 0 | 0 | 0 | 0 | 0 | 0 | 2 |
| 9 | 2 | 11.2 | 3 | 0 | 0 | 0 | 0 | 0 | — | 0 | 0 | 0 | 0 |
| 9 | 2 | 5.6 | 0 | 0 | 0 | 0 | 0 | 0 | — | 0 | 0 | 0 | 0 |
| 10 | 2 | 11.2 | 2 | 0 | 0 | 3 | 2 | 0 | 0 | 0 | 0 | 0 | 1 |
| 10 | 2 | 5.6 | 0 | 0 | 0 | 2 | 3 | 0 | 0 | 0 | 0 | 1 | 3 |
| 11 | 2 | 11.2 | 0 | 0 | 0 | 0 | 0 | 0 | 0 | 0 | 0 | 0 | 0 |
| 11 | 2 | 5.6 | 0 | 0 | 0 | 0 | 0 | 0 | 0 | 0 | 0 | 0 | 0 |
| 12 | 2 | 11.2 | 0 | 0 | 0 | 0 | 0 | 0 | 0 | 0 | 0 | 0 | 1 |
| 12 | 2 | 5.6 | 0 | 0 | 0 | 0 | 0 | 0 | 0 | 0 | 0 | 0 | 0 |
| 13 | 2 | 11.2 | 0 | 0 | 0 | 0 | 3 | 0 | 0 | 0 | 3 | 2 | 3 |
| 13 | 2 | 5.6 | 0 | 0 | 0 | 0 | 0 | 0 | 0 | 0 | 0 | 0 | 0 |
| 14 | 2 | 11.2 | 0 | 0 | 0 | 0 | 3 | 0 | 0 | 0 | 0 | 2 | 3 |
| 14 | 2 | 5.6 | 0 | 0 | 0 | 0 | 3 | 0 | 0 | 0 | 0 | 0 | 3 |
| 15 | 2 | 11.2 | 0 | 0 | 0 | 0 | 1 | 1 | 0 | 0 | 0 | 0 | 0 |
| 15 | 2 | 5.6 | 0 | 0 | 0 | 0 | 2 | — | 0 | 0 | 0 | 0 | 0 |
| 16 | 2 | 11.2 | — | 0 | 0 | 0 | 2 | 3 | 0 | 0 | 0 | 1 | 2 |
| 16 | 2 | 5.6 | 0 | 0 | 0 | 2 | 2 | 1 | 0 | 1 | 0 | 0 | 3 |
| 17 | 2 | 11.2 | 0 | 0 | 1 | 0 | 0 | 0 | 0 | 0 | 0 | 0 | 0 |
| 17 | 2 | 5.6 | 0 | — | 0 | 0 | 0 | 0 | 0 | 0 | 0 | 0 | 0 |
| 18 | 2 | 11.2 | 0 | — | 0 | 0 | 0 | 0 | 3 | 0 | 1 | 0 | 3 |

TABLE IX-continued

| Compound Number | WAT | kg/h | A | B | C | D | E | F | G | H | I | J | K |
|---|---|---|---|---|---|---|---|---|---|---|---|---|---|
| 18 | 2 | 5.6 | 0 | 0 | 1 | 0 | 0 | 0 | 3 | 0 | 0 | 0 | 1 |
| 19 | 2 | 11.2 | 1 | 0 | 2 | 2 | 3 | 1 | 1 | 3 | 1 | 3 | 3 |
| 19 | 2 | 5.6 | 0 | 0 | 1 | 2 | 3 | 0 | 2 | 3 | 0 | 3 | 3 |
| 20 | 2 | 11.2 | 0 | 0 | 0 | 0 | 0 | 0 | 1 | 0 | 0 | 0 | 3 |
| 20 | 2 | 5.6 | 0 | 0 | 0 | 0 | 0 | 0 | 0 | 0 | 0 | 0 | 3 |
| 21 | 2 | 11.2 | 0 | 1 | 0 | 1 | 3 | 2 | 1 | 3 | 0 | 3 | 3 |
| 21 | 2 | 5.6 | 0 | 0 | 0 | 0 | 2 | 1 | 0 | 0 | 0 | 1 | 3 |
| 22 | 2 | 11.2 | 0 | 0 | 0 | 0 | 2 | 1 | 3 | 3 | 0 | 1 | 3 |
| 22 | 2 | 5.6 | 0 | 0 | 0 | 0 | 2 | 0 | 2 | 1 | 0 | 3 | 3 |
| 23 | 2 | 11.2 | 0 | 0 | 2 | 3 | 3 | 3 | 3 | 3 | 1 | 3 | 3 |
| 23 | 2 | 5.6 | 3 | 0 | 0 | 0 | 3 | 2 | 3 | 2 | 0 | 3 | 3 |
| 24 | 2 | 11.2 | 0 | 0 | 0 | 1 | 2 | 2 | 3 | 0 | 0 | 3 | 3 |
| 24 | 2 | 5.6 | 0 | 0 | 0 | 0 | 3 | 0 | 1 | 1 | 0 | 1 | 3 |
| 25 | 2 | 11.2 | 3 | 1 | 2 | 0 | 3 | 3 | 3 | 3 | 3 | 3 | 3 |
| 25 | 2 | 5.6 | 3 | 0 | 1 | 0 | 3 | 3 | 3 | 3 | 1 | 3 | 3 |
| 26 | 2 | 11.2 | 0 | 0 | 0 | 0 | 1 | 3 | 1 | 0 | 0 | 2 | 3 |
| 26 | 2 | 5.6 | 0 | 0 | 0 | 0 | 1 | 1 | 0 | 0 | 0 | 1 | 3 |
| 26 | 2 | 11.2 | 3 | 1 | 1 | 2 | 3 | 3 | 3 | 3 | 2 | 3 | 3 |
| 27 | 2 | 5.6 | 1 | 1 | 1 | 2 | 3 | 3 | 3 | 3 | 0 | 3 | 3 |
| 28 | 2 | 11.2 | 3 | 1 | 3 | 3 | 3 | 3 | 3 | 3 | 1 | 3 | 3 |
| 28 | 2 | 5.6 | 0 | 0 | 2 | 2 | 3 | 2 | 2 | 3 | 0 | 3 | 3 |
| 29 | 2 | 11.2 | 3 | 1 | 2 | 2 | 3 | 3 | 3 | 3 | 3 | 3 | 3 |
| 29 | 2 | 5.6 | 3 | 1 | 2 | 3 | 3 | 3 | 3 | 3 | 3 | 3 | 3 |
| 30 | 2 | 11.2 | 2 | 1 | 2 | 2 | 3 | 3 | 3 | 3 | 2 | 3 | 3 |
| 30 | 2 | 5.6 | 0 | 0 | 1 | 0 | 3 | 2 | 3 | 2 | 3 | 3 | 3 |
| 31 | 2 | 11.2 | 3 | 0 | 1 | 0 | 3 | 3 | 3 | 3 | 2 | 3 | 3 |
| 31 | 2 | 5.6 | 1 | 0 | 2 | 1 | 3 | 3 | 3 | 2 | 3 | 3 | 3 |
| 32 | 2 | 11.2 | 2 | 1 | 2 | 2 | 3 | 1 | 3 | 2 | 0 | 3 | 3 |
| 32 | 2 | 5.6 | 1 | 0 | 1 | 0 | 3 | 1 | 0 | 2 | 0 | 3 | 3 |
| 33 | 2 | 11.2 | 3 | 1 | 1 | 1 | 3 | 2 | 3 | 3 | 1 | 3 | 3 |
| 33 | 2 | 5.6 | 1 | 0 | 1 | 1 | 3 | 0 | 3 | 3 | 3 | 3 | 3 |
| 34 | 2 | 11.2 | 3 | 0 | 2 | 2 | 3 | 3 | 3 | 3 | 3 | 3 | 3 |
| 34 | 2 | 5.6 | 3 | 0 | 1 | 0 | 3 | 0 | 3 | 2 | 3 | 3 | 3 |
| 35 | 2 | 11.2 | 2 | 2 | 2 | 2 | 3 | 3 | 3 | 3 | 2 | 3 | 3 |
| 35 | 2 | 5.6 | 0 | 0 | 0 | 0 | 1 | 0 | 0 | 0 | 0 | 0 | 0 |
| 35 | 2 | 11.2 | — | 3 | 3 | 3 | 3 | 3 | 3 | 3 | 3 | 3 | 3 |
| 35 | 2 | 5.6 | — | 2 | 3 | 3 | 3 | 3 | 1 | 3 | 1 | 3 | 3 |
| 36 | 2 | 11.2 | 0 | 1 | 2 | 3 | 3 | 1 | 2 | 2 | 0 | 3 | 3 |
| 36 | 2 | 5.6 | 1 | 0 | 2 | 2 | 3 | 3 | 1 | 2 | 0 | 2 | 3 |
| 37 | 2 | 11.2 | 3 | 1 | 2 | 2 | 3 | 3 | 3 | 3 | 3 | 3 | 3 |
| 37 | 2 | 5.6 | 2 | 1 | 2 | 2 | 3 | 3 | 3 | 3 | 3 | 3 | 3 |
| 38 | 2 | 11.2 | 3 | 1 | 2 | 2 | 3 | 3 | 3 | 3 | 2 | 3 | 3 |
| 38 | 2 | 5.6 | 3 | 0 | 2 | 2 | 3 | 1 | 2 | 3 | 0 | 3 | 3 |
| 39 | 2 | 11.2 | 3 | 2 | 2 | 3 | 3 | 3 | 3 | 3 | 2 | 3 | 3 |
| 39 | 2 | 5.6 | 3 | 1 | 2 | 3 | 3 | 3 | 3 | 3 | 0 | 3 | 3 |
| 40 | 2 | 11.2 | 1 | 1 | 2 | 3 | 3 | 3 | 2 | 3 | 1 | 3 | 3 |
| 40 | 2 | 5.6 | 3 | 0 | 2 | 2 | 3 | 3 | 3 | 3 | 2 | 3 | 3 |
| 41 | 2 | 11.2 | 3 | 1 | 2 | 3 | 3 | 3 | 3 | 3 | 3 | 3 | 3 |
| 41 | 2 | 5.6 | 2 | 0 | 1 | 3 | 3 | 2 | 3 | 3 | 3 | 3 | 3 |
| 42 | 2 | 11.2 | 3 | 0 | 3 | 3 | 3 | 3 | 3 | 3 | 3 | 3 | 3 |
| 42 | 2 | 5.6 | 3 | 0 | 2 | 2 | 3 | 1 | 2 | 3 | 1 | 3 | 3 |
| 43 | 2 | 11.2 | 3 | 0 | 0 | 3 | 3 | 2 | 3 | 3 | 2 | 3 | 3 |
| 43 | 2 | 5.6 | 3 | 0 | 1 | 3 | 3 | 3 | 3 | 3 | 2 | 3 | 3 |
| 44 | 2 | 11.2 | 3 | 0 | 2 | 2 | 3 | 3 | 2 | 3 | 3 | 3 | 3 |
| 44 | 2 | 5.6 | 1 | 0 | 1 | 3 | 3 | 3 | 3 | 3 | 3 | 3 | 3 |
| 45 | 2 | 11.2 | 1 | 0 | 0 | 0 | 1 | 1 | 2 | 2 | 0 | 3 | 3 |
| 45 | 2 | 5.6 | 0 | 0 | 0 | 0 | 0 | 0 | 3 | 1 | 0 | 1 | 3 |
| 46 | 2 | 11.2 | — | 0 | 0 | 0 | 1 | 0 | 0 | 0 | 0 | 0 | 3 |
| 46 | 2 | 5.6 | — | 1 | 0 | 0 | 0 | 0 | 0 | 0 | 0 | 0 | 3 |
| 47 | 2 | 11.2 | 2 | 2 | 2 | 2 | 3 | 2 | 3 | 3 | 1 | 3 | 3 |
| 47 | 2 | 5.6 | 0 | 2 | 2 | 3 | 3 | 2 | 2 | 3 | 0 | 3 | 3 |
| 48 | 2 | 11.2 | 3 | 1 | 3 | 3 | 3 | 3 | 3 | 2 | 3 | 3 | 3 |
| 48 | 2 | 5.6 | 2 | 1 | 2 | 3 | 3 | 3 | 3 | 1 | 3 | 3 | 3 |
| 49 | 2 | 11.2 | 0 | 2 | 1 | 3 | 3 | 3 | 2 | 3 | 0 | 3 | 3 |
| 49 | 2 | 5.6 | 1 | 0 | 0 | 3 | 2 | 3 | 2 | 3 | 2 | 1 | 3 |
| 50 | 2 | 11.2 | 2 | 1 | 2 | 3 | 3 | 3 | 3 | 3 | 0 | 3 | 3 |
| 50 | 2 | 5.6 | 1 | 0 | 1 | 2 | 3 | 3 | 3 | 3 | 0 | 3 | 3 |
| 51 | 2 | 11.2 | 1 | 0 | 2 | 2 | 3 | 1 | 1 | 2 | 1 | 3 | 3 |
| 51 | 2 | 5.6 | 1 | 3 | 1 | 3 | 3 | 3 | 1 | 1 | 0 | 3 | 3 |
| 52 | 2 | 11.2 | 2 | 0 | 2 | 1 | 2 | 2 | 3 | 3 | 3 | 3 | 3 |
| 52 | 2 | 5.6 | 1 | 0 | 0 | 1 | 3 | 1 | 3 | 1 | 3 | 3 | 3 |
| 53 | 2 | 11.2 | 0 | 0 | 0 | 0 | 0 | 0 | 0 | 0 | 1 | 0 | 2 |
| 53 | 2 | 5.6 | 0 | 0 | 0 | 0 | 3 | 0 | 0 | 0 | 0 | 1 | 0 |
| 54 | 2 | 11.2 | 0 | 0 | 1 | 1 | 2 | 3 | 3 | 3 | 3 | 3 | 3 |
| 54 | 2 | 5.6 | 0 | 0 | 0 | 0 | 1 | 1 | 3 | 3 | 3 | 3 | 3 |
| 55 | 2 | 11.2 | 0 | 0 | 1 | 2 | 1 | 3 | 3 | 3 | 3 | 3 | 3 |
| 55 | 2 | 5.6 | 3 | 0 | 1 | 1 | 2 | 1 | 3 | 3 | 3 | 3 | 3 |
| 56 | 2 | 11.2 | 2 | 1 | 2 | 3 | 3 | 3 | 3 | 3 | 1 | 3 | 3 |
| 56 | 2 | 5.6 | 0 | 1 | 1 | 3 | 3 | 2 | 3 | 3 | 1 | 3 | 3 |
| 57 | 2 | 11.2 | 1 | 0 | 0 | 3 | 3 | 2 | 3 | 3 | 1 | 3 | 3 |
| 57 | 2 | 5.6 | 1 | 1 | 0 | 1 | 2 | 1 | 3 | 2 | 1 | 3 | 3 |
| 58 | 2 | 11.2 | 3 | 1 | 1 | 2 | 3 | 3 | 3 | 3 | 0 | 3 | 3 |
| 58 | 2 | 5.6 | 1 | 1 | 1 | 2 | 2 | 2 | 3 | 2 | 0 | 3 | 3 |
| 59 | 2 | 11.2 | 1 | 0 | 0 | 3 | 1 | 1 | 1 | 3 | 2 | 3 | 3 |
| 59 | 2 | 5.6 | 1 | 0 | 0 | 3 | 1 | 0 | 0 | 2 | 3 | 3 | 3 |
| 60 | 2 | 11.2 | 0 | 0 | 1 | 2 | 1 | 0 | 3 | 3 | 0 | 3 | 3 |
| 60 | 2 | 5.6 | 0 | 0 | 1 | 1 | 2 | 0 | 1 | 2 | 0 | 3 | 3 |
| 61 | 2 | 11.2 | 0 | 0 | 0 | 1 | 3 | 3 | 3 | 3 | 3 | 3 | 3 |
| 61 | 2 | 5.6 | 1 | 0 | 0 | 0 | 2 | 3 | 3 | 2 | 0 | 3 | 3 |
| 62 | 2 | 11.2 | 0 | 0 | 0 | 0 | 1 | 2 | 3 | 3 | 0 | 3 | 3 |
| 62 | 2 | 5.6 | 0 | 0 | 0 | 1 | 3 | 3 | 3 | 2 | 1 | 3 | 3 |
| 63 | 2 | 11.2 | 0 | 0 | 1 | 2 | 3 | 2 | 3 | 3 | 3 | 3 | 3 |
| 63 | 2 | 5.6 | 0 | 0 | 0 | 1 | 3 | 2 | 2 | 3 | 1 | 3 | 3 |
| 64 | 2 | 11.2 | 0 | 0 | 0 | 0 | 1 | 0 | 2 | 1 | 0 | 3 | 3 |
| 64 | 2 | 5.6 | 0 | 0 | 0 | 0 | 0 | 0 | 1 | 1 | 0 | 2 | 3 |
| 65 | 2 | 11.2 | 2 | 0 | 1 | 0 | 3 | 3 | 2 | 3 | 3 | 3 | 3 |
| 65 | 2 | 5.6 | 2 | 0 | 0 | 1 | 2 | 2 | 3 | 3 | 1 | 3 | 3 |
| 66 | 2 | 11.2 | — | 0 | 0 | 0 | 1 | 0 | 0 | 0 | 0 | 2 | 3 |
| 66 | 2 | 5.6 | — | 0 | 0 | 0 | 2 | 1 | 0 | 0 | 0 | 2 | 3 |
| 67 | 2 | 11.2 | — | 0 | 0 | 0 | 0 | 1 | 1 | 0 | 3 | 1 | 3 |
| 67 | 2 | 5.6 | — | 0 | 0 | 0 | 0 | 0 | 1 | 1 | 0 | 0 | 3 |
| 68 | 2 | 11.2 | 3 | 2 | 1 | 3 | 3 | 3 | 3 | 3 | 0 | 3 | 3 |
| 68 | 2 | 5.6 | 3 | 2 | 2 | 3 | 2 | 2 | 2 | 3 | 0 | 3 | 3 |
| 69 | 2 | 11.2 | 0 | 0 | 0 | 0 | 1 | 1 | 3 | 1 | 3 | 1 | 3 |
| 69 | 2 | 5.6 | 0 | 0 | 0 | 0 | 0 | 0 | 2 | 1 | 0 | 1 | 3 |
| 69 | 2 | 1.12 | 0 | 0 | 0 | 0 | 0 | 0 | 0 | 0 | 0 | 2 | 3 |
| 70 | 2 | 11.2 | 3 | 2 | 3 | 3 | 3 | 3 | 3 | 3 | 3 | 3 | 3 |
| 70 | 2 | 5.6 | 2 | 1 | 2 | 3 | 3 | 1 | 3 | 3 | 2 | 3 | 3 |
| 71 | 2 | 11.2 | 3 | 2 | 3 | 3 | 3 | 1 | 3 | 3 | 3 | 3 | 3 |
| 71 | 2 | 5.6 | 3 | 1 | 2 | 3 | 3 | 1 | 0 | 2 | 0 | 3 | 3 |
| 72 | 2 | 11.2 | 3 | 0 | 2 | 3 | 3 | 2 | 3 | 3 | 0 | 3 | 3 |
| 72 | 2 | 5.6 | 3 | 0 | 1 | 3 | 3 | 1 | 3 | 2 | 3 | 3 | 3 |
| 73 | 2 | 11.2 | 3 | 1 | 2 | 2 | 3 | 1 | 3 | 3 | 1 | 3 | 3 |
| 73 | 2 | 5.6 | 2 | 1 | 2 | 3 | 3 | 1 | 2 | 3 | 2 | 3 | 3 |
| 74 | 2 | 11.2 | 3 | 0 | 0 | 2 | 3 | 0 | 2 | 2 | 2 | 1 | 3 |
| 74 | 2 | 5.6 | 1 | 0 | 0 | 0 | 2 | 0 | 3 | 0 | 0 | 1 | 3 |
| 75 | 2 | 11.2 | 0 | 0 | 1 | 1 | 3 | 0 | 1 | 1 | 2 | 3 | 3 |
| 75 | 2 | 5.6 | 1 | 0 | 0 | 0 | 3 | 0 | 3 | 2 | 2 | 2 | 3 |
| 76 | 2 | 11.2 | 3 | 3 | 3 | 3 | 3 | 3 | 3 | 3 | 2 | 3 | 3 |
| 76 | 2 | 5.6 | 3 | 3 | 3 | 3 | 3 | 3 | 3 | 3 | 2 | 3 | 3 |
| 77 | 2 | 11.2 | 3 | 2 | 2 | 2 | 3 | 3 | 3 | 3 | 3 | 3 | 3 |
| 77 | 2 | 5.6 | 1 | 2 | 2 | 2 | 3 | 3 | 1 | 3 | 0 | 2 | 3 |
| 78 | 2 | 11.2 | 3 | 1 | 2 | 2 | 3 | 3 | 3 | 3 | 0 | 3 | 3 |
| 78 | 2 | 5.6 | 2 | 2 | 3 | 2 | 3 | 1 | 2 | 3 | 0 | 3 | 3 |
| 79 | 2 | 11.2 | 0 | 0 | 0 | 2 | 0 | 0 | 0 | 0 | 0 | 3 | 3 |
| 79 | 2 | 5.6 | 1 | 1 | 0 | — | 1 | 0 | 0 | 0 | 0 | 3 | 3 |
| 80 | 2 | 11.2 | 2 | 0 | 2 | 1 | 3 | 3 | 1 | 3 | 3 | 3 | 3 |
| 80 | 2 | 5.6 | 1 | 0 | 2 | 2 | 3 | 2 | 3 | 2 | 0 | 3 | 3 |
| 81 | 2 | 11.2 | 3 | 0 | 1 | 3 | 3 | 3 | 3 | 3 | 1 | 3 | 3 |
| 81 | 2 | 5.6 | 2 | 1 | 1 | 2 | 2 | 1 | 3 | 3 | 1 | 3 | 3 |
| 82 | 2 | 11.2 | 2 | 1 | 2 | 1 | 3 | 3 | 3 | 2 | 0 | 3 | 3 |
| 82 | 2 | 5.6 | 0 | 1 | 0 | 1 | 3 | 3 | 3 | 2 | 0 | 2 | 3 |
| 83 | 2 | 11.2 | 3 | 0 | 0 | 1 | 3 | 2 | 1 | 3 | 1 | 3 | 3 |
| 83 | 2 | 5.6 | 3 | 0 | 0 | 1 | 1 | 3 | 3 | 3 | 1 | 3 | 3 |
| 84 | 2 | 11.2 | — | 0 | 1 | 0 | 2 | 0 | 1 | 0 | 0 | 0 | 3 |
| 84 | 2 | 5.6 | — | 0 | 0 | 0 | 0 | 0 | 0 | 0 | 0 | 0 | 2 |
| 85 | 2 | 11.2 | 2 | 2 | 2 | 3 | 3 | 3 | 1 | 3 | 1 | 3 | 3 |
| 85 | 2 | 5.6 | 2 | 1 | 2 | 3 | 3 | 0 | 3 | 3 | 1 | 3 | 3 |
| 86 | 2 | 11.2 | 2 | 1 | 1 | 3 | 3 | 2 | 3 | 3 | 0 | 3 | 3 |
| 86 | 2 | 5.6 | 1 | 0 | 0 | 0 | 2 | 3 | 0 | 3 | 0 | 1 | 3 |
| 87 | 2 | 11.2 | 0 | 0 | 1 | 2 | 2 | 2 | 1 | 3 | 0 | 3 | 3 |
| 87 | 2 | 5.6 | 3 | 0 | 1 | 2 | 3 | 1 | 3 | 0 | 3 | 3 | 3 |
| 88 | 2 | 11.2 | 3 | 0 | 1 | 0 | 3 | 2 | 3 | 3 | 1 | 3 | 3 |
| 88 | 2 | 5.6 | 3 | 0 | 0 | 0 | 2 | 2 | 3 | 3 | 3 | 3 | 3 |
| 89 | 2 | 11.2 | 3 | 0 | 2 | 2 | 3 | 2 | 2 | 3 | 3 | 3 | 3 |
| 89 | 2 | 5.6 | 3 | 0 | 2 | 2 | 3 | 2 | 1 | 3 | 3 | 3 | 3 |
| 90 | 2 | 11.2 | 1 | 3 | 2 | 3 | 3 | 3 | 2 | 3 | 0 | 3 | 3 |
| 90 | 2 | 5.6 | 1 | 1 | 1 | 3 | 3 | 2 | 0 | 2 | 0 | 3 | 3 |
| 91 | 2 | 11.2 | 0 | 0 | 0 | 0 | 0 | 0 | 0 | 0 | 0 | 0 | 1 |
| 91 | 2 | 5.6 | 0 | 0 | 0 | 0 | 0 | 0 | 0 | 0 | 0 | 0 | 0 |
| 92 | 2 | 11.2 | 0 | 0 | 0 | 0 | 0 | 0 | 0 | 0 | 0 | 0 | 3 |
| 92 | 2 | 5.6 | 0 | 0 | 0 | 0 | 0 | 0 | 0 | 0 | 0 | 0 | 1 |
| 93 | 2 | 11.2 | 0 | 0 | 0 | 2 | 2 | 1 | 0 | 2 | 0 | 3 | 3 |
| 93 | 2 | 5.6 | 0 | 0 | 0 | — | 2 | 3 | 0 | 2 | 0 | 3 | 3 |

TABLE IX-continued

| Compound Number | WAT | kg/h | A | B | C | D | E | F | G | H | I | J | K |
|---|---|---|---|---|---|---|---|---|---|---|---|---|---|
| 94 | 2 | 11.2 | 0 | 0 | 1 | 3 | 2 | 1 | 0 | 2 | 0 | 3 | 3 |
| 94 | 2 | 5.6 | 1 | 0 | 0 | — | 1 | 1 | — | 0 | 0 | 3 | 3 |
| 95 | 2 | 11.2 | 3 | 0 | 2 | 2 | 3 | 1 | 3 | 3 | 0 | 3 | 3 |
| 95 | 2 | 5.6 | 1 | 0 | 2 | 2 | 2 | 1 | 3 | 3 | 0 | 3 | 3 |
| 96 | 2 | 11.2 | 1 | 0 | 0 | 2 | 3 | 2 | 3 | 1 | 0 | 1 | 3 |
| 96 | 2 | 5.6 | 0 | 0 | 0 | 0 | 0 | 0 | 0 | 0 | 0 | 0 | 3 |
| 97 | 2 | 11.2 | 2 | 0 | 0 | 1 | 3 | 0 | 0 | 0 | 0 | 3 | 3 |
| 97 | 2 | 5.6 | 0 | 0 | 0 | 0 | 2 | 2 | 3 | 0 | 0 | 3 | 3 |
| 98 | 2 | 11.2 | 1 | 0 | 0 | 0 | 3 | 2 | 1 | 1 | 0 | 3 | 3 |
| 98 | 2 | 5.6 | 1 | 0 | 1 | 0 | 2 | 1 | 3 | 0 | 0 | 3 | 3 |
| 99 | 2 | 11.2 | 2 | 0 | 1 | 2 | 3 | 2 | 3 | 3 | 0 | 3 | 3 |
| 99 | 2 | 5.6 | 0 | 0 | 1 | 1 | 2 | 1 | 1 | 3 | 0 | 3 | 3 |
| 100 | 2 | 11.2 | 0 | 1 | 0 | 1 | 3 | 2 | 0 | 2 | 0 | 3 | 3 |
| 100 | 2 | 5.6 | 1 | 1 | 0 | 1 | 2 | 0 | 0 | 1 | 0 | 2 | 3 |
| 101 | 2 | 11.2 | 0 | 0 | 0 | 1 | 2 | 2 | 0 | 2 | 1 | 2 | 3 |
| 101 | 2 | 5.6 | 0 | 2 | 0 | 2 | 2 | 1 | 1 | 1 | 0 | 2 | 3 |
| 102 | 2 | 11.2 | 3 | 2 | 1 | 0 | 1 | 2 | 2 | 1 | 0 | 3 | 3 |
| 102 | 2 | 5.6 | 0 | 0 | 0 | 0 | 0 | 1 | 0 | 1 | 0 | 1 | 3 |
| 103 | 2 | 11.2 | 2 | 0 | 2 | 2 | 3 | 3 | 3 | 3 | 3 | 3 | 3 |
| 103 | 2 | 5.6 | 3 | 0 | 2 | 0 | 3 | 3 | 3 | 3 | 0 | 3 | 3 |
| 104 | 2 | 11.2 | 3 | 0 | 0 | 0 | 3 | 3 | 3 | 3 | 3 | 2 | 3 |
| 104 | 2 | 5.6 | 2 | 0 | 0 | 1 | 3 | 3 | 3 | 2 | 1 | 3 | 3 |
| 105 | 2 | 11.2 | 1 | 0 | 1 | 2 | 3 | 3 | 3 | 3 | 3 | 3 | 3 |
| 105 | 2 | 5.6 | 1 | 0 | 0 | 2 | 3 | 3 | 3 | 3 | 2 | 3 | 3 |
| 106 | 2 | 11.2 | 0 | 0 | 0 | 2 | 2 | 3 | 1 | 3 | 0 | 3 | 3 |
| 106 | 2 | 5.6 | 1 | 0 | 0 | 2 | 2 | 3 | 3 | 3 | 0 | 2 | 3 |
| 107 | 2 | 11.2 | 0 | 0 | 0 | 0 | 0 | 0 | 0 | 0 | 0 | 0 | 2 |
| 108 | 2 | 11.2 | 3 | 0 | 2 | 2 | 3 | 3 | 2 | 3 | 0 | 3 | 3 |
| 108 | 2 | 5.6 | 3 | 0 | 2 | 2 | 3 | 3 | 1 | 3 | 0 | 3 | 3 |
| 109 | 2 | 11.2 | 1 | 0 | 1 | 2 | 3 | 2 | 3 | 3 | 0 | 2 | 3 |
| 109 | 2 | 5.6 | 3 | 0 | 1 | 2 | 2 | 2 | 3 | 3 | 0 | 3 | 3 |

TABLE X

| Compound No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 2 | 5.6 | 2 | 2 | 1 | 3 | 3 | 0 | 2 | 3 | 3 | 3 | 3 | 2 | 3 | 3 | 3 | 3 |
| 1 | 2 | 1.12 | 1 | 1 | 1 | 1 | 3 | 0 | 1 | 1 | 1 | 3 | 1 | 0 | 3 | 3 | 3 | 3 |
| 1 | 2 | 0.28 | 0 | 0 | 0 | 0 | 1 | 0 | 0 | 0 | 0 | 1 | 0 | 0 | 1 | 2 | 3 | 3 |
| 1 | 2 | 0.056 | 1 | 0 | — | 0 | 1 | 0 | 0 | 0 | — | 0 | 0 | 0 | 1 | 1 | 2 | 2 |
| 3 | 2 | 5.6 | 1 | 1 | 0 | 2 | 2 | 0 | 0 | 2 | 3 | 3 | 2 | 0 | 0 | 2 | 3 | 3 |
| 3 | 2 | 1.12 | 0 | 0 | 0 | 0 | 0 | 0 | 0 | 0 | 0 | 0 | 0 | 0 | 0 | 0 | 2 | 2 |
| 3 | 2 | 0.28 | 0 | 0 | 0 | 0 | 0 | 0 | 0 | 0 | 0 | 2 | 1 | 0 | 0 | 2 | 1 | 2 |
| 4 | 2 | 5.6 | 0 | 0 | 0 | 0 | 0 | 0 | 0 | 0 | 1 | 0 | 0 | 0 | 0 | 1 | 2 | 3 |
| 4 | 2 | 1.12 | 1 | 0 | 0 | 0 | 0 | 0 | 0 | 0 | 0 | 3 | 0 | 0 | 0 | 0 | 0 | 2 |
| 4 | 2 | 0.28 | 0 | 0 | 0 | 0 | 0 | 0 | 0 | 0 | 0 | 3 | 0 | 0 | 0 | 0 | 0 | 2 |
| 5 | 2 | 5.6 | 2 | 1 | 0 | 1 | 3 | 0 | 0 | 3 | 0 | 3 | 3 | 2 | 2 | 2 | 3 | 3 |
| 5 | 2 | 1.12 | 0 | 0 | 0 | 0 | 3 | 0 | 0 | — | 1 | 2 | 0 | 1 | 0 | 1 | 1 | 3 |
| 5 | 2 | 0.28 | 0 | 0 | 0 | 0 | 0 | 0 | 0 | 0 | 0 | 0 | 0 | 0 | 0 | 0 | 0 | 2 |
| 6 | 2 | 5.6 | 3 | 2 | 1 | 2 | 2 | 2 | 2 | 3 | 2 | 3 | 3 | 1 | 2 | 3 | 3 | 3 |
| 6 | 2 | 1.12 | 2 | 2 | 1 | 2 | 3 | 1 | 2 | 2 | 2 | 3 | 3 | 0 | 3 | 2 | 3 | 3 |
| 6 | 2 | 0.28 | 0 | 2 | 1 | 1 | 1 | 0 | 1 | 0 | 2 | 3 | 3 | 1 | 0 | 1 | 2 | 3 |
| 6 | 2 | 0.056 | 0 | 0 | 0 | 0 | 0 | 1 | 0 | 0 | 2 | 3 | 2 | 0 | 1 | 0 | 0 | 3 |
| 7 | 2 | 5.6 | 1 | 2 | 3 | 3 | 3 | 1 | 0 | 2 | 1 | 2 | 1 | 0 | 2 | 3 | 3 | 3 |
| 7 | 2 | 1.12 | 0 | 1 | 1 | 2 | 3 | 0 | 0 | 2 | 1 | 2 | 1 | 0 | 3 | 3 | 3 | 3 |
| 7 | 2 | 0.28 | 0 | 0 | 0 | 1 | 1 | 0 | 0 | 1 | 0 | 2 | 0 | 0 | 1 | 3 | 3 | 3 |
| 10 | 2 | 5.6 | 0 | 1 | 0 | 0 | 0 | 1 | 1 | 3 | 2 | 2 | 0 | 0 | 0 | 1 | 3 | 3 |
| 10 | 2 | 1.12 | 0 | 0 | 0 | 0 | 1 | 0 | 0 | 0 | 3 | 0 | 0 | 0 | 0 | 0 | 2 | 2 |
| 10 | 2 | 0.28 | 0 | 0 | 0 | 0 | 0 | 0 | 0 | 0 | 1 | 2 | 0 | 0 | 0 | 0 | 0 | 2 |
| 13 | 2 | 5.6 | 0 | 0 | 0 | 0 | 0 | 0 | 0 | 0 | 1 | 0 | 0 | 0 | 0 | 0 | 0 | 3 |
| 13 | 2 | 1.12 | 0 | 0 | 0 | 0 | 0 | 0 | 0 | 0 | 0 | 3 | 0 | 0 | 0 | 0 | 0 | 0 |
| 13 | 2 | 0.28 | 0 | 0 | 0 | 0 | 0 | 0 | 0 | 0 | 0 | 0 | 0 | 0 | 0 | 0 | 0 | 0 |
| 16 | 2 | 5.6 | 0 | 0 | 0 | 0 | 0 | 0 | 0 | 0 | 3 | 2 | 2 | 0 | 0 | 0 | 2 | 3 |
| 16 | 2 | 1.12 | 0 | 0 | 0 | 0 | 0 | 1 | 0 | 0 | 0 | 2 | 1 | 0 | 0 | 1 | 2 | 3 |
| 16 | 2 | 0.28 | 0 | 0 | 0 | 0 | 0 | 1 | 1 | 0 | 0 | 2 | 1 | 0 | 0 | 0 | 1 | 3 |
| 18 | 2 | 5.6 | 0 | 0 | 0 | 0 | 3 | 0 | 0 | 0 | 0 | 2 | 1 | 0 | 2 | 1 | 3 | 3 |
| 18 | 2 | 1.12 | 0 | 1 | 0 | 0 | 0 | 0 | 0 | 0 | 0 | 0 | 0 | 0 | 0 | 1 | 3 | 3 |
| 18 | 2 | 0.28 | 0 | 1 | 0 | 0 | 0 | 0 | 0 | 0 | — | 1 | 0 | 0 | 0 | 0 | 0 | 2 |
| 19 | 2 | 5.6 | 1 | 2 | 2 | 2 | 3 | 0 | 3 | 3 | 2 | 3 | 2 | 1 | 3 | 3 | 3 | 3 |
| 19 | 2 | 1.12 | 0 | 1 | 0 | 1 | 2 | 0 | 1 | 1 | 1 | 3 | 1 | 0 | 3 | 3 | 3 | 3 |
| 19 | 2 | 0.28 | 0 | 1 | 0 | 0 | 1 | 0 | 0 | 1 | 2 | 2 | 0 | 0 | 2 | 3 | 3 | 3 |
| 19 | 2 | 0.056 | 0 | 0 | 0 | 0 | 0 | 0 | 0 | 0 | 2 | 1 | 0 | 0 | 0 | 0 | 2 | 2 |
| 19 | 2 | 0.0112 | 0 | 0 | 0 | 0 | 0 | 0 | 0 | 0 | 1 | 1 | 0 | 0 | 0 | 0 | 1 | 2 |
| 20 | 2 | 5.6 | 0 | 0 | 0 | 0 | 0 | 0 | 0 | 0 | 3 | 2 | 0 | 0 | 0 | 1 | 3 | 3 |
| 20 | 2 | 1.12 | 0 | 1 | 0 | 1 | 0 | 0 | 0 | 0 | 1 | 1 | 0 | 0 | 1 | 1 | 3 | 2 |
| 20 | 2 | 0.28 | 0 | 0 | 0 | 0 | 0 | 0 | 0 | 0 | 0 | 0 | 0 | 0 | 0 | 0 | 1 | 2 |
| 20 | 2 | 0.056 | 0 | 0 | 0 | 0 | 0 | 0 | 0 | 0 | 1 | 0 | 0 | 0 | 0 | 0 | 2 | 2 |
| 20 | 2 | 0.0112 | 0 | 0 | 0 | 0 | 0 | 0 | 0 | 0 | 1 | 0 | 0 | 0 | 0 | 0 | 0 | 1 |
| 21 | 2 | 5.6 | 0 | 2 | 2 | 3 | 2 | 0 | 1 | 1 | 1 | 3 | 3 | 0 | 3 | 3 | 3 | 3 |
| 21 | 2 | 1.12 | 0 | 0 | 0 | 1 | 1 | 0 | 0 | 0 | 2 | 1 | 0 | 1 | 3 | 3 | 3 | 3 |
| 21 | 2 | 0.28 | 0 | 0 | 0 | 0 | 0 | 0 | 0 | 0 | 0 | 0 | 0 | 0 | 0 | 0 | 3 | 3 |
| 21 | 2 | 0.056 | 0 | 0 | 0 | 1 | 1 | 1 | 0 | 1 | — | — | 0 | 0 | 1 | 1 | 2 | 3 |
| 21 | 2 | 0.0112 | 0 | 0 | 0 | 0 | 0 | 0 | — | 0 | 0 | 0 | 0 | 0 | 0 | 0 | 3 | 2 |
| 22 | 2 | 5.6 | 0 | 1 | 2 | 3 | 3 | 0 | 1 | 2 | 0 | 3 | 3 | 0 | 3 | 3 | 3 | 3 |
| 22 | 2 | 1.12 | 0 | 0 | 0 | 2 | 0 | 0 | 1 | 1 | 1 | 2 | 1 | 0 | 1 | 3 | 3 | 3 |
| 22 | 2 | 0.28 | 0 | 0 | 0 | 0 | 0 | 0 | 0 | 0 | 1 | 1 | 0 | 0 | 0 | 3 | 3 | 3 |
| 22 | 2 | 0.056 | 0 | 0 | 0 | 0 | 0 | 0 | 0 | 0 | 2 | 1 | 0 | 0 | 1 | 2 | 2 | 2 |
| 23 | 2 | 5.6 | 0 | 1 | 2 | 2 | 3 | 0 | 1 | 1 | 1 | 3 | 2 | 1 | 3 | 3 | 3 | 3 |
| 23 | 2 | 1.12 | 0 | 0 | 0 | 1 | 3 | 0 | 0 | 1 | 0 | 3 | 1 | 0 | 3 | 3 | 3 | 3 |
| 23 | 2 | 0.28 | 0 | 0 | 1 | 1 | 0 | 0 | 1 | 0 | 3 | 1 | 0 | 3 | 3 | 3 | 3 | 3 |
| 23 | 2 | 0.056 | 0 | 0 | 0 | 0 | 0 | 0 | 0 | 0 | 0 | 0 | 0 | 0 | 0 | 3 | 3 | 2 |
| 23 | 2 | 0.0112 | 0 | 0 | 0 | 0 | 0 | 0 | 0 | 0 | 0 | 0 | 0 | 0 | 0 | 3 | 2 | 1 |

TABLE X-continued

| Compound No. | WAT | kg/h | L | M | N | O | P | B | Q | D | R | E | F | C | J | S | K | T |
|---|---|---|---|---|---|---|---|---|---|---|---|---|---|---|---|---|---|---|
| 24 | 2 | 5.6 | 0 | 1 | 3 | 2 | 1 | 0 | 1 | 0 | 0 | 1 | 1 | 0 | 3 | 3 | 3 | 3 |
| 24 | 2 | 1.12 | 0 | 0 | 0 | 0 | 0 | 0 | 0 | 0 | 0 | 1 | 1 | 0 | 3 | 3 | 3 | 3 |
| 24 | 2 | 0.28 | 0 | 0 | 0 | 0 | 0 | 0 | 0 | 0 | 0 | 0 | 0 | 0 | 0 | 1 | 3 | 2 |
| 24 | 2 | 0.056 | 0 | 0 | 0 | 0 | 0 | 0 | 0 | 0 | 0 | 1 | 0 | 0 | 0 | 0 | 0 | 2 |
| 25 | 2 | 5.6 | 0 | 0 | 2 | 2 | 3 | 0 | 3 | 1 | 0 | 3 | 3 | 0 | 3 | 3 | 3 | 3 |
| 25 | 2 | 1.12 | 0 | 0 | 1 | 1 | 3 | 0 | 2 | 0 | 0 | 3 | 3 | 0 | 3 | 3 | 3 | 3 |
| 25 | 2 | 0.28 | 0 | 0 | 0 | 0 | 0 | 0 | 0 | 0 | 0 | 0 | 0 | 0 | 0 | 3 | 3 | 3 |
| 25 | 2 | 0.056 | 0 | 0 | 0 | 0 | 1 | 0 | 0 | 0 | 0 | 2 | 1 | 0 | 0 | 3 | 2 | 3 |
| 25 | 2 | 0.0112 | 0 | 0 | 0 | 0 | 0 | 0 | 0 | 0 | 0 | 2 | 1 | 0 | 0 | 3 | 3 | 2 |
| 26 | 2 | 5.6 | 0 | 0 | 0 | 2 | 1 | 0 | 0 | 1 | 0 | 2 | 2 | 0 | 2 | 2 | 3 | 3 |
| 26 | 2 | 1.12 | 0 | 0 | 0 | 0 | 0 | 0 | 0 | 0 | 0 | 3 | 1 | 0 | 0 | 2 | 3 | 2 |
| 26 | 2 | 0.28 | 0 | 0 | 0 | 0 | 0 | 0 | 0 | 0 | 0 | 0 | 0 | 0 | 0 | 0 | 3 | 1 |
| 26 | 2 | 0.056 | 0 | 0 | 0 | 0 | 0 | 0 | 0 | 0 | 0 | 0 | 0 | 0 | 0 | 0 | 0 | 0 |
| 27 | 2 | 5.6 | 0 | 2 | 2 | 3 | 3 | 1 | 3 | 3 | 3 | 3 | 3 | 3 | 3 | 3 | 3 | 3 |
| 27 | 2 | 1.12 | 0 | 2 | 1 | 3 | 3 | 1 | 3 | 2 | 3 | 3 | 3 | 1 | 3 | 3 | 3 | 3 |
| 27 | 2 | 0.28 | 0 | 2 | 1 | 0 | 1 | 0 | 1 | 2 | 3 | 3 | 2 | 0 | 1 | 3 | 3 | 3 |
| 27 | 2 | 0.056 | 0 | 1 | 0 | 0 | 0 | 0 | 0 | 0 | 0 | 0 | 1 | 0 | 2 | 0 | 3 | 3 |
| 27 | 2 | 0.0112 | 0 | 0 | 0 | 0 | 0 | 0 | 0 | 0 | 0 | 0 | 0 | 0 | 0 | 0 | 1 | 2 |
| 28 | 2 | 5.6 | 0 | 2 | 2 | 3 | 3 | 0 | 2 | 3 | 2 | 3 | 3 | 2 | 3 | 3 | 3 | 3 |
| 28 | 2 | 1.12 | 0 | 2 | 1 | 3 | 3 | 0 | 2 | 1 | 2 | 3 | 3 | 1 | 3 | 3 | 3 | 3 |
| 28 | 2 | 0.28 | 0 | 1 | 0 | 1 | 3 | 0 | 0 | 0 | 1 | 2 | 0 | 0 | 1 | 3 | 3 | 3 |
| 28 | 2 | 0.056 | 0 | 0 | 0 | 0 | 1 | 0 | 0 | 0 | 0 | 3 | 0 | 0 | 0 | 1 | 3 | 3 |
| 28 | 2 | 0.0112 | 0 | 0 | 0 | 0 | 0 | 0 | 0 | 0 | 0 | 3 | 0 | 0 | 0 | 0 | 1 | 2 |
| 29 | 2 | 5.6 | 1 | 2 | 3 | 3 | 3 | 2 | 3 | 3 | 2 | 3 | 3 | 2 | 3 | 3 | 3 | 3 |
| 29 | 2 | 1.12 | 0 | 1 | 1 | 3 | 3 | 1 | 2 | 2 | 1 | 3 | 3 | 0 | 3 | 3 | 3 | 3 |
| 29 | 2 | 0.28 | 0 | 1 | 0 | 3 | 3 | 0 | 1 | 0 | 3 | 3 | 1 | 0 | 1 | 3 | 3 | 3 |
| 29 | 2 | 0.056 | 0 | 0 | 0 | 0 | 1 | 0 | 1 | 0 | 3 | 0 | 0 | 0 | 1 | 1 | 3 | 3 |
| 29 | 2 | 0.0112 | 0 | 0 | 0 | 0 | 0 | 0 | 1 | 0 | 2 | 0 | 0 | 0 | 0 | 0 | 2 | 2 |
| 30 | 2 | 5.6 | 0 | 2 | 3 | 3 | 3 | 1 | 3 | 2 | 3 | 3 | 3 | 1 | 3 | 3 | 3 | 3 |
| 30 | 2 | 1.12 | 0 | 1 | 0 | 1 | 3 | 1 | 1 | 0 | 1 | 1 | 1 | 0 | 2 | 3 | 3 | 3 |
| 30 | 2 | 0.28 | 0 | 0 | 0 | 0 | 3 | 0 | 0 | 0 | 0 | 0 | 0 | 0 | 1 | 2 | 3 | 3 |
| 30 | 2 | 0.056 | 0 | 0 | 0 | 0 | 0 | 0 | 0 | 0 | 0 | 0 | 0 | 0 | 0 | 0 | 2 | 2 |
| 30 | 2 | 0.0112 | 0 | 0 | 0 | 0 | 0 | 0 | 0 | 0 | 0 | 0 | 0 | 0 | 0 | 0 | 2 | 1 |
| 31 | 2 | 5.6 | 1 | 1 | 2 | 3 | 3 | 1 | 2 | 2 | 1 | 3 | 3 | 1 | 3 | 3 | 3 | 3 |
| 31 | 2 | 1.12 | 0 | 0 | 0 | 2 | 3 | 0 | 1 | 1 | 0 | 2 | 2 | 0 | 3 | 3 | 3 | 3 |
| 31 | 2 | 0.28 | 0 | 0 | 0 | 1 | 3 | 1 | 2 | 0 | 3 | 3 | 2 | 0 | 3 | 3 | 3 | 3 |
| 31 | 2 | 0.056 | 0 | 0 | 0 | 0 | 0 | 0 | 0 | 0 | 3 | 1 | 2 | 0 | 0 | 1 | 2 | 3 |
| 31 | 2 | 0.0112 | 0 | 0 | 0 | 0 | 0 | 0 | 0 | 0 | 0 | 0 | 0 | 0 | 0 | 0 | 0 | 0 |
| 32 | 2 | 5.6 | 0 | 2 | 2 | 3 | 3 | 0 | 2 | 1 | 2 | 3 | 1 | 1 | 3 | 3 | 3 | 3 |
| 32 | 2 | 1.12 | 0 | 0 | 0 | 1 | 3 | 0 | 1 | 0 | 1 | 2 | 2 | 0 | 3 | 3 | 3 | 3 |
| 32 | 2 | 0.28 | 0 | 0 | 0 | 0 | 0 | 0 | 0 | — | 0 | 0 | 0 | 0 | 0 | 3 | 3 | 1 |
| 32 | 2 | 0.056 | 0 | 0 | 0 | 0 | 0 | 0 | 0 | 0 | 0 | 1 | 0 | 0 | 0 | 0 | 1 | 1 |
| 33 | 2 | 5.6 | 1 | 2 | 3 | 3 | 3 | 1 | 3 | 3 | 2 | 3 | 2 | 2 | 3 | 3 | 3 | 3 |
| 33 | 2 | 1.12 | 0 | 1 | 2 | 3 | 3 | 0 | 1 | 0 | 2 | 3 | 2 | 1 | 3 | 3 | 3 | 3 |
| 33 | 2 | 0.28 | 0 | 0 | 0 | 1 | 3 | 0 | 1 | 0 | 0 | 3 | 0 | 0 | 0 | 2 | 3 | 3 |
| 33 | 2 | 0.056 | 0 | 0 | 0 | 0 | 0 | 0 | 0 | 0 | 0 | 0 | 0 | 0 | 0 | 1 | 3 | 3 |
| 33 | 2 | 0.0112 | 0 | 0 | 0 | 0 | 0 | 0 | 0 | 0 | 0 | 0 | 0 | 0 | 0 | 0 | 1 | 2 |
| 34 | 2 | 5.6 | 0 | 2 | 3 | 3 | 3 | 0 | 3 | 1 | 2 | 3 | 2 | 1 | 3 | 3 | 3 | 3 |
| 34 | 2 | 1.12 | 0 | 1 | 2 | 2 | 3 | 0 | 2 | 0 | 2 | 0 | 1 | 0 | 3 | 3 | 3 | 3 |
| 34 | 2 | 0.28 | 0 | 0 | 1 | 1 | 2 | 0 | 1 | 0 | 0 | 0 | 0 | 1 | 1 | 3 | 3 | 3 |
| 34 | 2 | 0.056 | 0 | 0 | 0 | 0 | 0 | 0 | 0 | 0 | 1 | 3 | 1 | 0 | 0 | 0 | 3 | 3 |
| 34 | 2 | 0.0112 | 0 | 0 | 0 | 0 | 0 | 0 | 0 | 0 | 0 | 1 | 1 | 0 | 0 | 0 | 1 | 1 |
| 35 | 2 | 5.6 | 0 | 3 | 0 | 3 | 3 | 3 | 3 | 3 | 3 | 3 | 3 | 2 | 3 | 3 | 3 | 3 |
| 35 | 2 | 1.12 | 0 | 1 | 0 | 2 | 3 | 0 | 1 | 0 | 2 | 3 | 2 | 1 | 3 | 3 | 3 | 3 |
| 35 | 2 | 0.28 | 0 | 1 | 0 | 0 | 3 | 0 | 0 | 0 | 0 | 3 | 1 | 0 | 1 | 3 | 3 | 3 |
| 35 | 2 | 0.056 | 0 | 0 | 0 | 0 | 0 | 0 | 0 | 0 | 0 | 2 | 1 | 0 | 0 | 1 | 1 | 2 |
| 36 | 2 | 5.6 | 0 | 3 | 2 | 3 | 3 | 1 | 3 | 3 | 3 | 3 | 3 | 2 | 3 | 3 | 3 | 3 |
| 36 | 2 | 1.12 | 0 | 2 | 0 | 2 | 0 | 0 | 2 | 0 | 3 | 3 | 1 | 1 | 1 | 3 | 3 | 3 |
| 36 | 2 | 0.28 | 0 | 1 | 0 | 0 | 0 | 0 | 0 | 0 | 0 | 1 | 0 | 0 | 0 | 2 | 3 | 3 |
| 36 | 2 | 0.056 | 0 | 0 | 0 | 0 | 0 | 0 | 0 | — | 0 | 3 | 0 | 0 | 0 | 3 | 3 | 3 |
| 36 | 2 | 0.0112 | 0 | 1 | 0 | 0 | 0 | 0 | 0 | 0 | 0 | 3 | 0 | 0 | 1 | 2 | 2 | 2 |
| 37 | 2 | 5.6 | 1 | 3 | 2 | 3 | 3 | 1 | 3 | 2 | 3 | 3 | 3 | 2 | 3 | 3 | 3 | 3 |
| 37 | 2 | 1.12 | 1 | 2 | 2 | 2 | 3 | 0 | 3 | 3 | 1 | 3 | 0 | 1 | 3 | 3 | 3 | 3 |
| 37 | 2 | 0.28 | 0 | 2 | 0 | 1 | 2 | 0 | 1 | 2 | 0 | 1 | 1 | 0 | 2 | 2 | 3 | 3 |
| 37 | 2 | 0.056 | 0 | 1 | 0 | 1 | 0 | 0 | 1 | 0 | 1 | 1 | 2 | 0 | 0 | 1 | 3 | 3 |
| 37 | 2 | 0.0112 | 0 | 0 | 0 | 0 | 0 | 0 | 0 | 0 | 0 | 3 | 1 | 0 | 0 | 0 | 2 | 2 |
| 38 | 2 | 5.6 | 2 | 3 | 2 | 3 | 3 | 1 | 3 | 3 | 3 | 3 | 3 | 2 | 3 | 3 | 3 | 3 |
| 38 | 2 | 1.12 | 0 | 3 | 1 | 1 | 3 | 0 | 3 | 2 | 2 | 3 | 3 | 1 | 3 | 3 | 3 | 3 |
| 38 | 2 | 0.28 | 0 | 2 | 0 | 1 | 2 | 0 | 1 | 3 | 2 | 3 | 2 | 0 | 2 | 3 | 3 | 3 |
| 38 | 2 | 0.056 | 0 | 3 | 0 | 1 | 0 | 0 | 1 | 0 | 0 | 3 | 0 | 0 | 0 | 1 | 2 | 3 |
| 38 | 2 | 0.0112 | 0 | 0 | 0 | 0 | 0 | 0 | 0 | 0 | 1 | 1 | 1 | 0 | 0 | 0 | 1 | 2 |
| 39 | 2 | 5.6 | 0 | 3 | 3 | 3 | 3 | 2 | 3 | 2 | 3 | 3 | 3 | 2 | 3 | 3 | 3 | 3 |
| 39 | 2 | 1.12 | 0 | 3 | 0 | 2 | 3 | 1 | 3 | 1 | 2 | 3 | 3 | 1 | 3 | 3 | 3 | 3 |
| 39 | 2 | 0.28 | 0 | 3 | 0 | 0 | 1 | 0 | 1 | 0 | 3 | 2 | 0 | 0 | 3 | 3 | 3 | 3 |
| 39 | 2 | 0.056 | 0 | 1 | 0 | 0 | 1 | 0 | 0 | 2 | 0 | 1 | 0 | 0 | 0 | 1 | 2 | 3 |
| 39 | 2 | 0.0112 | 0 | 0 | 0 | 0 | 0 | 0 | 0 | 0 | 0 | 1 | 0 | 0 | 0 | 2 | 2 | 3 |
| 40 | 2 | 5.6 | 1 | 3 | 3 | 3 | 3 | 1 | 2 | 3 | 3 | 3 | 3 | 2 | 3 | 3 | 3 | 3 |
| 40 | 2 | 1.12 | 0 | 2 | 0 | 2 | 3 | 0 | 3 | 3 | 2 | 2 | 2 | 1 | 3 | 3 | 3 | 3 |
| 40 | 2 | 0.28 | 0 | 0 | 0 | 1 | 1 | 0 | 0 | 1 | 0 | 1 | 0 | 0 | 1 | 3 | 3 | 3 |
| 40 | 2 | 0.056 | 0 | 0 | 0 | 0 | 1 | 0 | 1 | 0 | 0 | 0 | 0 | 0 | 0 | 1 | 3 | 3 |

TABLE X-continued

| Compound No. | WAT | kg/h | L | M | N | O | P | B | Q | D | R | E | F | C | J | S | K | T |
|---|---|---|---|---|---|---|---|---|---|---|---|---|---|---|---|---|---|---|
| 40 | 2 | 0.0112 | 0 | 0 | 0 | 0 | 0 | 0 | 0 | 0 | 0 | — | 0 | 0 | 0 | 1 | 2 | 2 |
| 41 | 2 | 5.6 | 2 | 2 | 3 | 3 | 3 | 1 | 2 | 3 | 3 | 3 | 3 | 2 | 3 | 3 | 3 | 3 |
| 41 | 2 | 1.12 | 1 | 2 | 3 | 3 | 3 | 0 | 1 | 3 | 3 | 3 | 3 | 1 | 3 | 3 | 3 | 3 |
| 41 | 2 | 0.28 | 0 | 2 | 2 | 3 | 3 | 0 | 1 | 2 | 3 | 3 | 3 | 0 | 3 | 3 | 3 | 3 |
| 41 | 2 | 0.056 | 0 | 1 | 0 | 1 | 1 | 0 | 1 | 0 | 1 | 3 | 0 | 0 | 2 | 3 | 3 | 3 |
| 41 | 2 | 0.0112 | 0 | 0 | 0 | 0 | 0 | 0 | 0 | 0 | 1 | 1 | 0 | 0 | 0 | 0 | 2 | 3 |
| 42 | 2 | 5.6 | 2 | 3 | 3 | 3 | 3 | 1 | 2 | 3 | 3 | 3 | 3 | 3 | 3 | 3 | 3 | 3 |
| 42 | 2 | 1.12 | 0 | 3 | 2 | 2 | 3 | 0 | 0 | 1 | 2 | 2 | 2 | 1 | 3 | 3 | 3 | 3 |
| 42 | 2 | 0.28 | 1 | 1 | 1 | 2 | 2 | — | 1 | 3 | 3 | 2 | 1 | 0 | 3 | 2 | 3 | 3 |
| 42 | 2 | 0.056 | 0 | 1 | 0 | 0 | 0 | 0 | 0 | 0 | 1 | 3 | 2 | 0 | 0 | 0 | 2 | 3 |
| 42 | 2 | 0.0112 | 0 | 1 | 0 | 0 | 0 | 0 | 0 | 0 | 0 | 3 | 0 | 1 | 0 | 0 | 1 | 2 |
| 43 | 2 | 5.6 | 2 | 3 | 3 | 3 | 3 | 3 | 3 | 3 | 3 | 3 | 3 | 2 | 3 | 3 | 3 | 3 |
| 43 | 2 | 1.12 | 0 | 2 | 1 | 2 | 3 | 3 | 1 | 1 | 1 | 3 | 3 | 0 | 3 | 3 | 3 | 3 |
| 43 | 2 | 0.28 | 0 | 0 | 2 | 2 | 3 | 3 | 1 | 2 | 1 | 1 | 1 | 2 | 3 | 3 | 3 | 3 |
| 43 | 2 | 0.056 | 0 | 0 | 0 | 0 | 3 | 0 | 0 | 1 | 0 | 1 | 0 | 0 | 2 | 1 | 3 | 3 |
| 43 | 2 | 0.0112 | 0 | 0 | 0 | 0 | 0 | 0 | 0 | 0 | 3 | 3 | 3 | 0 | 0 | 0 | 2 | 3 |
| 44 | 2 | 5.6 | 1 | 2 | 3 | 3 | 3 | 0 | 3 | 3 | 3 | 3 | 3 | 2 | 3 | 3 | 3 | 3 |
| 44 | 2 | 1.12 | 0 | 2 | 3 | 3 | 3 | 0 | 1 | 1 | 2 | 3 | 2 | 0 | 3 | 3 | 3 | 3 |
| 44 | 2 | 0.28 | 0 | 0 | 0 | 1 | 2 | 1 | 0 | 0 | 0 | 3 | 2 | 0 | 2 | 3 | 3 | 3 |
| 44 | 2 | 0.056 | 0 | 0 | 0 | 0 | 0 | 0 | 0 | 0 | 0 | 0 | 0 | 1 | 0 | 1 | 3 | 3 |
| 44 | 2 | 0.0112 | 0 | 0 | 0 | 0 | 0 | 0 | 0 | 0 | 0 | 0 | 0 | 0 | 0 | 0 | 1 | 2 |
| 45 | 2 | 5.6 | 0 | 1 | 0 | 1 | 0 | 0 | 0 | 0 | 1 | 0 | 1 | 0 | 3 | 2 | 3 | — |
| 45 | 2 | 1.12 | 0 | 0 | 0 | 0 | 0 | 0 | 0 | 0 | 0 | 0 | 0 | 0 | 0 | 0 | 2 | — |
| 45 | 2 | 0.28 | 0 | 0 | 0 | 0 | 0 | 0 | 0 | 0 | 0 | 0 | 0 | 0 | 0 | 0 | 1 | — |
| 45 | 2 | 0.056 | 0 | 0 | 0 | 0 | 0 | 0 | 0 | 0 | 0 | 0 | 0 | 0 | 0 | 0 | 0 | — |
| 46 | 2 | 5.6 | 0 | 0 | 0 | 2 | 0 | 0 | 0 | 0 | 0 | 0 | 0 | 0 | 1 | 3 | 3 | — |
| 46 | 2 | 1.12 | 0 | 0 | 0 | 0 | 0 | 0 | 0 | 0 | 0 | 1 | 0 | 0 | 0 | 3 | 3 | — |
| 46 | 2 | 0.28 | 0 | 0 | 0 | 0 | 0 | 0 | 0 | 0 | 0 | 0 | 0 | 0 | 0 | 0 | 2 | — |
| 46 | 2 | 0.056 | 0 | 0 | 0 | 0 | 0 | 0 | 0 | 0 | 0 | 0 | 0 | 0 | 0 | 0 | 1 | — |
| 47 | 2 | 5.6 | 1 | 3 | 3 | 3 | 3 | 1 | 3 | 3 | 3 | 3 | 3 | 3 | 3 | 3 | 3 | 3 |
| 47 | 2 | 1.12 | 0 | 2 | 0 | 2 | 3 | 0 | 2 | 3 | 3 | 3 | 3 | 1 | 3 | 3 | 3 | 3 |
| 47 | 2 | 0.28 | 0 | 2 | 0 | 0 | 0 | 0 | 2 | 0 | 1 | 2 | 3 | 0 | 0 | 1 | 3 | 3 |
| 47 | 2 | 0.056 | 0 | 1 | 0 | 0 | 0 | 0 | 0 | 0 | 0 | 1 | 3 | 0 | 0 | 0 | 3 | 3 |
| 47 | 2 | 0.0112 | 0 | 0 | 0 | 0 | 0 | 0 | 0 | 0 | 0 | 0 | — | 0 | 0 | 0 | 0 | 1 |
| 48 | 2 | 5.6 | 1 | 2 | 3 | 3 | 3 | 0 | 2 | 3 | 3 | 3 | 3 | 3 | 3 | 3 | 3 | 3 |
| 48 | 2 | 1.12 | 0 | 2 | 2 | 2 | 2 | 0 | 2 | 0 | 0 | 2 | 1 | 0 | 3 | 3 | 3 | 3 |
| 48 | 2 | 0.28 | 0 | 2 | 0 | 2 | 0 | 1 | 1 | 0 | — | 0 | 1 | 0 | 1 | 2 | 2 | 3 |
| 48 | 2 | 0.056 | 0 | 0 | 0 | 0 | 0 | 0 | 0 | 0 | 0 | 0 | 0 | 0 | 1 | 3 | 2 | 2 |
| 48 | 2 | 0.0112 | 0 | 0 | 0 | 0 | 0 | 0 | 0 | 0 | — | 0 | — | 0 | 1 | 0 | 0 | 2 |
| 49 | 2 | 5.6 | 0 | 2 | 2 | 2 | 3 | 0 | 3 | 3 | 2 | 3 | — | 1 | 3 | 3 | 3 | 3 |
| 49 | 2 | 1.12 | 0 | 1 | 0 | 1 | 1 | 0 | 0 | 0 | 0 | 2 | — | 0 | 1 | 2 | 3 | 2 |
| 49 | 2 | 0.28 | 0 | 0 | 0 | 0 | 0 | 0 | 0 | 0 | 0 | 1 | — | 0 | 0 | 0 | 0 | 0 |
| 49 | 2 | 0.056 | 0 | 0 | 0 | 0 | 0 | 0 | 0 | 0 | 0 | 0 | — | 0 | 0 | 0 | 0 | 0 |
| 50 | 2 | 5.6 | — | 3 | 3 | 3 | 3 | 2 | 3 | 2 | 3 | 3 | 3 | 0 | 3 | 3 | 3 | 3 |
| 50 | 2 | 1.12 | — | 2 | 1 | 3 | 3 | 0 | 2 | 0 | 2 | 3 | 2 | 0 | 3 | 3 | 3 | 3 |
| 50 | 2 | 0.28 | 0 | 1 | 0 | 2 | 0 | 0 | 0 | 0 | 1 | 2 | — | 0 | 3 | 3 | 3 | 3 |
| 50 | 2 | 0.056 | — | 1 | 0 | 1 | 0 | 0 | 0 | 0 | 3 | 1 | — | 0 | 2 | 2 | 3 | 3 |
| 50 | 2 | 0.0112 | — | 1 | 0 | 0 | 0 | 0 | 0 | 0 | 3 | 0 | — | 0 | 0 | 0 | 3 | 2 |
| 51 | 2 | 5.6 | — | 3 | 1 | 3 | 2 | 0 | 1 | 2 | 2 | 3 | 2 | 0 | 3 | 3 | 3 | 3 |
| 51 | 2 | 1.12 | 0 | 1 | 0 | 0 | 0 | 1 | 0 | 0 | 2 | 2 | — | 0 | 1 | 1 | 3 | 3 |
| 51 | 2 | 0.28 | 0 | 0 | 0 | 0 | 0 | 0 | 0 | 0 | 0 | 1 | — | 0 | 0 | 1 | 3 | 3 |
| 51 | 2 | 0.056 | — | 0 | 0 | 0 | 0 | 0 | 0 | 0 | 0 | 0 | — | 1 | 0 | 0 | 0 | 1 |
| 51 | 2 | 0.0112 | 0 | 1 | 0 | 0 | 0 | 0 | 1 | 0 | 1 | 2 | — | 0 | 0 | 0 | 1 | 3 |
| 54 | 2 | 5.6 | 1 | 2 | 3 | 3 | 3 | 3 | 3 | 3 | 3 | 3 | 2 | 3 | 1 | 3 | 3 | 3 |
| 54 | 2 | 1.12 | 0 | 1 | 2 | 3 | 3 | 0 | 1 | 3 | 2 | 0 | 2 | 0 | 3 | 3 | 3 | 3 |
| 54 | 2 | 0.28 | 0 | 1 | 1 | 3 | 1 | — | 1 | 0 | 0 | 0 | 1 | 0 | 2 | 2 | 3 | 3 |
| 54 | 2 | 0.056 | 0 | 0 | 0 | 2 | 0 | 0 | 0 | 0 | 0 | 0 | 0 | 0 | 2 | 2 | 2 | 3 |
| 54 | 2 | 0.0112 | 0 | 0 | 0 | 1 | 0 | — | 0 | 0 | 2 | 0 | 0 | 0 | 0 | 0 | 1 | 0 |
| 55 | 2 | 5.6 | 0 | 1 | 3 | 3 | 3 | 0 | 0 | 1 | 2 | 2 | 2 | 1 | 3 | 3 | 3 | 3 |
| 55 | 2 | 1.12 | 0 | 1 | 1 | 3 | 3 | 0 | 0 | 0 | 2 | 0 | 0 | 0 | 3 | 3 | 3 | 3 |
| 55 | 2 | 0.28 | 0 | 1 | 0 | 0 | 0 | 0 | 1 | 1 | 0 | 0 | 0 | 0 | 1 | 2 | 3 | 3 |
| 55 | 2 | 0.056 | 0 | 0 | 0 | 0 | 0 | 0 | 0 | 0 | 0 | 0 | 0 | 0 | 0 | 1 | 3 | 3 |
| 55 | 2 | 0.0112 | 0 | 0 | 0 | 0 | 0 | 0 | 0 | 0 | 0 | 1 | 0 | 0 | 0 | 0 | 1 | 2 |
| 56 | 2 | 5.6 | 0 | 3 | 3 | 3 | 3 | 0 | 1 | 3 | 3 | 3 | 2 | 1 | 3 | 3 | 3 | 3 |
| 56 | 2 | 1.12 | 0 | 2 | 3 | 2 | 3 | 0 | 1 | 3 | 3 | 1 | 1 | 0 | 3 | 3 | 3 | 3 |
| 56 | 2 | 0.28 | 0 | 2 | 2 | 2 | 1 | — | 0 | 3 | 3 | 1 | 0 | 1 | 2 | 3 | 3 | 3 |
| 56 | 2 | 0.056 | 0 | 1 | 1 | 1 | 0 | 0 | 0 | 0 | 0 | 0 | 0 | 0 | 0 | 2 | 3 | 3 |
| 56 | 2 | 0.0112 | 0 | 0 | 0 | 1 | 0 | 0 | 0 | 0 | — | 0 | 0 | 0 | 0 | 1 | 2 | 3 |
| 57 | 2 | 5.6 | 1 | 3 | 3 | 3 | 3 | 1 | 2 | 2 | 3 | 3 | 3 | 1 | 3 | 3 | 3 | 3 |
| 57 | 2 | 1.12 | 1 | 2 | 2 | 1 | 1 | 0 | 0 | 0 | 3 | 2 | 0 | 0 | 1 | 2 | 3 | 3 |
| 57 | 2 | 0.28 | 1 | 2 | 1 | 2 | 1 | 0 | 0 | 0 | 3 | 0 | 0 | 0 | 0 | 1 | 3 | 3 |
| 57 | 2 | 0.056 | 0 | 0 | 0 | 1 | 1 | 0 | 0 | 0 | 3 | 0 | 0 | 0 | 0 | 0 | 2 | 3 |
| 57 | 2 | 0.0112 | 0 | 0 | 0 | 0 | 0 | 0 | 0 | 0 | 0 | 0 | 0 | 0 | 0 | 1 | 1 | 2 |
| 58 | 2 | 5.6 | 0 | 2 | 3 | 3 | 3 | 0 | 2 | 3 | 3 | 3 | 2 | 1 | 3 | 3 | 3 | 3 |
| 58 | 2 | 1.12 | 0 | 2 | 3 | 3 | 1 | 0 | 0 | 1 | 3 | 2 | 2 | 1 | 3 | 3 | 3 | 3 |
| 58 | 2 | 0.28 | 0 | 1 | 2 | 2 | 2 | 0 | 1 | 1 | 3 | 0 | 0 | 2 | 3 | 3 | 3 | 3 |
| 58 | 2 | 0.056 | 0 | 0 | 0 | 1 | 1 | 0 | 0 | 0 | 0 | 0 | 0 | 0 | 0 | 1 | 2 | 3 |
| 58 | 2 | 0.0112 | 0 | 0 | 0 | 0 | 0 | 0 | 0 | 0 | 0 | 0 | 0 | 0 | 0 | 0 | 1 | 2 |
| 59 | 2 | 5.6 | 2 | 2 | 3 | 3 | 3 | 2 | 2 | 3 | 1 | 3 | 3 | 2 | 3 | 3 | 3 | 3 |
| 59 | 2 | 1.12 | 0 | 2 | 1 | 1 | 2 | 0 | 1 | 0 | 1 | 1 | 0 | 0 | 3 | 3 | 3 | 3 |

TABLE X-continued

| Compound No. | WAT | kg/h | L | M | N | O | P | B | Q | D | R | E | F | C | J | S | K | T |
|---|---|---|---|---|---|---|---|---|---|---|---|---|---|---|---|---|---|---|
| 59 | 2 | 0.28 | 0 | 1 | 0 | 0 | 1 | 0 | 0 | 0 | 0 | 3 | 1 | 0 | 1 | 1 | 3 | 3 |
| 59 | 2 | 0.056 | 0 | 0 | 0 | 0 | 0 | 0 | 0 | 0 | 0 | 1 | 0 | 0 | 0 | 1 | 2 | 3 |
| 59 | 2 | 0.0112 | 0 | 0 | 0 | 0 | 0 | 0 | 0 | 0 | 0 | 0 | 0 | 0 | 0 | 0 | 1 | 2 |
| 60 | 2 | 5.6 | 0 | 2 | 2 | 3 | 3 | 0 | 1 | 1 | 2 | 3 | 2 | 1 | 3 | 3 | 3 | 3 |
| 60 | 2 | 1.12 | 0 | 2 | 2 | 2 | 2 | 0 | 1 | 0 | 3 | 2 | 2 | 0 | 2 | 3 | 3 | 3 |
| 60 | 2 | 0.28 | 0 | 0 | 0 | 0 | 0 | 0 | 0 | 0 | 3 | 2 | 0 | 0 | 1 | 2 | 3 | 3 |
| 60 | 2 | 0.056 | 0 | 0 | 0 | 0 | 0 | 0 | 0 | 0 | 0 | 0 | 0 | 0 | 0 | 2 | 3 | 2 |
| 61 | 2 | 5.6 | 0 | 1 | 0 | 3 | 0 | 0 | 1 | 0 | 1 | 2 | 2 | 0 | 3 | 3 | 3 | — |
| 61 | 2 | 1.12 | 0 | 1 | 0 | 2 | 0 | 0 | 0 | 0 | 1 | 1 | 2 | 0 | 3 | 3 | 3 | — |
| 61 | 2 | 0.28 | 0 | 0 | 0 | 0 | 0 | 0 | 0 | 0 | 1 | 0 | 0 | 0 | 0 | 0 | 2 | — |
| 61 | 2 | 0.056 | 0 | 0 | 0 | 0 | 0 | 0 | 0 | 0 | 0 | 0 | 0 | 0 | 0 | 0 | 1 | — |
| 62 | 2 | 5.6 | 0 | 1 | 2 | 3 | 1 | 0 | 1 | 0 | 0 | 1 | 3 | 0 | 3 | 3 | 3 | — |
| 62 | 2 | 1.12 | 0 | 1 | 0 | 1 | 0 | 0 | 0 | 0 | 0 | 0 | 1 | 0 | 3 | 3 | 3 | — |
| 62 | 2 | 0.28 | 0 | 0 | 0 | 1 | 0 | 0 | 0 | 0 | 0 | 0 | 0 | 0 | 1 | 1 | 3 | — |
| 62 | 2 | 0.056 | 0 | 0 | 0 | 0 | 0 | 0 | 0 | 0 | 0 | 0 | 0 | 0 | 0 | 0 | 1 | — |
| 62 | 2 | 0.0112 | 0 | 0 | 0 | 0 | 0 | 0 | 0 | 0 | 0 | 0 | 0 | 0 | 0 | 0 | 0 | — |
| 63 | 2 | 5.6 | 1 | 2 | 3 | 3 | 3 | 1 | 1 | 2 | 2 | 3 | 3 | 2 | 3 | 3 | 3 | 3 |
| 63 | 2 | 1.12 | 0 | 1 | 0 | 3 | 1 | 0 | 0 | 0 | 3 | 2 | 1 | 0 | 3 | 3 | 3 | — |
| 63 | 2 | 0.28 | 0 | 0 | 1 | 2 | 1 | 0 | 0 | 0 | 0 | 1 | 0 | 0 | 2 | 2 | 3 | — |
| 63 | 2 | 0.056 | 0 | 0 | 0 | 0 | 0 | 0 | 0 | 0 | 0 | 0 | 0 | 0 | 0 | 0 | 3 | — |
| 63 | 2 | 0.0112 | 0 | 0 | 0 | 0 | 0 | 0 | 0 | 0 | 0 | 0 | 0 | 0 | 0 | 0 | 1 | — |
| 64 | 2 | 5.6 | 0 | 1 | 1 | 2 | 2 | 0 | 0 | 0 | 1 | 1 | 0 | 0 | 2 | 2 | 3 | — |
| 64 | 2 | 1.12 | 0 | 0 | 0 | 0 | 0 | 0 | 0 | 0 | 0 | 0 | 0 | 0 | 2 | 0 | 3 | — |
| 64 | 2 | 0.28 | 0 | 1 | 0 | 1 | 0 | 0 | 0 | 0 | 0 | 0 | 0 | 0 | 1 | 0 | 2 | — |
| 65 | 2 | 5.6 | 2 | 2 | 3 | 3 | 3 | 1 | 2 | 2 | 2 | 3 | 3 | 2 | 3 | 3 | 3 | — |
| 65 | 2 | 1.12 | 0 | 1 | 2 | 3 | 2 | 0 | 1 | 0 | 0 | 1 | 0 | 0 | 3 | 3 | 3 | — |
| 65 | 2 | 0.28 | 0 | 0 | 1 | 1 | 1 | 0 | 0 | 0 | 0 | 0 | 0 | 0 | 3 | 0 | 3 | — |
| 65 | 2 | 0.056 | 0 | 0 | 0 | 0 | 0 | 0 | 0 | 0 | 0 | 0 | 0 | 0 | 1 | 0 | 3 | — |
| 65 | 2 | 0.0112 | 0 | 0 | 0 | 0 | 0 | 0 | 0 | 0 | 0 | 0 | 0 | 0 | 0 | 0 | 0 | — |
| 66 | 2 | 5.6 | 1 | 0 | 0 | 2 | 1 | 0 | 1 | 0 | 0 | 1 | 1 | 0 | 2 | 3 | 3 | — |
| 66 | 2 | 1.12 | 0 | 0 | 0 | 0 | 0 | 0 | 1 | 0 | 0 | 3 | 0 | 0 | 1 | 2 | 3 | — |
| 66 | 2 | 0.28 | 0 | 0 | 0 | 0 | 0 | 0 | 0 | 0 | 0 | 0 | 0 | 0 | 0 | 0 | 2 | — |
| 67 | 2 | 5.6 | 1 | 0 | 0 | 1 | 0 | 0 | 0 | 0 | 0 | 0 | 0 | 1 | 1 | 3 | 3 | — |
| 67 | 2 | 1.12 | 0 | 0 | 0 | 0 | 0 | 0 | 0 | 0 | 0 | 0 | 0 | 0 | 0 | 1 | 1 | — |
| 67 | 2 | 0.28 | 0 | 0 | 0 | 0 | 0 | 0 | 0 | 0 | 0 | 0 | 0 | 0 | 0 | 0 | 0 | — |
| 67 | 2 | 0.056 | 0 | 0 | 0 | 0 | 0 | 0 | 0 | 0 | 0 | 0 | 0 | 0 | 0 | 0 | 0 | — |
| 68 | 2 | 5.6 | 1 | 2 | 3 | 3 | 3 | 0 | 2 | 3 | 2 | 3 | — | 1 | 3 | 3 | 3 | 3 |
| 68 | 2 | 1.12 | 0 | 2 | 1 | 1 | 2 | 0 | 1 | 3 | 2 | 3 | — | 1 | 3 | 3 | 3 | 3 |
| 68 | 2 | 0.28 | 0 | 1 | 1 | 0 | 1 | 0 | 0 | 1 | 1 | 2 | — | 0 | 2 | 2 | 3 | 3 |
| 68 | 2 | 0.056 | 0 | 0 | 0 | 0 | 0 | 0 | 0 | 0 | 0 | 0 | 0 | 0 | 1 | 1 | 3 | 1 |
| 68 | 2 | 0.0112 | 0 | 0 | 0 | 0 | 0 | 0 | 0 | 0 | 0 | — | 0 | 0 | 0 | 1 | 0 |
| 69 | 2 | 5.6 | 0 | 0 | 1 | 3 | 3 | 3 | 0 | 1 | 0 | 2 | 0 | 0 | 3 | 3 | 3 | 3 |
| 69 | 2 | 1.12 | 0 | 0 | 0 | 0 | 0 | 0 | 0 | 0 | 3 | 1 | 1 | 0 | 1 | 0 | 3 | 3 |
| 69 | 2 | 0.28 | 0 | 0 | 0 | 0 | 0 | 0 | 0 | 0 | 3 | 0 | 0 | 0 | 0 | 0 | 2 | 3 |
| 69 | 2 | 0.056 | 0 | 0 | 0 | 0 | 0 | 0 | 0 | 0 | 1 | 0 | 0 | 0 | 0 | 1 | 1 | 1 |
| 70 | 2 | 5.6 | 1 | 3 | 3 | 3 | 3 | 2 | 3 | 3 | 3 | 3 | 2 | 2 | 3 | 3 | 3 | 3 |
| 70 | 2 | 1.12 | 0 | 2 | 1 | 3 | 3 | 1 | 2 | 3 | 3 | 3 | 1 | 2 | 2 | 3 | 3 | 3 |
| 70 | 2 | 0.28 | 0 | 1 | 0 | 1 | 2 | 0 | 3 | 0 | 3 | 3 | 1 | 0 | 1 | 2 | 3 | 3 |
| 70 | 2 | 0.056 | 0 | 0 | 0 | 0 | 1 | 0 | 0 | 0 | 0 | 0 | 0 | 0 | 0 | 0 | 2 | 3 |
| 70 | 2 | 0.0112 | 0 | 0 | 0 | 0 | 0 | 0 | 0 | 0 | 1 | 1 | 0 | 0 | 0 | 0 | 1 | 3 |
| 71 | 2 | 5.6 | 2 | 2 | 2 | 3 | 3 | 1 | 3 | 3 | 3 | 3 | 3 | 2 | 3 | 3 | 3 | 3 |
| 71 | 2 | 1.12 | 1 | 3 | 2 | 2 | 3 | 1 | 3 | 3 | 3 | 3 | 3 | 1 | 3 | 3 | 3 | 3 |
| 71 | 2 | 0.28 | 1 | 2 | 1 | 1 | 2 | 0 | 3 | 1 | 1 | 3 | 1 | 0 | 1 | 3 | 3 | 3 |
| 71 | 2 | 0.056 | 0 | 0 | 0 | 0 | 1 | 0 | 0 | 3 | 0 | 2 | 0 | 0 | 0 | 1 | 1 | 2 |
| 71 | 2 | 0.0112 | 0 | 0 | 0 | 0 | 0 | 0 | 0 | 0 | 0 | 0 | 0 | 0 | 0 | 1 | 1 | 2 |
| 72 | 2 | 5.6 | 1 | 2 | 3 | 3 | 3 | 0 | 2 | 3 | 2 | 3 | 3 | 1 | 3 | 3 | 3 | 3 |
| 72 | 2 | 1.12 | 2 | 2 | 3 | 3 | 3 | 0 | 1 | 2 | 2 | 3 | 3 | 1 | 3 | 3 | 3 | 3 |
| 72 | 2 | 0.28 | 0 | 1 | 0 | 1 | 3 | 0 | 2 | 0 | 2 | 3 | 2 | 0 | 1 | 3 | 3 | 3 |
| 72 | 2 | 0.056 | 0 | 1 | 0 | 1 | 1 | 0 | 0 | 0 | 0 | 2 | 1 | 0 | 1 | 1 | 3 | 3 |
| 72 | 2 | 0.0112 | 0 | 0 | 0 | 0 | 0 | 0 | 0 | 0 | 1 | 1 | 0 | 0 | 0 | 1 | 3 |
| 73 | 2 | 5.6 | 2 | 3 | 3 | 3 | 3 | 1 | 2 | 3 | 3 | 3 | 3 | 2 | 3 | 3 | 3 | 3 |
| 73 | 2 | 1.12 | 1 | 3 | 3 | 3 | 3 | 1 | 2 | 2 | 2 | 3 | 3 | 1 | 3 | 3 | 3 | 3 |
| 73 | 2 | 0.28 | 0 | 1 | 2 | 1 | 2 | 0 | 1 | 1 | 0 | 3 | 0 | 2 | 2 | 3 | 3 | 3 |
| 73 | 2 | 0.056 | 0 | 1 | 0 | 0 | 1 | 0 | 1 | 1 | 3 | 3 | 0 | 0 | 1 | 1 | 2 | 3 |
| 73 | 2 | 0.0112 | 0 | 0 | 0 | 0 | 0 | 0 | 0 | 0 | 0 | 1 | 2 | 0 | 0 | 0 | 2 | 3 |
| 74 | 2 | 5.6 | 2 | 2 | 1 | 3 | 3 | 0 | 0 | 1 | 1 | 3 | 2 | 0 | 3 | 3 | 3 | 3 |
| 74 | 2 | 1.12 | 0 | 1 | 0 | 2 | 2 | 0 | 0 | 0 | 3 | 2 | 3 | 0 | 3 | 3 | 3 | 3 |
| 74 | 2 | 0.28 | 0 | 0 | 0 | 0 | 0 | 0 | 0 | 0 | 0 | 0 | 1 | 0 | 0 | 1 | 2 | 3 |
| 74 | 0 | 0.056 | 0 | 1 | 0 | 0 | 0 | 0 | 0 | 0 | 0 | 3 | 0 | 0 | 0 | 0 | 1 | 2 |
| 75 | 2 | 5.6 | 1 | 1 | 1 | 2 | 3 | 1 | 1 | 1 | 1 | 3 | 3 | 0 | 3 | 3 | 3 | 3 |
| 75 | 2 | 1.12 | 0 | 0 | 1 | 0 | 0 | 0 | 0 | 0 | 2 | 3 | 2 | 0 | 0 | 1 | 3 | 3 |
| 75 | 2 | 0.28 | 0 | 0 | 0 | 0 | 0 | 0 | 0 | 0 | 1 | 1 | 0 | 0 | 0 | 2 | 2 | 3 |
| 75 | 2 | 0.056 | 0 | 0 | 0 | 0 | 0 | 0 | 0 | 0 | 0 | 1 | 0 | 0 | 0 | 0 | 1 | 2 |
| 76 | 2 | 5.6 | 3 | 2 | 3 | 3 | 3 | 2 | 3 | 3 | 3 | 3 | 3 | 3 | 3 | 3 | 3 | 3 |
| 76 | 2 | 1.12 | 2 | 2 | 3 | 3 | 3 | 1 | 2 | 3 | 3 | 3 | 2 | 3 | 3 | 3 | 3 | 3 |
| 76 | 2 | 0.28 | 1 | 2 | 1 | 3 | 3 | 0 | 1 | 0 | 2 | 3 | 2 | 2 | 2 | 3 | 3 | 3 |
| 76 | 2 | 0.056 | 0 | 1 | 2 | 3 | 3 | 0 | 1 | 0 | 2 | 3 | 1 | 3 | 2 | 3 | 3 | 3 |
| 76 | 2 | 0.0112 | 0 | 1 | 0 | 1 | 0 | 0 | 1 | 0 | 2 | 2 | 0 | 1 | 0 | 3 | 2 | 3 |
| 76 | 2 | 0.0056 | 0 | 0 | 0 | 0 | 0 | 0 | 0 | 0 | 2 | 2 | 0 | 0 | 0 | 1 | 2 |
| 77 | 2 | 5.6 | 2 | 3 | 3 | 3 | 3 | 0 | 2 | 3 | 3 | 3 | 3 | 3 | 3 | 3 | 3 | 3 |

TABLE X-continued

| Compound No. | WAT | kg/h | Plant Species | | | | | | | | | | | | | | | |
|---|---|---|---|---|---|---|---|---|---|---|---|---|---|---|---|---|---|---|
| | | | L | M | N | O | P | B | Q | D | R | E | F | C | J | S | K | T |
| 77 | 2 | 1.12 | 0 | 2 | 3 | 3 | 3 | 0 | 2 | 1 | 3 | 3 | 2 | 3 | 3 | 3 | 3 | 3 |
| 77 | 2 | 0.28 | 1 | 1 | 0 | 1 | 0 | 0 | 1 | 0 | 2 | 1 | 2 | 0 | 1 | 1 | 3 | 3 |
| 77 | 2 | 0.056 | 0 | 0 | 1 | 1 | 0 | 0 | 0 | 0 | 0 | 0 | 1 | 0 | 0 | 0 | 3 | 3 |
| 77 | 2 | 0.0112 | 0 | 0 | 0 | 0 | 0 | 0 | 0 | 0 | 0 | 0 | 0 | 0 | 0 | 0 | 0 | 3 |
| 78 | 2 | 5.6 | 2 | 3 | 3 | 3 | 3 | 2 | 3 | 3 | 3 | 3 | 3 | 3 | 3 | 3 | 3 | 3 |
| 78 | 2 | 1.12 | 0 | 2 | 2 | 3 | 3 | 0 | 2 | 3 | 2 | 3 | 2 | 2 | 3 | 3 | 3 | 3 |
| 78 | 2 | 0.28 | 0 | 1 | 2 | 3 | 3 | 0 | 1 | 1 | 1 | 3 | 1 | 0 | 3 | 3 | 3 | 3 |
| 78 | 2 | 0.056 | 0 | 1 | 0 | 1 | 0 | 0 | 1 | 0 | 0 | 0 | 0 | 0 | 2 | 2 | 3 | 3 |
| 78 | 2 | 0.0112 | 0 | 1 | 0 | 0 | 0 | 0 | 1 | 0 | 0 | 0 | 0 | 0 | 0 | 0 | 2 | 3 |
| 79 | 2 | 5.6 | 0 | 1 | 0 | 1 | 0 | 3 | 0 | 0 | 0 | 1 | 1 | 0 | 1 | 2 | 2 | 3 |
| 79 | 2 | 1.12 | 0 | 0 | 0 | 0 | 0 | 0 | 0 | 0 | 3 | 0 | 0 | 0 | 0 | 1 | 1 | 3 |
| 79 | 2 | 0.28 | 0 | 0 | 0 | 0 | 0 | 0 | 0 | — | 3 | 0 | 0 | 0 | 0 | 0 | 0 | 2 |
| 79 | 2 | 0.056 | 0 | 0 | 0 | 0 | 0 | — | 0 | 0 | 0 | 0 | 0 | 0 | 0 | 0 | 0 | 2 |
| 80 | 2 | 5.6 | 2 | 3 | 3 | 3 | 3 | 3 | 1 | 3 | 2 | 3 | 3 | 1 | 3 | 3 | 3 | 3 |
| 80 | 2 | 1.12 | 0 | 2 | 3 | 3 | 3 | 0 | 0 | 2 | 1 | 2 | 1 | 0 | 3 | 3 | 3 | 3 |
| 80 | 2 | 0.28 | 0 | 1 | 1 | 1 | 3 | — | 0 | 1 | — | 3 | 1 | 0 | 3 | 3 | 3 | 3 |
| 80 | 2 | 0.056 | 0 | 0 | 0 | 1 | 1 | — | 0 | 0 | — | 2 | 0 | 0 | 1 | 1 | 2 | 2 |
| 80 | 2 | 0.0112 | 0 | 0 | 0 | 0 | 0 | 0 | 0 | 0 | — | 0 | 0 | 0 | 0 | 0 | 1 | 1 |
| 81 | 2 | 5.6 | 1 | 3 | 3 | 3 | 3 | 1 | 2 | 3 | 3 | 3 | 3 | 2 | 3 | 3 | 3 | 3 |
| 81 | 2 | 1.12 | 0 | 2 | 1 | 3 | 2 | 1 | 0 | 1 | 3 | 3 | 3 | 1 | 3 | 3 | 3 | 3 |
| 81 | 2 | 0.28 | 0 | 1 | 0 | 1 | 2 | 0 | 0 | 0 | 3 | 2 | 3 | 0 | 2 | 3 | 3 | 3 |
| 81 | 2 | 0.056 | 0 | 0 | 0 | 0 | 0 | 0 | 0 | 0 | 3 | 1 | 2 | 0 | 0 | 0 | 2 | 2 |
| 81 | 2 | 0.0112 | 0 | 0 | 0 | 0 | 0 | 0 | 0 | 0 | 0 | 0 | 1 | 0 | 0 | 0 | 0 | 1 |
| 82 | 2 | 5.6 | 1 | 3 | 1 | 2 | 1 | 0 | 1 | 1 | 1 | 3 | 3 | 0 | 3 | 3 | 3 | — |
| 82 | 2 | 1.12 | 0 | 2 | 0 | 2 | 0 | 0 | 0 | 1 | 1 | 1 | 2 | 0 | 3 | 2 | 3 | — |
| 82 | 2 | 0.28 | 0 | 1 | 0 | 0 | 0 | 0 | 0 | 0 | 0 | 0 | 0 | 0 | 1 | 0 | 3 | — |
| 82 | 2 | 0.056 | 0 | 0 | 0 | 0 | 0 | 0 | 0 | 0 | 0 | 0 | 0 | 0 | 0 | 0 | 1 | — |
| 83 | 2 | 5.6 | 1 | 2 | 3 | 3 | 3 | 1 | 2 | 1 | 2 | 2 | 2 | 2 | 3 | 3 | 3 | — |
| 83 | 2 | 1.12 | 0 | 2 | 2 | 2 | 0 | 0 | 3 | 0 | 2 | 1 | 0 | 0 | 3 | 3 | 3 | — |
| 83 | 2 | 0.28 | 0 | 0 | 1 | 2 | 0 | 0 | 0 | 0 | 1 | 1 | 0 | 0 | 1 | 2 | 3 | — |
| 83 | 2 | 0.056 | 0 | 0 | 0 | 0 | 0 | 0 | 0 | 0 | 0 | 0 | 0 | 0 | 0 | 0 | 2 | — |
| 83 | 2 | 0.0112 | 0 | 0 | 0 | 0 | 0 | 0 | 0 | 0 | 0 | 0 | 0 | 0 | 0 | 0 | 2 | — |
| 84 | 2 | 5.6 | 0 | 2 | 0 | 1 | 0 | 1 | 0 | 0 | 0 | 2 | 1 | 0 | 0 | 2 | 3 | — |
| 84 | 2 | 1.12 | 0 | 0 | 0 | 0 | 0 | 0 | 0 | 0 | 0 | 2 | 0 | 0 | 0 | 3 | 3 | — |
| 84 | 2 | 0.28 | 0 | 0 | 0 | 0 | 0 | 0 | 0 | 0 | 0 | 0 | 0 | 0 | 0 | 0 | 0 | — |
| 85 | 2 | 5.6 | 1 | 3 | 2 | 2 | 3 | 1 | 3 | 3 | 3 | 3 | 3 | 2 | 3 | 3 | 3 | 3 |
| 85 | 2 | 1.12 | 0 | 2 | 1 | 2 | 2 | 0 | 2 | 0 | 2 | 3 | 3 | 1 | 2 | 3 | 3 | 3 |
| 85 | 2 | 0.28 | 0 | 1 | 0 | 0 | 0 | 0 | 0 | 0 | 2 | 1 | 1 | 0 | 1 | 3 | 3 | 3 |
| 85 | 2 | 0.056 | 0 | 0 | 0 | 0 | 0 | 0 | 0 | 0 | 0 | 0 | 3 | 0 | 0 | 0 | 2 | 3 |
| 85 | 2 | 0.0112 | 0 | 0 | 0 | 0 | 0 | 0 | 0 | 0 | — | 0 | 1 | 0 | 0 | 0 | 0 | 2 |
| 86 | 2 | 5.6 | 0 | 2 | 2 | 3 | 3 | 0 | 1 | 2 | 1 | 3 | — | 1 | 3 | 3 | 3 | 3 |
| 86 | 2 | 1.12 | 0 | 1 | 0 | 0 | 1 | 0 | 0 | 0 | 0 | 1 | — | 0 | 0 | 1 | 2 | 3 |
| 86 | 2 | 0.28 | 0 | 0 | 0 | 1 | 1 | 0 | 0 | 0 | 0 | 3 | — | 0 | 1 | 2 | 2 | 3 |
| 86 | 2 | 0.56 | 0 | 0 | 0 | 0 | 0 | 0 | 0 | 0 | 0 | 0 | — | 0 | 0 | 0 | 0 | 1 |
| 87 | 2 | 5.6 | 0 | 2 | 3 | 3 | 3 | 1 | 2 | 3 | 2 | 3 | — | 1 | 3 | 3 | 3 | 3 |
| 87 | 2 | 1.12 | 0 | 2 | 1 | 2 | 2 | 0 | 1 | 3 | 2 | 3 | — | 0 | 1 | 3 | 3 | 3 |
| 87 | 2 | 0.28 | 0 | 1 | 1 | 1 | 1 | 0 | 0 | 0 | 1 | 2 | — | 0 | 0 | 2 | 3 | 3 |
| 87 | 2 | 0.056 | 0 | 0 | 0 | 0 | 0 | 0 | 0 | 0 | 0 | 0 | — | 0 | 0 | 1 | 2 | 1 |
| 90 | 2 | 5.6 | 0 | 3 | 3 | 3 | 3 | 0 | 3 | 3 | 3 | 3 | 2 | 1 | 3 | 3 | 3 | 3 |
| 90 | 2 | 1.12 | 1 | 2 | 3 | 3 | 3 | 0 | 0 | 2 | 3 | 3 | 2 | 0 | 3 | 3 | 3 | 3 |
| 90 | 2 | 0.28 | 1 | 2 | 1 | 3 | 0 | 0 | 1 | 0 | 3 | 2 | 2 | 0 | 1 | 3 | 3 | 3 |
| 90 | 2 | 0.056 | 0 | 0 | 0 | 0 | 0 | 0 | 0 | 0 | 0 | 0 | 0 | 0 | 0 | 0 | 1 | 2 |
| 90 | 2 | 0.0112 | 0 | 0 | 0 | 0 | 0 | 0 | 0 | 0 | 0 | 0 | 0 | 0 | 0 | 0 | 0 | 0 |
| 92 | 2 | 5.6 | 0 | 1 | 0 | 0 | 0 | 0 | 0 | 0 | 3 | 2 | 1 | 0 | 0 | 0 | 3 | 2 |
| 92 | 2 | 1.12 | 0 | 1 | 0 | 0 | 0 | 0 | 2 | 0 | 2 | 0 | 0 | 0 | 0 | — | 3 | 3 |
| 92 | 2 | 0.28 | 0 | 0 | 0 | 0 | 0 | 0 | 0 | 0 | 1 | 0 | 0 | 0 | 0 | 0 | 2 | 1 |
| 93 | 2 | 5.6 | 0 | 2 | 1 | 2 | 3 | 0 | 1 | 0 | 0 | 2 | 1 | 0 | 3 | 3 | 3 | 3 |
| 93 | 2 | 1.12 | 0 | 0 | 0 | 0 | 0 | 0 | 0 | 0 | 2 | 1 | 1 | 0 | 0 | 1 | 3 | 3 |
| 93 | 2 | 0.28 | 0 | 0 | 0 | 0 | 0 | 0 | 1 | 0 | 0 | 0 | 0 | 0 | 1 | 1 | 3 | 3 |
| 93 | 2 | 0.056 | 0 | 0 | 0 | 0 | 0 | 0 | 0 | 0 | 0 | 0 | 0 | 0 | 0 | 0 | 1 | 2 |
| 94 | 2 | 5.6 | 0 | 1 | 0 | 2 | 3 | 0 | 1 | 0 | 0 | 3 | 2 | 0 | 3 | 3 | 3 | 3 |
| 94 | 2 | 1.12 | 0 | 1 | 0 | 0 | 0 | 0 | 0 | 0 | 0 | 1 | 0 | 0 | 1 | 3 | 3 | 3 |
| 94 | 2 | 0.28 | 0 | 1 | 0 | 0 | 0 | 0 | 1 | 0 | 0 | 2 | 1 | 0 | 0 | 1 | 3 | 3 |
| 94 | 2 | 0.56 | 1 | 1 | 0 | 0 | 0 | 0 | 0 | 0 | 1 | 1 | 1 | 0 | 0 | 0 | 3 | 3 |
| 95 | 2 | 5.6 | 0 | 2 | 3 | 3 | 3 | 0 | 3 | 2 | 3 | 3 | 3 | 1 | 3 | 3 | 3 | 3 |
| 95 | 2 | 1.12 | 1 | 1 | 1 | 1 | 2 | 0 | 1 | 1 | 1 | 3 | 3 | 0 | 3 | 3 | 3 | 3 |
| 95 | 2 | 0.28 | 0 | 1 | 0 | 0 | 3 | 0 | 0 | 0 | 0 | 3 | 1 | 0 | 2 | 3 | 3 | 3 |
| 95 | 2 | 0.056 | 0 | 1 | 0 | 0 | 2 | 0 | 0 | 0 | 0 | 0 | 0 | 0 | 0 | 0 | 3 | 3 |
| 95 | 2 | 0.0112 | 0 | 0 | 0 | 0 | 0 | 0 | 0 | 0 | 0 | 0 | 0 | 0 | 0 | 0 | 2 | 2 |
| 96 | 2 | 5.6 | 0 | 1 | 0 | 1 | 1 | 0 | 0 | 0 | 0 | 3 | 3 | 0 | 0 | 3 | 3 | 3 |
| 96 | 2 | 1.12 | 0 | 0 | 0 | 0 | 0 | 0 | 0 | 0 | 0 | 0 | 1 | 0 | 0 | 3 | 3 | 3 |
| 96 | 2 | 0.28 | 0 | 0 | 0 | 0 | 0 | 0 | 0 | 0 | 0 | 0 | 0 | 0 | 0 | 0 | 2 | 0 |
| 96 | 2 | 0.056 | 0 | 0 | 0 | 0 | 0 | 0 | 0 | 0 | 0 | 0 | 0 | 0 | 0 | 0 | 0 | 2 |
| 97 | 2 | 5.6 | 0 | 1 | 1 | 2 | 3 | 0 | 1 | 0 | 0 | 2 | 3 | 0 | 3 | 3 | 3 | 3 |
| 97 | 2 | 1.12 | 0 | 1 | 0 | 1 | 2 | 0 | 1 | 0 | 0 | 0 | 1 | 0 | 1 | 3 | 3 | 3 |
| 97 | 2 | 0.28 | 0 | 0 | 0 | 0 | 3 | 0 | 0 | 0 | 0 | 0 | 0 | 0 | 0 | 3 | 3 | 3 |
| 97 | 2 | 0.056 | 0 | 0 | 0 | 0 | 0 | 0 | 0 | 0 | 0 | 0 | 0 | 0 | 0 | 2 | 3 | 2 |
| 98 | 2 | 5.6 | 0 | 0 | 2 | 2 | 2 | 0 | 3 | 3 | 0 | 3 | 3 | 0 | 1 | 3 | 3 | 3 |
| 98 | 2 | 1.12 | 0 | 0 | 0 | 1 | 1 | 0 | 0 | 0 | 0 | 3 | 2 | 0 | 2 | 3 | 3 | 3 |
| 98 | 2 | 0.28 | 0 | 0 | 0 | 0 | 0 | 0 | 0 | 0 | 0 | 2 | 2 | 0 | 0 | 3 | 2 | 3 |

TABLE X-continued

| Compound No. | WAT | kg/h | L | M | N | O | P | B | Q | D | R | E | F | C | J | S | K | T |
|---|---|---|---|---|---|---|---|---|---|---|---|---|---|---|---|---|---|---|
| 98 | 2 | 0.056 | 0 | 0 | 0 | 0 | 0 | 0 | 0 | 0 | 0 | 0 | 0 | 0 | 0 | 0 | 0 | 0 |
| 99 | 2 | 5.6 | 1 | 2 | 3 | 3 | 3 | 1 | 3 | 2 | 3 | 3 | 3 | 2 | 3 | 3 | 3 | 3 |
| 99 | 2 | 1.12 | 0 | 1 | 3 | 3 | 3 | 0 | 1 | 2 | 2 | 3 | 2 | 1 | 3 | 3 | 3 | 3 |
| 99 | 2 | 0.28 | 0 | 1 | 0 | 0 | 3 | 0 | 1 | 0 | 2 | 3 | 1 | 0 | 2 | 3 | 3 | 3 |
| 99 | 2 | 0.056 | 0 | 0 | 0 | 0 | 0 | 0 | 0 | 0 | 0 | 2 | 0 | 0 | 0 | 2 | 3 | 1 |
| 99 | 2 | 0.0112 | 0 | 0 | 0 | 0 | 0 | 0 | 0 | 0 | 0 | 0 | 0 | 0 | 0 | 0 | 1 | 1 |
| 100 | 2 | 5.6 | 0 | 2 | 1 | 3 | 2 | 0 | 3 | 2 | 1 | 2 | 2 | 0 | 3 | 3 | 3 | 3 |
| 100 | 2 | 1.12 | 0 | 1 | 0 | 3 | 2 | 0 | 0 | 0 | 1 | 3 | 3 | 0 | 1 | 3 | 3 | 3 |
| 100 | 2 | 0.28 | 0 | 0 | 0 | 1 | 1 | 0 | 0 | 0 | 0 | 3 | 2 | 0 | 0 | 3 | 3 | 2 |
| 101 | 2 | 5.6 | 0 | 1 | 1 | 2 | 3 | 0 | 2 | 3 | 2 | 3 | 2 | 0 | 2 | 3 | 3 | 3 |
| 101 | 2 | 1.12 | 0 | 0 | 1 | 1 | 1 | 0 | 1 | 0 | 1 | 1 | 0 | 0 | 2 | 3 | 3 | 3 |
| 101 | 2 | 0.28 | 0 | 0 | 0 | 0 | 1 | 0 | 0 | 0 | 0 | 0 | 0 | 0 | 0 | 3 | 3 | 3 |
| 103 | 2 | 5.6 | 1 | 3 | 3 | 3 | 2 | 0 | 2 | 2 | 3 | 3 | 3 | 1 | 3 | 3 | 3 | 3 |
| 103 | 2 | 1.12 | 0 | 2 | 1 | 2 | 3 | 0 | 2 | 1 | 2 | 2 | 3 | 0 | 3 | 3 | 3 | 3 |
| 103 | 2 | 0.28 | 0 | 1 | 0 | 1 | 0 | 0 | 1 | 0 | 0 | 0 | 0 | 0 | 1 | 2 | 3 | 3 |
| 103 | 2 | 0.056 | 0 | 0 | 0 | 0 | 0 | 0 | 0 | 1 | 0 | 0 | 0 | 0 | 0 | 0 | 3 | 2 |
| 103 | 2 | 0.01 | 0 | 0 | 0 | 0 | 0 | 0 | 0 | 0 | 0 | 0 | 0 | 0 | 0 | 0 | 1 | 2 |
| 104 | 2 | 5.6 | 0 | 2 | 3 | 3 | 3 | 0 | 3 | 0 | 2 | 2 | 2 | 1 | 3 | 3 | 3 | 3 |
| 104 | 2 | 1.12 | 0 | 1 | 2 | 1 | 3 | 0 | 1 | 0 | 1 | 1 | 3 | 0 | 3 | 3 | 3 | 3 |
| 104 | 2 | 0.28 | 0 | 0 | 0 | 2 | 1 | 0 | 1 | 0 | 0 | 0 | 0 | 0 | 3 | 3 | 3 | 3 |
| 104 | 2 | 0.056 | 0 | 0 | 0 | 0 | 0 | 0 | 0 | 0 | 0 | 0 | 0 | 0 | 1 | 2 | 3 | 2 |
| 104 | 2 | 0.01 | 0 | 1 | 0 | 0 | 0 | 0 | 0 | 0 | 0 | 0 | 0 | 0 | 1 | 1 | 3 | 2 |
| 105 | 2 | 5.6 | 0 | 2 | 2 | 3 | 3 | 0 | 3 | 2 | 2 | 3 | — | 1 | 3 | 3 | 3 | 3 |
| 105 | 2 | 1.12 | 0 | 2 | 2 | 2 | 3 | 0 | 1 | 0 | 0 | 1 | — | 0 | 3 | 3 | 3 | 3 |
| 105 | 2 | 0.28 | 0 | 1 | 1 | 1 | 1 | 0 | 0 | 0 | 0 | 0 | — | 0 | 1 | 2 | 3 | 3 |
| 105 | 2 | 0.056 | 0 | 1 | 1 | 0 | 0 | 0 | 0 | 0 | 0 | 0 | — | 0 | 0 | 0 | 3 | 3 |
| 105 | 2 | 0.01 | 0 | 0 | 0 | 0 | 0 | 0 | 0 | 0 | 0 | 0 | — | 0 | 0 | 0 | 2 | 1 |
| 106 | 2 | 5.6 | 1 | 3 | 3 | 3 | 3 | 0 | 2 | 2 | 3 | 3 | 3 | 1 | 3 | 3 | 3 | 3 |
| 106 | 2 | 1.12 | 2 | 3 | 3 | 3 | 3 | 0 | 3 | 3 | 3 | 3 | 3 | 1 | 1 | 3 | 3 | 3 |
| 106 | 2 | 0.28 | 0 | 3 | 0 | 0 | 0 | 0 | 2 | 2 | 1 | 3 | 2 | 1 | 1 | 3 | 3 | 3 |
| 106 | 2 | 0.056 | 0 | 3 | 0 | 0 | 0 | 0 | 2 | 2 | 1 | 2 | 1 | 1 | 0 | 1 | 2 | 3 |
| 108 | 2 | 5.6 | 0 | 3 | 2 | 3 | 3 | 0 | 3 | 2 | 2 | 3 | 3 | 1 | 3 | 3 | 3 | 3 |
| 108 | 2 | 1.12 | 0 | 3 | 2 | 2 | 3 | 0 | 2 | 2 | 2 | 2 | 1 | 1 | 3 | 3 | 3 | 3 |
| 108 | 2 | 0.28 | 0 | 2 | 0 | 0 | 1 | 0 | 1 | 0 | 0 | 2 | 0 | 0 | 2 | 3 | 3 | 3 |
| 108 | 2 | 0.056 | 0 | 0 | 0 | 0 | 0 | 0 | 0 | 1 | 0 | 0 | 0 | 0 | 0 | 0 | 0 | 3 |
| 109 | 2 | 5.6 | 2 | 3 | 3 | 3 | 3 | 0 | 2 | 2 | 3 | 3 | 3 | 3 | 3 | 3 | 3 | 3 |
| 109 | 2 | 1.12 | 0 | 0 | 1 | 3 | 3 | 0 | 1 | 2 | 1 | 0 | 1 | 0 | 2 | 3 | 3 | 3 |
| 109 | 2 | 0.28 | 0 | 0 | 0 | 0 | 0 | 0 | 0 | 0 | 0 | 0 | 0 | 0 | 0 | 3 | 2 | 2 |
| 109 | 2 | 0.056 | 0 | 0 | 0 | 0 | 0 | 0 | 0 | 0 | 0 | 0 | 0 | 0 | 0 | 0 | 0 | 3 |

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

In another form of aqueous suspensions, a water-immiscible herbicide is encapsulated to form microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of aqueous suspension, preferably 480 to 600 g/l.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface-active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts, preferably from about 3 to 20 parts, by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium Ureas N'-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea Carbamates/Thiolcarbamates 2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfonyl]amino]phenyl)acetamide
N-Isopropyl-2-chloroactanilide
2',6'-Diethyl-N-methoxymethyl-2-chloroacetanilide
2'-Methyl-6'-ethyl-N-(2-methoxyprop-2-yl)-2-chloroacetanilide
$\alpha,\alpha,\alpha$-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its C monoalkyl amine and alkaline metal salts and combinations thereof Ethers 2,4-Dichlorophenyl-4-nitrophenyl ether
2-Chloro-$\alpha,\alpha,\alpha$-trifluoro-p-tolyl-3-ethoxy-4-nitrodiphenyl ether Miscellaneous 2,6-Dichlorobenzonitrile
Monosodium acid methanearsonate
Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | Weight Percent |
|---|---|
| I. Emulsifiable Concentrates | |
| A. Compound No. 76 | 50.0 |
| Calcium dodecylbenzene sulfonate/polyoxyethylene ethers blend (e.g., Atlox ® 3437F and Atlox 3438F) | 5.0 |
| Monochlorobenzene | 45.0 |
| | 100.00 |
| B. Compound No. 29 | 85.0 |
| Calcium dodecyl sulfonate/alkylaryl polyether alcohol blend | 4.0 |
| C$_9$ aromatic hydrocarbons solvent | 11.0 |
| | 100.00 |
| C. Compound No. 39 | 5.0 |
| Calcium dodecylbenzene sulfonate/polyoxyethylene ethers blend (e.g., Atlox 3437F) | 1.0 |
| Xylene | 94.0 |
| | 100.00 |
| II. Liquid Concentrates | |
| A. Compound No. 76 | 10.0 |
| Xylene | 90.0 |
| | 100.00 |
| B. Compound No. 29 | 85.0 |
| Dimethyl sulfoxide | 15.0 |
| | 100.00 |
| C. Compound No. 39 | 50.0 |
| N—methylpyrrolidone | 50.0 |
| | 100.00 |
| D. Compound No. 48 | 5.0 |
| Ethoxylated castor oil | 20.0 |
| Rhodamine B | .5 |
| Dimethyl formamide | 74.5 |
| | 100.00 |
| III. Emulsions | |
| A. Compound No. 39 | 40.0 |
| Polyoxyethylene/polyoxypropylene block copolymer with butanol (e.g., Tergitol ® XH) | 4.0 |
| Water | 56.0 |
| | 100.00 |
| B. Compound No. 48 | 5.0 |
| Polyoxyethylene/polyoxypropylene block copolymer with butanol | 3.5 |
| Water | 91.5 |
| | 100.00 |
| IV. Wettable Powders | |
| A. Compound No. 48 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound No. 29 | 80.0 |
| Sodium dioctyl sulfosuccinate | 1.25 |
| Calcium lignosulfonate | 2.75 |
| Amorphous silica (synthetic) | 16.00 |
| | 100.00 |
| C. Compound No. 76 | 10.0 |
| Sodium lignosulfonate | 3.0 |
| Sodium N—methyl-N—oleyl-taurate | 1.0 |

-continued

| | Weight Percent |
|---|---|
| Kaolinite clay | 86.0 |
| | 100.00 |
| V. Dusts | |
| A. Compound No. 76 | 2.0 |
| Attapulgite | 98.0 |
| | 100.00 |
| B. Compound No. 39 | 60.0 |
| Montmorillonite | 40.0 |
| | 100.00 |
| C. Compound No. 29 | 30.0 |
| Bentonite | 70.0 |
| | 100.00 |
| D. Compound No. 48 | 1.0 |
| Diatomaceous earth | 99.0 |
| | 100.00 |
| VI. Granules | |
| A. Compound No. 76 | 15.0 |
| Granular attapulgite (20/40 mesh) | 85.0 |
| | 100.00 |
| B. Compound No. 48 | 30.0 |
| Diatomaceous earth (20/40) | 70.0 |
| | 100.00 |
| C. Compound No. 29 | 0.5 |
| Bentonite (20/40) | 70.0 |
| | 100.00 |
| D. Compound No. 39 | 5.0 |
| Pyrophyllite (20/40) | 95.0 |
| | 100.00 |
| VII. Microcapsules | |
| A. Compound No. 76 encapsulated in polyurea shell wall | 49.2 |
| Sodium lignosulfonate (e.g. Reax ® 88B) | 0.9 |
| Water | 49.9 |
| | 100.00 |
| B. Compound No. 48 encapsulated in polyurea shell wall | 10.0 |
| Potassium lignosulfonate (e.g., Reax ® C-21) | .5 |
| Water | 89.5 |
| | 100.00 |
| C. Compound No. 39 encapsulated in polyurea shell wall | 80.0 |
| Magnesium salt of lignosulfate (Treax ® LTM) | 2.0 |
| Water | 18.0 |
| | 100.00 |

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective pre-emergence application to the plants or to the soil, a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in Webster's New International Dictionary, Second Edition, Unabridged (1961). Thus, the term refers to any substance or media in which vegetation may take root and grow, and includes not only earth, but also compost, manure, muck, humus, sand and the like, adapted to support plant growth.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

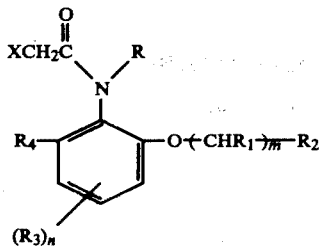

wherein
X is chloro, bromo or iodo;
R is H, $C_{1-5}$ alkyl or alkoxymethyl, cyanomethyl, azolylmethyl, $C_{3-5}$ alkenyl, alkynyl or alkenyloxymethyl;
$R_1$ and $R_3$ are H or $C_{1-4}$ alkyl;
$R_2$ is $C_{1-4}$ alkoxy, polyalkoxy, alkoxyalkyl or dialkoxymethyl, 2-furyl, 2-tetrahydrofuryl or 2-thienyl;
$R_4$ is H, $C_{1-4}$ alkyl or halogen;
m is 1 or 2; and
n is 1-3;
provided that when R is alkoxymethyl, $R_4$ is hydrogen or halogen.

2. Compound according to claim 1 wherein X is chlorine.

3. Compound according to claim 2 wherein $R_1$, $R_3$ and $R_4$ are hydrogen or methyl.

4. Compound according to claim 3 wherein $R_2$ is $C_{1-4}$ alkoxy or alkoxyalkyl.

5. Compound according to claim 4 wherein R is $C_{1-5}$ alkyl or alkoxymethyl, cyanomethyl or propargyl.

6. Compound according to claim 5 which is 2-chloro-[2'-(2-methoxy-1-methylethoxy)-6'-methyl]-N-methylacetanilide.

7. Compound according to claim 5 which is 2-chloro-[2'-(2-isopropoxyethoxy)-6'-methyl]-N-methylacetanilide.

8. Compound according to claim 5 which is 2-chloro-[2'-(2-methoxyethoxy)-6'-methyl]-N-(cyanomethyl)acetanilide.

9. Compound according to claim 5 which is 2-chloro-[-2'-(ethoxyethoxy)-6'-methyl]-N-ethylacetanilide.

10. Compound according to claim 5 which is 2-chloro-[2'-(ethoxymethoxy)-6'-methyl]-N-(2-propynyl)acetanilide.

11. Compound according to claim 2 which is 2-chloro-[2'-(2-ethoxyethoxy)-6'-chloro]-N-(ethoxymethyl)acetanilide.

12. A herbicidal composition comprising an inert adjuvant and a herbicidally effective amount of a compound of the formula

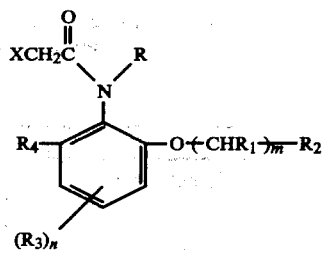

wherein
X is chloro, bromo or iodo;
R is H, $C_{1-5}$ alkyl or alkoxymethyl, cyanomethyl, azolylmethyl, $C_{3-5}$ alkenyl, alkynyl or alkenyloxymethyl;
$R_1$ and $R_3$ are H or $C_{1-4}$ alkyl;
$R_2$ is $C_{1-4}$ alkoxy, polyalkoxy, alkoxyalkyl or dialkoxymethyl, 2-furyl, 2-tetrahydrofuryl or 2-thienyl;
$R_4$ is H, $C_{1-4}$ alkyl or halogen;
m is 1 or 2; and
n is 1-3;
provided that when R is alkoxymethyl, $R_4$ is hydrogen or halogen.

13. Composition according to claim 12 wherein in said compound X is chlorine.

14. Composition according to claim 13 wherein in said compound $R_1$, $R_3$ and $R_4$ are hydrogen or methyl.

15. Composition according to claim 14 wherein in said compound $R_2$ is $C_{1-4}$ alkoxy or alkoxyalkyl.

16. Composition according to claim 15 wherein in said compound R is $C_{1-5}$ alkyl or alkoxymethyl, cyanomethyl or propargyl.

17. Composition according to claim 16 wherein said compound is 2-chloro-[2'-(2-methoxy-1-methylethoxy)-6'-methyl]-N-methylacetanilide.

18. Composition according to claim 16 wherein said compound is 2-chloro-[2'-(2-isopropoxyethoxy)-6'-methyl]-N-methylacetanilide.

19. Composition according to claim 16 wherein said compound is 2-chloro-[2'-methoxyethoxy-6'-methyl]-N-(cyanomethyl)acetanilide.

20. Composition according to claim 16 wherein said compound is 2-chloro-[2'-ethoxyethoxy)-6'-methyl]-N-ethylacetanilide.

21. Composition according to claim 16 wherein said compound is 2-chloro-[2'-ethoxymethoxy)-6'-methyl]-N-(2-propynyl)acetanilide.

22. Composition according to claim 13 wherein said compound is 2-chloro-[2'-(2-ethoxyethoxy)-6'-chloro]-N-(ethoxymethyl)acetanilide.

23. A method of controlling undesired plants which comprises contacting said plants or the plant growth medium with a herbicidal amount of a compound of the formula

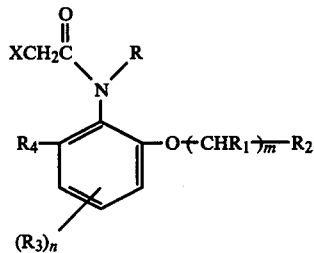

wherein

X is chloro, bromo or iodo;

R is H, $C_{1-5}$ alkyl or alkoxymethyl, cyanomethyl, azolylmethyl, $C_{3-5}$ alkenyl, alkynyl or alkenyloxymethyl;

$R_1$ and $R_3$ are H or $C_{1-4}$ alkyl;

$R_2$ is $C_{1-4}$ alkoxy, polyalkoxy, alkoxyalkyl or dialkoxymethyl, 2-furyl, 2-tetrahydrofuryl or 2-thienyl;

$R_4$ is H, $C_{1-4}$ alkyl or halogen;

m is 1 or 2 and n is 1–3;

provided that when R is alkoxymethyl, $R_4$ is hydrogen or halogen.

24. A method according to claim 23 wherein in said compound X is chlorine.

25. A method according to claim 24 wherein in said compound $R_1$, $R_3$ and $R_4$ are hydrogen or methyl.

26. A method according to claim 25 wherein in said compound $R_2$ is $C_{1-4}$ alkoxy or alkoxyalkyl.

27. A method according to claim 26 wherein in said compound R is $C_{1-5}$ alkyl or alkoxymethyl, cyanomethyl or propargyl.

28. A method according to claim 27 wherein said compound is 2-chloro-[2'-(2-methoxy-1-methylethoxy)-6'-methyl]-N-methylacetanilide.

29. A method according to claim 27 wherein said compound is 2-chloro-[2'-(2-isopropoxyethoxy)-6'-methyl]-N-methylacetanilide.

30. A method according to claim 27 wherein said compound is 2-chloro-[2'-(2-methoxyethoxy)-6'-methyl]-N-(cyanomethyl)acetanilide.

31. A method according to claim 27 wherein said compound is 2-chloro-[2'-(ethoxyethoxy)-6'-methyl]-N-ethylacetanilide.

32. A method according to claim 27 wherein said compound is 2-chloro-[2'-(ethoxymethoxy)-6'-methyl]-N-(2-propynyl)acetanilide.

33. A method according to claim 27 wherein said compound is 2-chloro-[2'-(2'ethoxyethoxy)-6'-chloro]-N-(ethoxymethyl)acetanilide.

* * * * *

UNITED STATES PATENT AND TRADEMARK OFFICE
CERTIFICATE OF CORRECTION

PATENT NO. : 4,451,285

DATED : May 29, 1984

INVENTOR(S) : Gerhard H. Alt

It is certified that error appears in the above-identified patent and that said Letters Patent is hereby corrected as shown below:

Columns 19-20, Table IV-continued, "Found" column, line 4:
   "58.89" should be --59.89--

Column 25, line 23: "in" should be --is--

Columns 35-36, Table X-continued, "K" column, line 37:
   "2" should be --3--

Columns 37-38, Table X-continued, "R" column, line 48:
   "3" should be --2--

Column 44, line 61: "C" should be --$C_{1-6}$--

Column 45, line 68: "10" should be --1.0--

UNITED STATES PATENT AND TRADEMARK OFFICE
CERTIFICATE OF CORRECTION

PATENT NO. : 4,451,285

DATED : May 29, 1984

INVENTOR(S) : Gerhard H. Alt

It is certified that error appears in the above-identified patent and that said Letters Patent is hereby corrected as shown below:

Column 1, line 51: "ethylacetanilde" should be --ethylacetanilide--

Columns 7-8, Table I-continued, "Calc'd." column, line 3: "5.744" should be --57.44--

Column 23, line 40: "procuct" should be --product--

Signed and Sealed this

Thirteenth Day of November 1984

[SEAL]

*Attest:*

*Attesting Officer*

GERALD J. MOSSINGHOFF

*Commissioner of Patents and Trademarks*